(12) United States Patent
Arora et al.

(10) Patent No.: US 9,448,219 B2
(45) Date of Patent: Sep. 20, 2016

(54) ELECTRO-MECHANICAL SWITCHES AND METHODS OF USE THEREOF

(71) Applicants: William Jay Arora, Cambridge, MA (US); Karen K. Gleason, Cambridge, MA (US); George Barbastathis, Boston, MA (US); Wyatt E. Tenhaeff, Cambridge, MA (US)

(72) Inventors: William Jay Arora, Cambridge, MA (US); Karen K. Gleason, Cambridge, MA (US); George Barbastathis, Boston, MA (US); Wyatt E. Tenhaeff, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 84 days.

(21) Appl. No.: 13/893,699

(22) Filed: May 14, 2013

(65) Prior Publication Data

US 2014/0127822 A1   May 8, 2014

Related U.S. Application Data

(63) Continuation of application No. 12/507,283, filed on Jul. 22, 2009, now Pat. No. 8,441,081.

(60) Provisional application No. 61/082,678, filed on Jul. 22, 2008.

(51) Int. Cl.
  *G01N 27/04* (2006.01)
  *G01N 33/00* (2006.01)
  *G01N 27/12* (2006.01)

(52) U.S. Cl.
  CPC ........ *G01N 33/0057* (2013.01); *G01N 27/128* (2013.01); *Y10T 436/147777* (2015.01); *Y10T 436/163333* (2015.01); *Y10T 436/173076* (2015.01); *Y10T 436/173845* (2015.01)

(58) Field of Classification Search
  CPC .. G01N 27/04; G01N 27/045; G01N 27/125; G01N 27/126
  USPC ............................................ 422/82.01, 82.02
  See application file for complete search history.

(56) References Cited

U.S. PATENT DOCUMENTS

| | | | |
|---|---|---|---|
| 6,167,748 B1 * | 1/2001 | Britton, Jr. | ............. G01B 7/023 422/69 |
| 7,179,421 B1 | 2/2007 | Ho | |
| 7,189,360 B1 | 3/2007 | Ho | |
| 8,184,668 B2 | 5/2012 | Sun et al. | |
| 2002/0185384 A1 | 12/2002 | Leong et al. | |
| 2005/0164285 A1 | 7/2005 | Patel et al. | |
| 2006/0050350 A1 | 3/2006 | Rijks et al. | |

(Continued)

OTHER PUBLICATIONS

Arora WJ et al., Integration of reactive polymeric nanofilms into a low-power electromechanical switch for selective chemical sensing. *J Microelectromechanical Systems* 18(1):97-102 (2009).

(Continued)

*Primary Examiner* — Jan Ludlow
(74) *Attorney, Agent, or Firm* — Dana M. Gordon; Foley Hoag LLP

(57) ABSTRACT

One aspect of the invention relates to an ultrathin microelectromechanical chemical sensing device which uses swelling or straining of a reactive organic material for sensing. In certain embodiments, the device comprises a contact on-off switch chemical sensor. For example, the device can comprises a small gap separating two electrodes, wherein the gap can be closed as a result of the swelling or stressing of an organic polymer coating on one or both sides of the gap. In certain embodiments, the swelling or stressing is due to the organic polymer reacting with a target analyte.

29 Claims, 19 Drawing Sheets

(56) References Cited

U.S. PATENT DOCUMENTS

| | | |
|---|---|---|
| 2006/0065528 A1 | 3/2006 | Lopez et al. |
| 2006/0257286 A1 | 11/2006 | Adams |
| 2007/0116607 A1 | 5/2007 | Wang et al. |
| 2007/0278600 A1 | 12/2007 | Zhan et al. |
| 2009/0011946 A1* | 1/2009 | Majumdar ....... G01N 33/54373 506/9 |

OTHER PUBLICATIONS

International Search Report from related International Patent Application No. PCT/US2009/051385, dated Mar. 5, 2010.

* cited by examiner

Figure 6
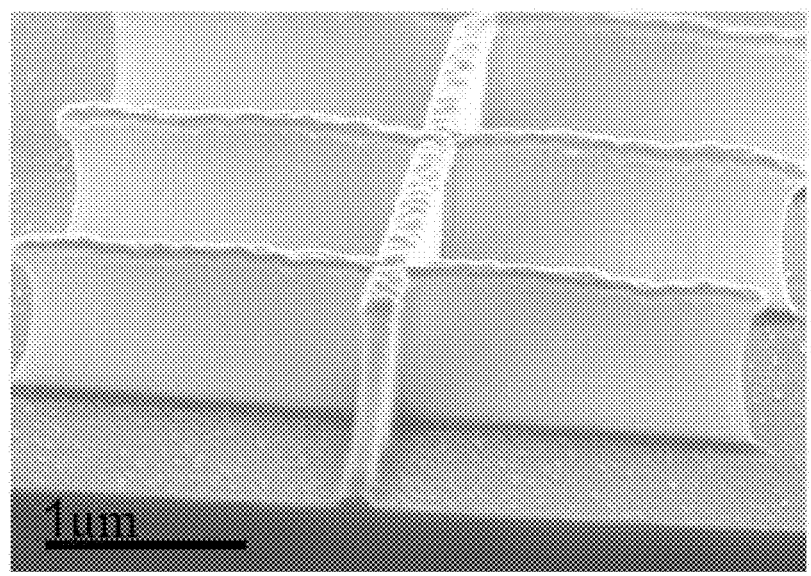
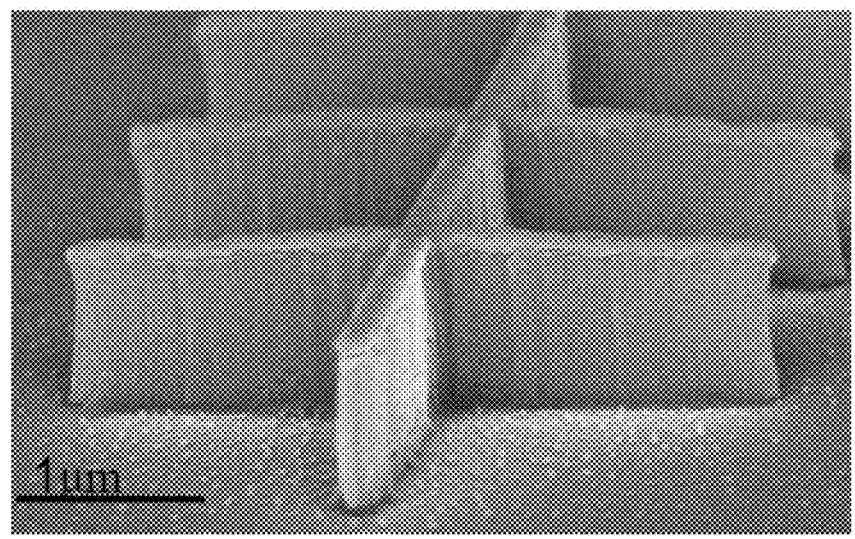

Figure 7

|  | selected sensors of the invention | best performance in literature |
|---|---|---|
| Power Consumption | < 2 nW | "low-power", mW? |
| Output Response | on / off switching | requires threshold circuitry |
| Sensitivity | ppthousand demonstrated (ppb possible) | optically ~ pptrillion (others ~ ppthousand) |
| Response Time | minutes | minutes |
| Cost / Size | fully integrated MEMS | laser, photodetector, computer |

Figure 9
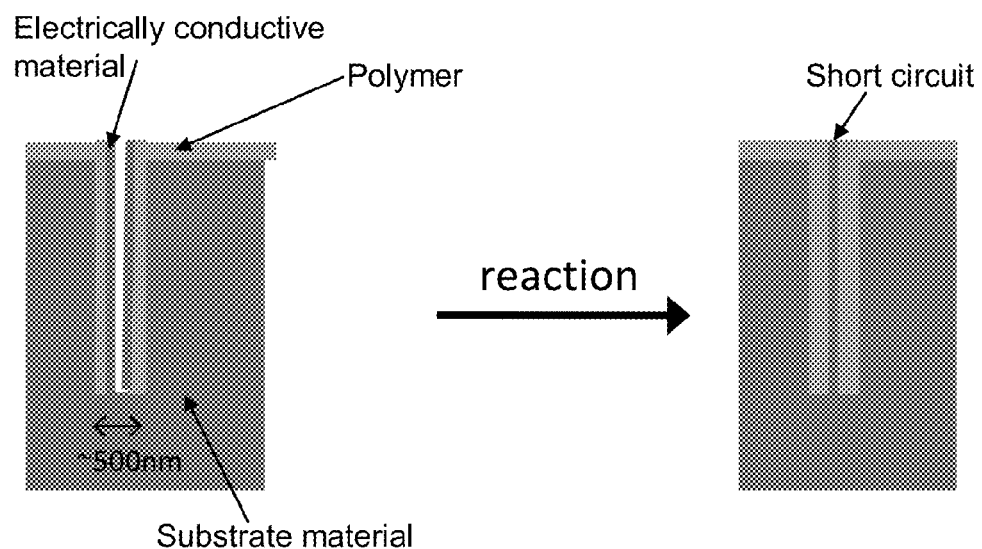
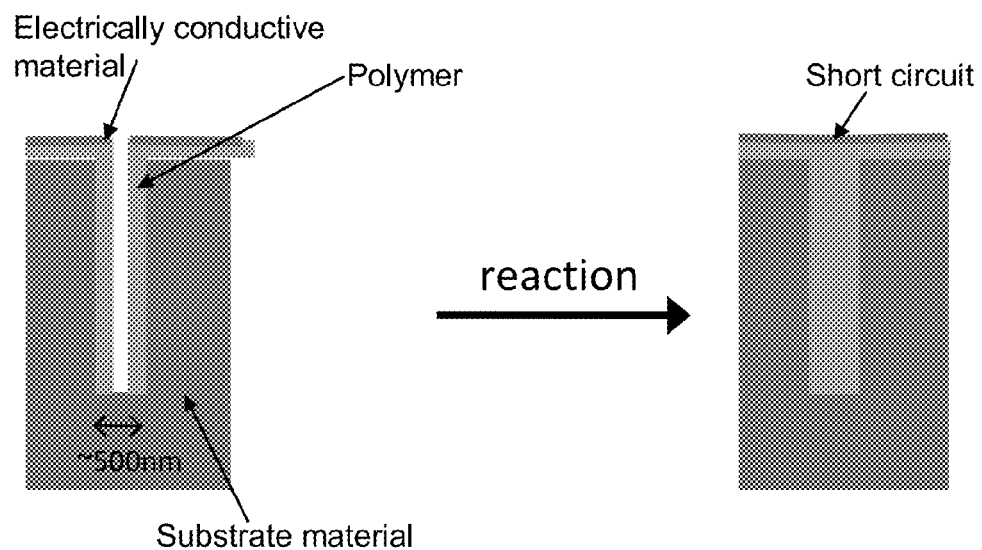

Figure 10
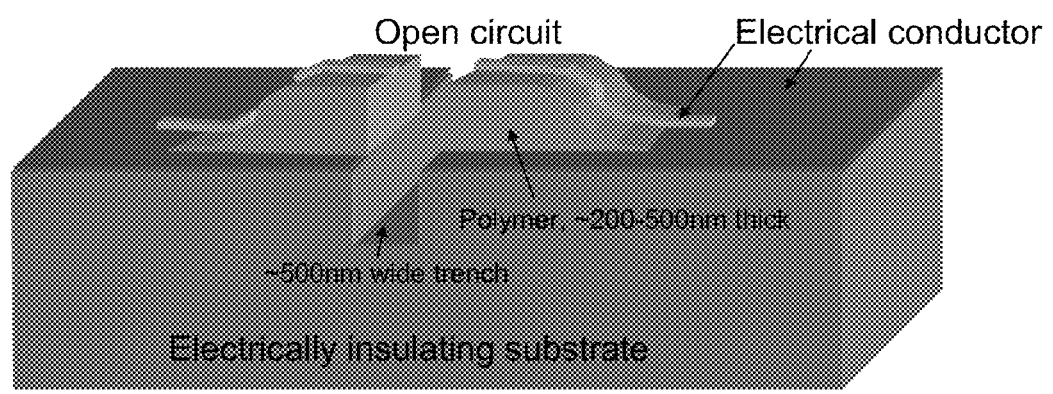
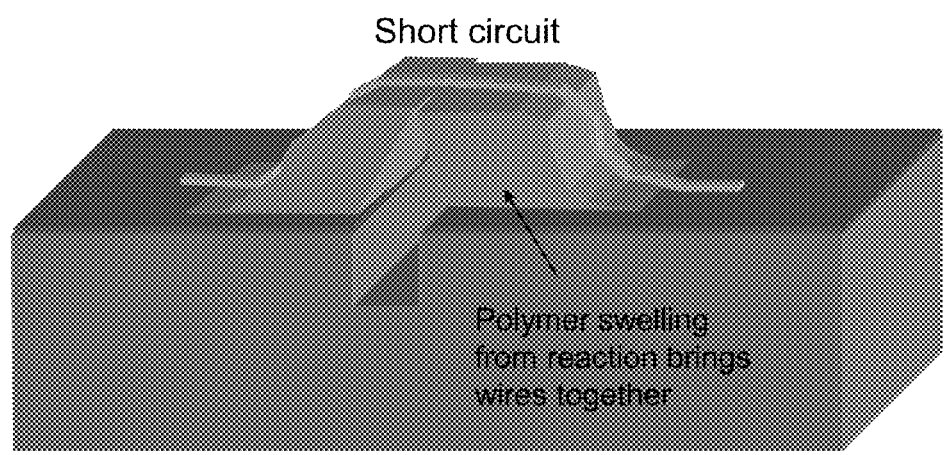

Figure 19
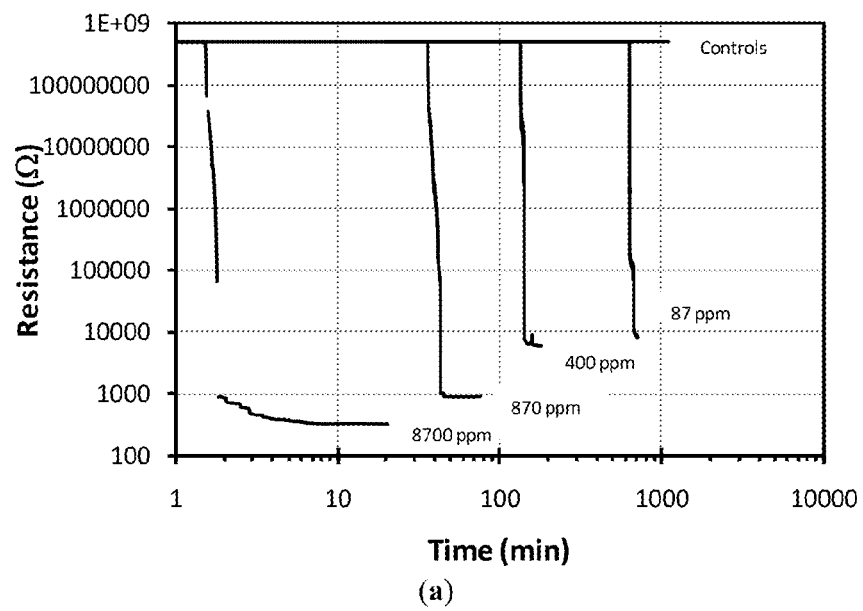
(a)
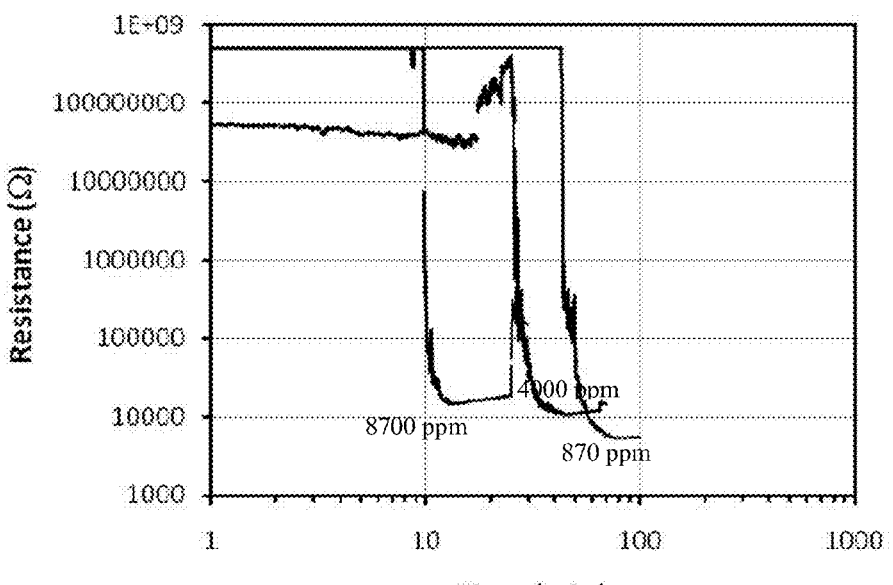
(b)

ELECTRO-MECHANICAL SWITCHES AND METHODS OF USE THEREOF

RELATED APPLICATIONS

This application is a continuation of U.S. patent application Ser. No. 12/507,283, filed Jul. 22, 2009, which claims the benefit of priority to U.S. Provisional Patent Application Ser. No. 61/082,678, filed Jul. 22, 2008, the entire content of both of which is hereby incorporated by reference.

GOVERNMENT SUPPORT

This invention was made with support under grant number W911NF-07-D-0004, awarded by the Army Research Office. The government has certain rights in this invention.

BACKGROUND

Chemical sensing science is a field with many applications in industry, security, and defense. A multitude of detection mechanisms exist, but many are only applicable to very specific situations. Generally, effective chemical sensing needs to be highly selective to a target analyte and result in a large electrical response.

Transducing a chemical response into an electrical response can be done most directly with a chemiresistive polymer, in which the reaction either acts to dope or undope a semiconducting polymer [J. Janata and M. Josowicz, "Conducting polymers in electronic chemical sensors," *Nature Materials*, vol. 2, pp. 19-24, January 2003] or cause a conductivity change by swelling a partially conductive polymer [D. Rivera, M. K. Alam, C. E. Davis, and C. K. Ho, "Characterization of the ability of polymeric chemiresistor arrays to quantitate trichloroethylene using partial least squares (PLS): effects of experimental design, humidity, and temperature," *Sensors and Actuators B-Chemical*, vol. 92, pp. 110-120, July 2003].

However, detection of an analyte may also be done mechanically, such as with a microcantilever. Microcantilevers are a common platform for transducing a chemical response into a mechanical one. One surface of the cantilever is coated with a material (often a polymer) that the target chemical will interact with, typically through absorption (swelling) or reaction. The interaction creates a stress that causes the cantilever to bend. Existing methods rely on measuring small cantilever deflections of less than a few microns [N. V. Lavrik, M. J. Sepaniak, and P. G. Datskos, "Cantilever transducers as a platform for chemical and biological sensors," *Review of Scientific Instruments*, vol. 75, pp. 2229-2253, July 2004] or measuring resonance frequency changes due to a mass increase. In order to measure these small changes, optical [F. M. Battiston, J. P. Ramseyer, H. P. Lang, M. K. Baller, C. Gerber, J. K. Gimzewski, E. Meyer, and H. J. Guntherodt, "A chemical sensor based on a microfabricated cantilever array with simultaneous resonance-frequency and bending readout," *Sensors and Actuators B-Chemical*, vol. 77, pp. 122-131, June 2001], piezoelectric [J. D. Adams, G. Parrott, C. Bauer, T. Sant, L. Manning, M. Jones, B. Rogers, D. McCorkle, and T. L. Ferrell, "Nanowatt chemical vapor detection with a self-sensing, piezoelectric microcantilever array," *Applied Physics Letters*, vol. 83, pp. 3428-3430, October 2003], piezoresistive [N. Abedinov, P. Grabiec, T. Gotszalk, T. Ivanov, J. Voigt, and I. W. Rangelow, "Micromachined piezoresistive cantilever array with integrated resistive microheater for calorimetry and mass detection," *Journal of Vacuum Science & Technology a-Vacuum Surfaces and Films*, vol. 19, pp. 2884-2888, November-December 2001] or capacitive [D. R. Baselt, B. Fruhberger, E. Klaassen, S. Cemalovic, C. L. Britton, S. V. Patel, T. E. Mlsna, D. McCorkle, and B. Warmack, "Design and performance of a microcantilever-based hydrogen sensor," *Sensors and Actuators B-Chemical*, vol. 88, pp. 120-131, January 2003] schemes are employed.

For example, microcantilevers with a compound immobilized on the surface on the free end have been used to detect and screen receptor/ligand interactions, antibody/antigen interactions and nucleic acid interactions (U.S. Pat. No. 5,992,226, issued on Nov. 30, 1999). Deflection was measured using optical and piezoelectric methods.

Microcantilevers can also be used to measure concentrations using electrical methods to detect phase difference signals that can be matched with natural resonant frequencies (U.S. Pat. No. 6,041,642, issued Mar. 28, 2000.) Determining a concentration of a target species using a change in resonant properties of a microcantilever on which a known molecule is disposed, for example, a macromolecular biomolecule such as DNA, RNA, and protein, is described in U.S. Pat. No. 5,763,768

Another method and apparatus for detecting and measuring physical and chemical parameters in a sample media uses micromechanical potentiometric sensors (U.S. Pat. No. 6,016,686, issued Jan. 25, 2000). Detection of a chemical analyte is described in U.S. Pat. No. 5,923,421, issued Jul. 13, 1999. Magnetic and electrical monitoring of radioimmune assays, using antibodies specific for target species which cause microcantilever deflection, e.g., magnetic beads binding the target to the microcantilever, are described in U.S. Pat. No. 5,807,758, issued Sep. 15, 1998.

U.S. Pat. No. 6,096,559 issued Aug. 1, 2000, and U.S. Pat. No. 6,050,722 issued Apr. 18, 2000, describe fabrication of a microcantilever, including use of material such as ceramics, plastic polymers, quartz, silicon nitride, silicon, silicon oxide, aluminum oxide, tantalum pentoxide, germanium, germanium dioxide, gallium arsenide, zinc oxide, and silicon compounds. Coating of micromechanical sensors with various interactive molecules is described in U.S. Pat. No. 6,118,124, issued Sep. 12, 2000.

However, these and other known methods suffer from lack of analyte specificity, offer small resistance changes and/or draw continuous power. In addition, an intermediate transduction step, often optical or mechanical, is used. Further, these measurements are susceptible to ambient interference and require additional power-consuming electronic circuitry. It has been suggested that the requirement of relatively thick sensing layers, typically on the order of several micrometers, in soft-matter-based sensors (i.e. polymers) is another major disadvantage as it limits their incorporation into nano-scale devices [S. Singamaneni, M. C. LeMieux, H. P. Lang, C. Gerber, Y. Lam, S. Zauscher, P. G. Datskos, N. V. Lavrik, H. Jiang, R. R. Naik, T. J. Bunning, and V. V. Tsukruk, "Bimaterial microcantilevers as a hybrid sensing platform," *Advanced Materials*, vol. 20, pp. 653-680, February 2008]. The best cases of "ultrathin" sensors have thicknesses greater than 300 nm. Furthermore, such systems show only partial selectivity, which is based on the rate of different molecules diffusing into polymer layers.

Therefore, there is a need for improved chemical sensors which, for example, do not require optical, piezoelectric, piezoresistive or capacitive measuring schemes; are not susceptible to ambient interference; and do not require additional power-consuming electronic circuitry.

SUMMARY OF THE INVENTION

One aspect of the invention relates to an ultrathin micro-electromechanical chemical sensing device which uses swelling or straining of a reactive organic material for sensing. In certain embodiments, the device comprises a contact on-off switch chemical sensor. For example, the device can comprises a small gap separating two electrodes, wherein the gap can be closed as a result of the swelling or stressing of an organic polymer coating on one or both sides of the gap. In certain embodiments, the swelling or stressing is due to the organic polymer reacting with a target analyte.

In certain embodiments, the micro-electromechanical chemical sensing device comprises a microcantilever.

In certain embodiments, the microcantilevers are etched from silicon nitride, and a reactive copolymer film for sensing an analyte is deposited on the silicon nitride microcantileverby initiated chemical vapor deposition. In certain embodiments, crosslinking densities of the reactive copolymer film is controlled during the deposition process; the greater the crosslinking density, the greater the cantilever deflections upon the polymer's reaction with the analyte. Importantly, because chemical reactions are necessary for stress formation, the sensing is selective. In certain embodiments, cantilever deflections of greater than about 50 μm allow a simple switch to be designed with resistance-based outputs. Remarkably, when certain sensing devices (e.g., those fabricated from about 100 nm-thick silicon nitride and a about 75 nm-thick reactive copolymer) are exposed to a hexylamine vapor phase concentration of about 0.87 mol %, the resistance of the switch drops by over six orders of magnitude with a response time less than about 90 seconds.

BRIEF DESCRIPTION OF THE FIGURES

FIG. 6 depicts one embodiment of a switch-type sensor with patterned pMaVD before reacting with hexylamine both before (top) and after (bottom) the reaction; it is observed that the polymer expands mostly laterally (about 50-100%) and only about 10-20% vertically.

FIG. 7 depicts a table showing a comparison of power consumption, output response, sensitivity, response time and cost/size for inventive sensors and those described in the literature.

FIGS. 8-10 depict dimensions, compositions of components, and configurations of several different embodiments of sensors of the invention.

FIGS. 19 (a) and (b) depict the response of sensors based on the permanent deflection of microcantilevers as a poly (Ma-D) coating reacts with hexylamine. (b) Responses of the pMA-coated trench sensors upon exposure to hexylamine. In (a) hexylamine was introduced into the chamber at t=0. In (b) no hexylamine was introduced at t=5 min; the first five minutes was pure $N_2$. (The breaks in the lines are artifacts of the logging multimeter.)

DETAILED DESCRIPTION

Figure 1:
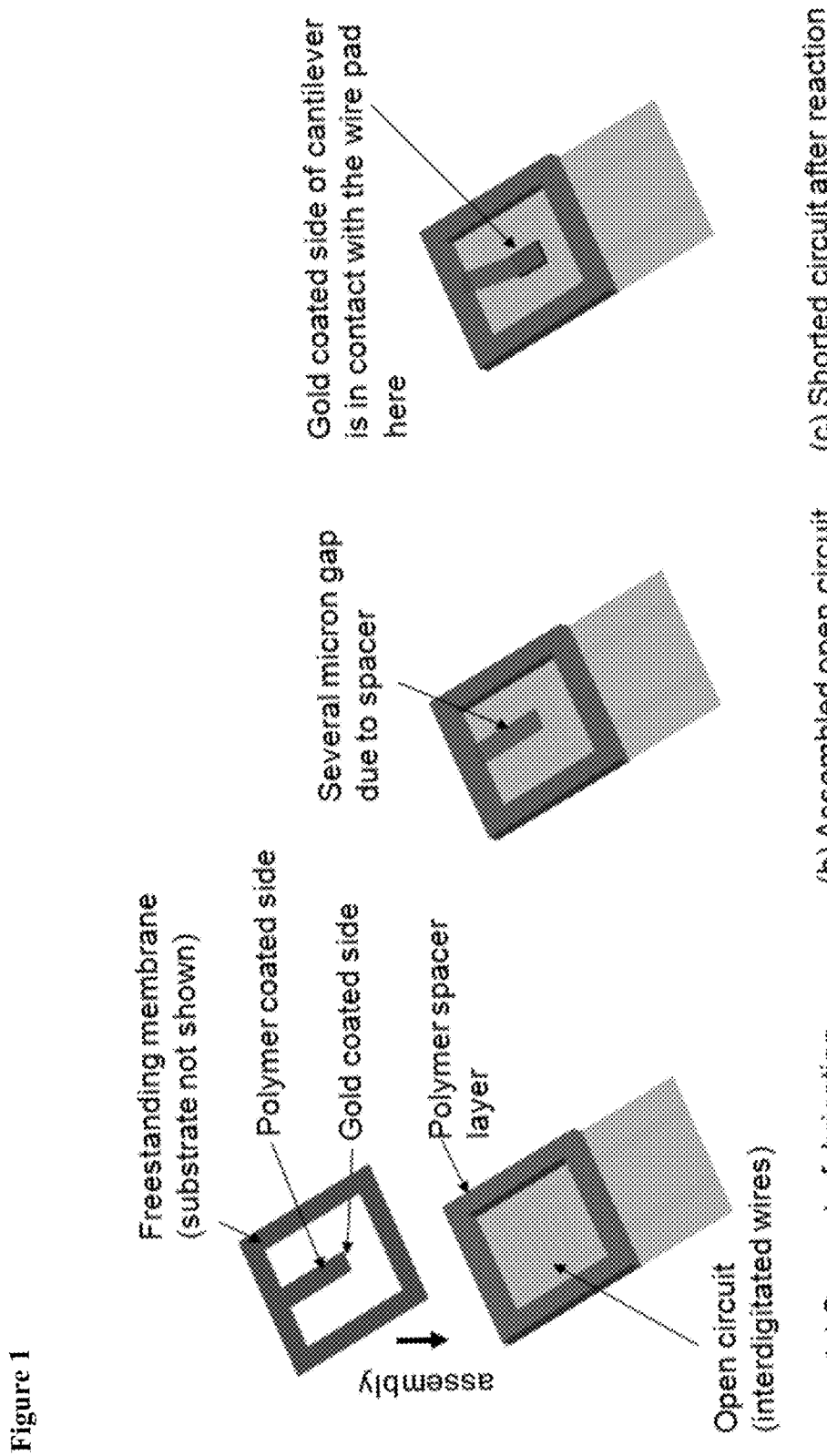
FIG. 1 depicts a schematic of the assembly and operation of a micro-switch. (a) A silicon nitride cantilever, still attached to a silicon handle wafer frame (not shown) is coated with 75 nm of iCVD polymer on one side and evaporated gold on the other. Interleaved gold wires are patterned onto a separate silicon wafer with a silicon nitride (non-conducting) top surface. (b) A 3 μm thick spacer is formed around the gold wires using a photo-polymer. The cantilever is placed onto the spacer layer. (c) Upon reaction with the target vapor the polymer strains, forcing the cantilever to bend down and contact the interleaved gold wires. The conductive gold underside of the cantilever short-circuits these wires.

One aspect of the invention relates to a sensing mechanism that achieves high selectivity, because it relies on covalent bond formation, and achieves a large electrical resistance change due to its design as an electro-mechanical switch. In certain embodiments, the chemically selective component is a reactive polymer deposited by initiated chemical vapor deposition (iCVD) onto a three-dimensional micro-switch.

In certain embodiments, the polymer is engineered to produce a large stress when it reacts with an analyte, deforming the switch and causing it to short-circuit. In certain embodiments, the switch comprises a microcantilever. For example, a switch based on microcantilever deflection and resistance-based outputs is disclosed herein. Remarkably, when one of these devices is exposed to a hexylamine vapor phase concentration of 0.87 mol %, the resistance of the switch drops by over six orders of magnitude with a response time less than 90 seconds.

In addition to sensors for amines such as the one just described, it is proposed that a wide range of analytes can be detected by using the general platform method of iCVD to synthesize additional types of reactive organic nanocoatings, each offering a specific complimentary reactive functional group. See, for example: J. Janata and M. Josowicz, "Conducting polymers in electronic chemical sensors," *Nature Materials*, vol. 2, pp. 19-24, January 2003; and D. Rivera, M. K. Alam, C. E. Davis, and C. K. Ho, "Characterization of the ability of polymeric chemiresistor arrays to quantitate trichloroethylene using partial least squares (PLS): effects of experimental design, humidity, and temperature," *Sensors and Actuators B-Chemical*, vol. 92, pp. 110-120, July 2003.

In certain embodiments, a microprocessor can be included in any apparatus or a method of the invention. An example of a microprocessor is an integrated circuit containing the arithmetic, logic, and control circuitry required to interpret and execute instructions from a computer program.

Microcantilever-Containing Sensors

As used herein, the term "microcantilever" is a structural term that refers to a flexible beam that may be bar-shaped, V-shaped, or have other shapes, depending on its application. One end of the microcantilever is fixed on a supporting base, another end is free standing. Microcantilevers are usually of microscopic dimensions, for example, the length of a microcantilever can be between about 100 nm to about 10,000 μm. In certain embodiments, the length is between about 10 μm and about 1,000 μm. Further, the width of a microcantilever can be between about 100 nm to about 10,000 μm. In certain embodiments, the width is between about 10 μm and about 1,000 μm. In addition, the height of a microcantilever can be, for example, from about 0.01 μm to about 10 μm. In certain embodiments, the height is between about 0.02 μm and about 1 μm.

Microcantilevers can be manufactured from a variety of materials, including, for example, ceramics, silicon, silicon nitride, silicon dioxide, silicon carbide, other silicon compounds, metals, metal oxides, transition metals, transition metal oxides, gallium arsenide, germanium, germanium dioxide, zinc oxide, diamond, quartz, palladium, tantalum pentoxide, and plastic polymers. Plastic polymers can include: polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, and polythiophene. Microcantilevers that are custom fabricated can be obtained from commercial sources.

The term "top surface" of a microcantilever, as used herein, refers to that geometric surface of the microcantilever designed to receive and bind an analyte (such as an amine). Importantly, one or more polymer coatings which can bind the analyte are deposited upon the first surface. In certain embodiments the top surface is pretreated with a compound to aid in the binding of polymer to the top surface. In certain embodiments, the top surface is pretreated with an aminoalkyl silane (e.g., 3-aminopropyldimethylethoxysilane). The deflection or bending of the microcantilever from a first position to at a second position, whereby the microcantilever contacts the substrate (as defined below), is due to a stress on the first surface of the microcantilever resulting from the analyte contacting of the microcantilever.

The term "bottom surface" of a microcantilever, as used herein, refers to the geometric surface of a microcantilever opposite the "top surface" and facing the substrate (as defined below). When the bottom surface itself is not electrically conductive, one or more electrically conductive materials (e.g., gold) is coated on the bottom surface. As used herein, "electrically conductive materials" include electrically semi-conductive materials.

Thus the term "substrate" refers to a structural element which is positioned under the microcantilever element with a gap therebetween. In certain embodiments, the substrate comprises an open circuit. The open circuit can be closed by the bottom surface of the microcantilever element when the microcantilever is deflected or bent, due to the binding of an analyte to the top surface, so that the microcantilever contacts the substrate. The substrate is generally not coated and may comprised the material from which the microcantilever is fabricated, prior to any coating procedure applied to the top and/or bottom surfaces. However, the substrate may comprise a different material than the microcantilever and/or may be coated with a material different from the polymer coating on the top surface.

The assembly and operation of one embodiment of the invention is shown in FIG. 1; the fabrication and testing of this embodiment are described in the Exemplification section below. Inspiration was derived from work on the Nanostructured Origami™ method of folding patterned membranes into three-dimensional microstructures [W. J. Arora, A. J. Nichol, H. I. Smith, and G. Barbastathis, "Membrane folding to achieve three-dimensional nanostructures: Nanopatterned silicon nitride folded with stressed chromium hinges," *Applied Physics Letters*, vol. 88, p. 053108, January 2006; W. J. Arora, S. Sijbrandij, L. Stern, J. Notte, H. I. Smith, and G. Barbastathis, "Membrane folding by helium ion implantation for three-dimensional device fabrication," *Journal of Vacuum Science & Technology B*, vol. 25, pp. 2184-2187, November 2007; and A. J. Nichol, P. S. Stellman, W. J. Arora, and G. Barbastathis, "Two-step magnetic self-alignment of folded membranes for 3D nanomanufacturing," *Microelectronic Engineering*, vol. 84, p. 1168, May-August 2007]. In Nanostructured Origami™ methods, the stress from a deposited metal or ion implantation is used to fold a thin silicon nitride cantilever into a static structure. However, in contrast, the structure of the micro-electromechanical sensors described herein is dynamic, because the cantilever bends as the polymer stresses. Initially, the switch is an open circuit (FIG. 1b) separating a micro-battery (e.g. supercapacitors and ultracapacitors) from circuitry such as a micro-antenna (e.g. a RF transmitter). Therefore, almost no power is consumed until the switch closes, and no logic circuitry is needed to determine a threshold of cantilever deflection magnitude. A separate receiver unit can be used to record the signal.

In other embodiments, the device is wirelessly read (e.g. by using RFID technology). For example, a device may be constructed so that a response will only be sent back if the circuit on the chip is complete or shorted. In such embodiments there is no need for a battery. In addition, the identity of each chip can be encoded in its RFID tag. In certain embodiments, the devices further comprise logic circuitry (e.g. CMOS transistor logic), commonly found in microcontrollers, which usually around 10-10,000 microwatts depending on how much computation is required for the application.

Maximizing the bending force and deflection magnitude of the polymer-coated cantilevers is critical to minimize the response time and contact resistance of the closed switch. For effective transmission of the stress into mechanical bending, there must be good adhesion at the polymer-cantilever interface and the polymer must develop a large stress from reacting with the analyte. When the analyte reacts with the polymer, it forces the polymer to expand due to the added volume. Chemical linkages in the network structure restrict expansion of crosslinked polymer films, so instead they stress compressively. With iCVD (described below), the degree of crosslinking is accurately controlled by the ratio of cross-linker monomer to functional monomer [K. Chan and K. K. Gleason, "Initiated chemical vapor deposition of linear and cross-linked poly(2-hydroxyethyl methacrylate) for use as thin-film hydrogels," *Langmuir*, vol. 21, pp. 8930-8939, September 2005].

The sensor concept relies on creating as much stress in the polymer as possible from the reaction to maximize the resulting cantilever curvature. The amount of stress induced by the reaction depends on the degree of cross-linking in the polymer. This is intuitively understood because upon reacting with the analyte the polymer increases its mass, causing stress. If it is only lightly crosslinked, it will expand to relieve the stress. However, if it the polymer is glassy (highly crosslinked), it cannot easily expand and remains in a state of stress. One can model the strain that forms by Equation (1):

$$\varepsilon_x = \varepsilon_y = \sqrt[3]{\frac{v_{ex} - v_{sf}}{v_{sf}}} = \sqrt[3]{\frac{v_{ex}}{v_{sf}}} - 1 \quad (1)$$

where $\epsilon_x$ and $\epsilon_y$ are the in-plane strain components of the copolymer coating, $v_{ex}$ is the actual, experimentally observed molar volume of the reacted polymer film and $v_{sf}$ is the molar volume the polymer in a stress free state. The stress free state is a theoretical condition in which the polymer is able to freely expand without limitations imposed by the crosslinks. This equation is based on similar work by Wen et al. [M. Wen, L. E. Scriven, and A. V. McCormick, "Differential scanning calorimetry and cantilever deflection studies of polymerization kinetics and stress in ultraviolet curing of multifunctional (meth)acrylate coatings," *Macromolecules*, vol. 35, pp. 112-120, January 2002], who examined stress formation due to shrinkage when polymer coatings are cured.

One assumption in Equation (1) is that the polymer volume can expand only in the direction normal to the surface, while the expansion in the lateral dimension is constrained by adhesion to the substrate. It is clear from this equation that greater strain will develop with increased coating crosslinking density since this limits volume expansion. To analyze the effect of analyte volume on stress, one makes the assumption that there is a limiting value for $v_{ex}$ due to the presence of crosslinks, while $v_{sf}$ will increase concomitantly with analyte size in order to maintain a constant density. In sum, the magnitude of the strain should increase with increasing analyte size.

Sensors Comprising Other Switches

Figure 5:
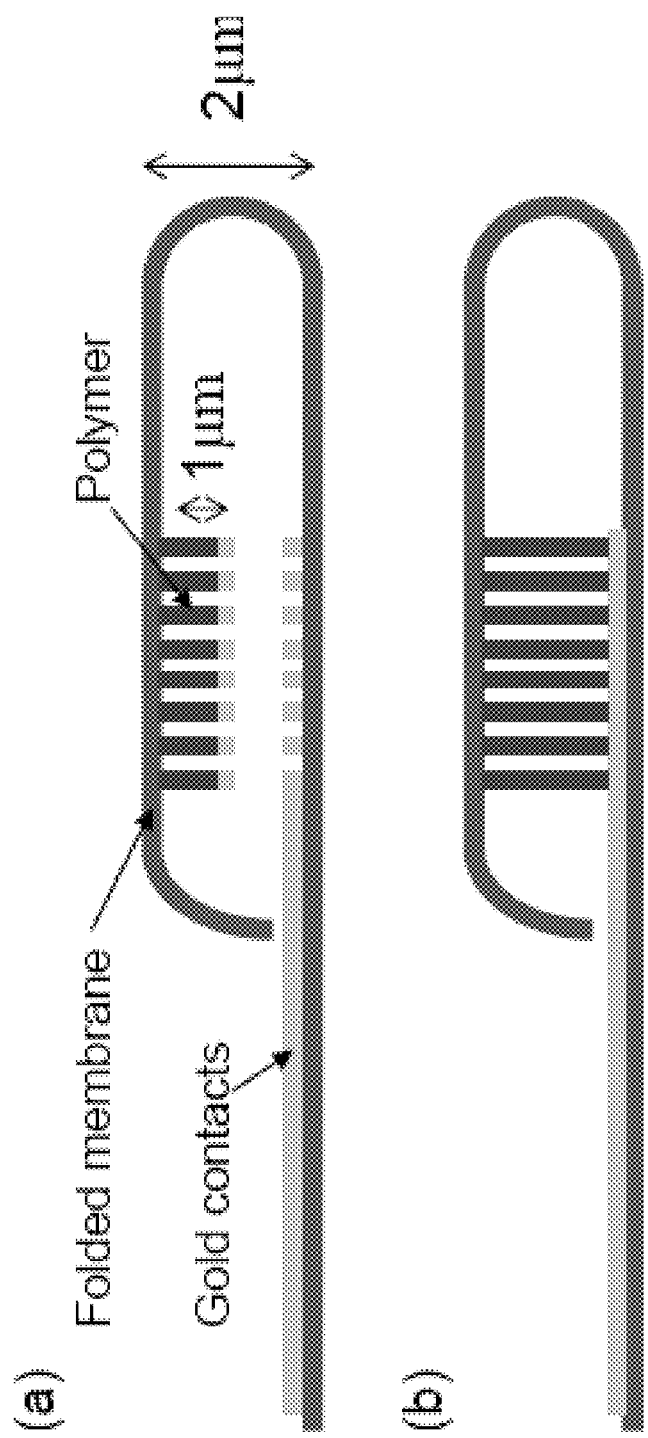
FIG. 5 depicts one embodiment of a switch-type sensor wherein (a) the polymer is nanopatterned into thin tall lines so that the chemical reaction takes place over maximum area and is not diffusion limited; and (b) the polymer expands by 100%, shorting the metal contacts.
Figure 8:
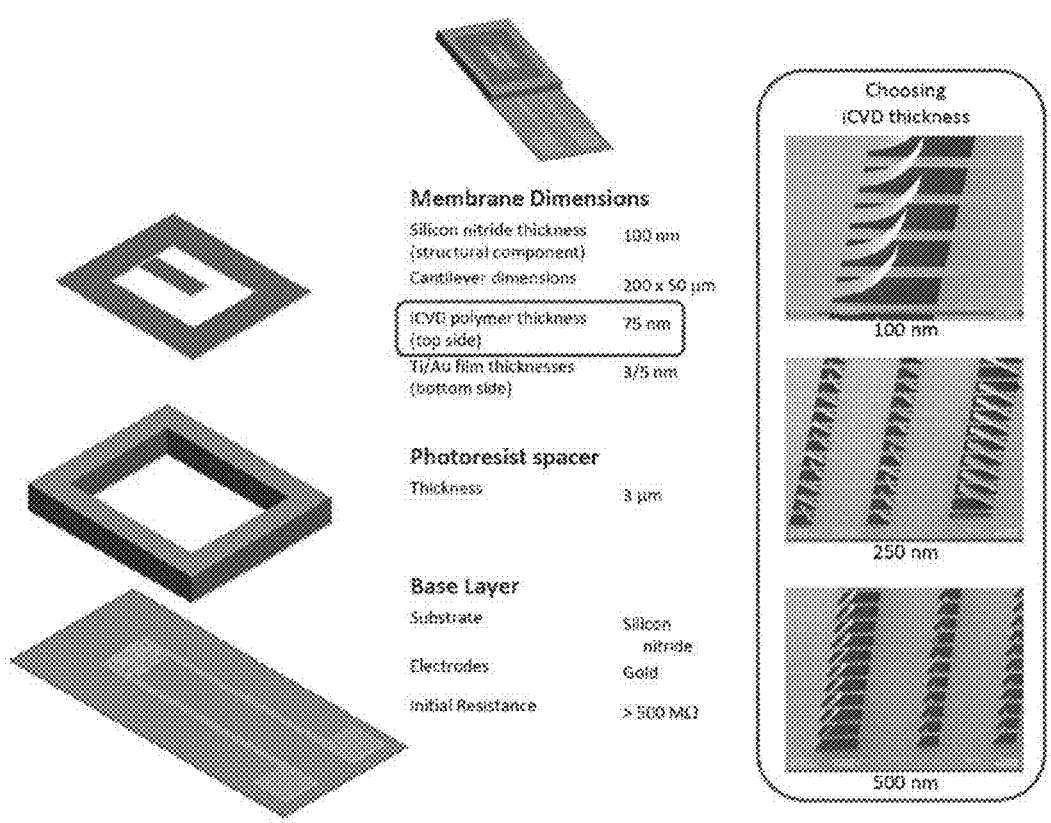

In certain embodiments, the sensors of the invention do not contain microcantilevers, but instead have other micromechanical switches which rely on the swelling and/or straining of reactive organic material for sensing analytes. Examples of such devices are shown in FIGS. 5, 9 and 10, and are discussed below in Example 7.

In certain embodiments, the sensing ability of these devices is derived from polymers undergoing large volume expansion upon reacting with an analyte. As with the microcantilever-containing devices, in certain embodiments, the devices of the invention comprise a gap or a trench which is spanned or filled by expanding polymers (as a result of contact with an analyte) thereby connecting electrically-conductive material and thus creating a short circuit.

Compared to other sensors, in certain embodiments wherein there is a low density of the polymer, the analyte can diffuse quickly through the polymer resulting in more rapid polymer-analyte reaction which leads to a decreased (improved) response time. In addition, in certain embodiments it may be easier to control the gap between electrodes with the polymer deposited over/around a pre-etched trench or gap in a substrate compared to using a spacer between a micro-cantilever and the substrate.

iCVD Polymer Coatings

In addition to an improved transduction scheme as described above, sensing selectivity is greatly improved by using another recently developed technique: initiated chemical vapor deposition (iCVD). iCVD enables designing the deposited polymer with specific functional groups that will chemically react with the target analyte. Several choices of functional monomers are available, meaning that many classes of compounds can be sensed.

iCVD provides a uniform or substantially uniform coating on rough, fibrous, and porous morphologies with high surface areas. The iCVD coating process is compatible with a variety of organic and inorganic materials since it does not depend on evenly wetting the substrate surface. Importantly, the iCVD technique eliminates wet-processing steps which can damage some electronic devices and organic membranes through the wetting or the spin-coating process often used to apply solution-based films.

It has also been observed that films produced by iCVD have a better-defined chemical structure than films made by traditional "wet" processing because there are fewer reaction pathways in the iCVD methods. Therefore, iCVD provides films with a substantially lower density of dangling bonds, i.e., unpaired electrons. When such bonds are present, the film undergoes reactions with components of the ambient atmosphere (such as water, resulting in a large number of hydroxyl groups). Therefore, non-iCVD films are more susceptible to atmospheric ageing, and degradation of their optical, electrical and chemical properties.

In addition, by using controlled radical polymerization chemistries, iCVD produces exceptionally clean polymers with stoichiometric compositions, high molecular weights and having no residual solvents, excipients, glidants or plasticizers. Moreover, because the substrates to be coated may remain at room temperature, iCVD is a suitable method for coating a wide variety of substrates, especially those that are susceptible to thermal degradation.

iCVD generally takes place in a reactor. The surface to be coated is placed on a stage in the reactor and gaseous precursor molecules are fed into the reactor; the stage may be the bottom of the reactor and not a separate entity.

The iCVD coating process can take place at a range of pressures from atmospheric pressure to low vacuum. In certain embodiments, a low operating pressure, typically in the range of about 10 Pa to about 100 Pa, can provide an ideal environment for the coating extremely fine objects. In certain embodiments, the pressure is less than about 1 torr; in yet other embodiments the pressure is less than about 0.7 torr or less than about 0.4 torr. In other embodiments the pressure is about 1 torr; or about 0.7 torr; or about 0.4 torr.

The flow rate of the monomer can be adjusted in the iCVD method. In certain embodiments the monomer flow rate is about 10 sccm. In other embodiments the flow rate is less than about 10 sccm. In certain embodiments the monomer flow rate is about 5 sccm. In other embodiments the flow rate is less than about 5 sccm. In certain embodiments the monomer flow rate is about 3 sccm. In other embodiments the flow rate is less than about 3 sccm. In certain embodiments the monomer flow rate is about 1.5 sccm. In other embodiments the flow rate is less than about 1.5 sccm. In certain embodiments the monomer flow rate is about 0.75 sccm. In other embodiments the flow rate is less than about 0.75 sccm. When more than one monomer is used (i.e. to deposit co-polymers), the flow rate of the additional monomers, in certain embodiments, may be the same as those presented above.

The flow rate of the initiator can be adjusted in the iCVD method. In certain embodiments the initiator flow rate is about 10 sccm. In other embodiments the flow rate is less than about 10 sccm. In certain embodiments the initiator flow rate is about 5 sccm. In other embodiments the flow rate is less than about 5 sccm. In certain embodiments the initiator flow rate is about 3 sccm. In other embodiments the flow rate is less than about 3 sccm. In certain embodiments the initiator flow rate is about 1.5 sccm. In other embodiments the flow rate is less than about 1.5 sccm. In certain embodiments the initiator flow rate is about 0.75 sccm. In other embodiments the flow rate is less than about 0.75 sccm.

The temperature of the filament can be adjusted in the iCVD method. In certain embodiments the temperature of the filament is about 350° C. In certain embodiments the temperature of the filament is about 300° C. In certain embodiments the temperature of the filament is about 250° C. In certain embodiments the temperature of the filament is about 245° C. In certain embodiments the temperature of the filament is about 235° C. In certain embodiments the temperature of the filament is about 225° C. In certain embodiments the temperature of the filament is about 200° C. In certain embodiments the temperature of the filament is about 150° C. In certain embodiments the temperature of the filament is about 100° C.

The iCVD coating process can take place at a range of temperatures. In certain embodiments the temperature is ambient temperature. In certain embodiments the temperature is about 25° C.; in yet other embodiments the temperature is between about 25° C. and 100° C., or between about 0° C. and 25° C. In certain embodiments said temperature is controlled by a water bath.

In certain embodiments, the rate of polymer deposition is about 1 micron/minute. In certain embodiments, the rate of polymer deposition is between about 1 micron/minute and about 50 nm/minute. In certain embodiments, the rate of polymer deposition is between about 10 micron/minute and about 50 nm/minute. In certain embodiments, the rate of polymer deposition is between about 100 micron/minute and about 50 nm/minute. In certain embodiments, the rate of polymer deposition is between about 1 nm/minute and about 50 nm/minute. In certain embodiments, the rate of polymer deposition is between about 10 nm/minute and about 50 nm/minute. In certain embodiments, the rate of polymer deposition is between about 10 nm/minute and about 25 nm/minute.

In certain embodiments, the gaseous initiator of the instant invention is selected from the group consisting of compounds of formula A-X-B; wherein, independently for each occurrence, A is hydrogen, alkyl, cycloalkyl, aryl, heteroaryl, aralkyl or heteroaralkyl; X is —O—O— or —N═N—; and B is hydrogen, alkyl, cycloalkyl, aryl, heteroaryl, aralkyl or heteroaralkyl.

In certain embodiments, the gaseous initiator of the instant invention is a compound of formula A-X-B, wherein A is alkyl. In certain embodiments, the gaseous initiator of the instant invention is a compound of formula A-X-B, wherein B is hydrogen or alkyl. In certain embodiments, the gaseous initiator of the instant invention is a compound of formula A-X-B, wherein A is hydrogen. In certain embodiments, the gaseous initiator of the instant invention is a compound of formula A-X-B, wherein B is alkyl. In certain embodiments, the gaseous initiator of the instant invention is a compound of formula A-X-B, wherein X is —O—O—. In certain embodiments, the gaseous initiator of the instant invention is a compound of formula A-X-B, wherein X is —N═N—. In certain embodiments, the gaseous initiator of the instant invention is a compound of formula A-X-B, wherein A is —C(CH$_3$)$_3$; and B is —C(CH$_3$)$_3$. In certain embodiments, the gaseous initiator of the instant invention is a compound of formula A-X-B, wherein A is —C(CH$_3$)$_3$; X is —O—O—; and B is —C(CH$_3$)$_3$.

In certain embodiments, the gaseous initiator is selected from the group consisting of hydrogen peroxide, alkyl or aryl peroxides (e.g., tert-butyl peroxide), hydroperoxides, halogens and nonoxidizing initiators, such as azo compounds (e.g., bis(1,1-dimethyl)diazene). Note that "gaseous" initiator encompasses initiators which may be liquids or solids at STP, but upon heating may be vaporized and fed into the chemical vapor deposition reactor.

In certain embodiments, the microcantilevers of the invention have an ultrathin polymer coating on their top surface. By "ultrathin" it is meant that the average thickness of the coating is between about 0.1 nm and about 300 nm. In certain embodiments the average thickness of the coating is between about 25 nm and 200 nm. In certain embodiments, the average thickness of the coating is between about 50 nm and about 150 nm.

In certain embodiments, the ultrathin coating is conformal. By "conformal" it is meant that the thickness of the coating is relatively uniform across the surface. In certain embodiments, the thickness of the polymer coating does not vary by more than about 10% over the top surface. In certain embodiments, the thickness of the polymer coating does not vary by more than about 5% over the top surface. In certain embodiments, the thickness of the polymer coating does not vary by more than about 1% over the top surface.

In certain embodiments, the thickness of the polymer coating on the top surface has a mass per surface area of between about 0.1 µg/cm$^2$ to about 500 µg/cm$^2$. In certain embodiments, the thickness of the polymer coating on the top surface has a mass per surface area of between about 0.1 µg/cm$^2$ to about 100 µg/cm$^2$. In certain embodiments, the thickness of the polymer coating on the top surface has a mass per surface area of between about 0.1 µg/cm$^2$ to about 50 µg/cm$^2$. In certain embodiments, the thickness of the polymer coating on the top surface has a mass per surface area of between about 0.1 µg/cm$^2$ to about 10 µg/cm$^2$. In certain embodiments, the thickness of the polymer coating on the top surface has a mass per surface area of between about 0.1 µg/cm$^2$ to about 5 µg/cm$^2$.

In certain embodiments, the polymer or co-polymer coating comprises one or more polymerized monomers selected from the group consisting of $H_2C=C(R)X$, $H_2C=C(R)C(=O)X$, $H_2C=C(R)C(=O)OX$, $H_2C=C(R)C(=O)N(R^1)X$, $H_2C=C(R)C(=O)SX$, $H_2C=C(R)OC(=O)X$, $H_2C=C(R)N(R^1)C(=O)X$, $H_2C=C(R)SC(=O)X$, $H_2C=C(R)OX$, $H_2C=C(R)N(R^1)X$, $H_2C=C(R)SX$, $H_2C=C(R)S(=O)X$, and $H_2C=C(R)S(=O)_2X$;

wherein, independently for each occurrence:

X is selected from the group consisting of hydrogen, alkyl, cycloalkyl, heteocycloalkyl, aryl, heteroaryl, aralkyl, heteoaralkyl, and $—(CH_2)_nY$;

R is selected from the group consisting of hydrogen and alkyl;

$R^1$ is selected from the group consisting of hydrogen, alkyl, aralkyl, heteroaralkyl, and carboxyl; or $R^1$ taken together with X and the nitrogen to which they are bound, are $—CH_2CH_2CH_2—$ or $—CH_2CH_2CH_2CH_2—$;

Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido;

and n is 1-10 inclusive.

In certain embodiments, the polymer or co-polymer coating on the top surface comprises one or more recurring monomeric units selected from the group consisting of maleic anhydride, N-vinyl-2-pyrrolidone, p-bromophenyl methacrylate, pentabromophenyl methacrylate, N-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorostyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, benzyl acrylate, 2-hydroxyethyl acrylate, dimethylaminoethyl acrylate, $Et_3DMAA$ (N,N-dimethylacetoacetamide), sec-butyl acrylate, tert-butyl acrylate, isobornyl acrylate, ethylene glycol diacrylate, methyl methacrylate, ethyl methacrylate, n-propyl methacrylate, n-butyl methacrylate, isobutyl methacrylate, n-pentyl methacrylate, n-hexyl methacrylate, n-heptyl methacrylate, sec-butyl methacrylate, tert-amyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, ortho-methyl styrene, meta-methyl styrene, para-methyl styrene, para-ethyl styrene, 2,4-dimethyl styrene, 2,5-dimethyl styrene, m-divinylbenzene, p-divinylbenzene, vinylimidazole, 1,4-divinyloxybutane, diethylene glygol divinyl ether, 1,5-hexadiene-3,4-diol, methyl trans-cinnamate, N-morpholinoethyl acrylate, 2-morpholinoethyl methacrylate, 2-isocyanatoethyl methacrylate, 2-sulfoethyl methacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino) ethyl methacrylate, 2-bromoethyl methacrylate, 2-phenylethyl methacrylate and 4-vinylpyridine.

In certain embodiments the polymer or co-polymer coatings are crosslinked. A suitable crosslinker is a low molecular weight di- or polyvinylic crosslinking agent such as di(ethylene glycol) di(vinyl ether), ethyleneglycol diacrylate or dimethacrylate, di-, tri- or tetraethylen-glycol diacrylate or dimethacrylate, allyl acrylate or methacrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol diacrylate or dimethacrylate, methylene bisacrylamide or methylene bismethacrylamide, ethylene bisacrylamide or ethylene bismethacrylamide, and triallyl phthalate or diallyl phthalate.

In some of the sensors described herein, maleic anhydride (Ma) is used. For previous iCVD depositions of maleic anhydride see: W. E. Tenhaeff and K. K. Gleason, "Initiated chemical vapor deposition of alternating copolymers of styrene and maleic anhydride," *Langmuir*, vol. 23, pp. 6624-6630, June 2007.

When maleic anhydride is used, the reactivity of the anhydride functionality enables the detection of amines, such as hexylamine. Detection of amines is important for industrial and environmental monitoring, food quality control, and diagnosis of certain diseases [T. Gao, E. S. Tillman, and N. S. Lewis, "Detection and classification of volatile organic amines and carboxylic acids using arrays of carbon black-dendrimer composite vapor detectors," *Chemistry of Materials*, vol. 17, pp. 2904-2911, May 2005]. In addition, low concentrations of aliphatic and aromatic amines can cause toxicological responses [K. I. Oberg, R. Hodyss, and J. L. Beauchamp, "Simple optical sensor for amine vapors based on dyed silica microspheres," *Sensors and Actuators B-Chemical*, vol. 115, pp. 79-85, May 2006].

In certain embodiments, after laying down a polymer coating on a device, the coating can be further functionalized. For example, after depositing a polymer comprising maleic anhydride, the polymer coating can be reacted with nucleophiles which will then be covalently bound to the polymer. These nucleophiles can be selected so that the resulting polymer-bound pendant moieties react are able to react selectively with different analytes. In certain embodiments, different nucleophiles can be used to sense different analytes. For instance, see Example 8 below.

Selected Device Embodiments and Methods of Use Thereof

One aspect of the invention relates to an apparatus comprising: a microcantilever element having a top surface and a bottom surface; and a substrate element positioned under the microcantilever element with a gap therebetween; wherein the substrate element comprises nano- or microfabricated conductive lines having at least two electrical leads; the top surface of the microcantilever element is coated with a polymer having a thickness of between about 0.1 nm and about 300 nm; and the bottom surface of the microcantilever element is electrically conductive, or coated with an electrically conductive material.

In certain embodiments, the invention relates to any one of the aforementioned apparatuses, further comprising a spacer between the microcantilever element and the substrate element; wherein the spacer maintains the gap between the microcantilever element and the substrate element.

In certain embodiments, the invention relates to any one of the aforementioned apparatuses, wherein the nano- or microfabricated conductive lines comprise a conductive material selected from a group consisting of silver, copper, gold, aluminum, iron, steel, brass, bronze, rhodium, iridium, platinum, titanium, mercury, graphite, or alloys thereof.

In certain embodiments, the invention relates to any one of the aforementioned apparatuses, wherein the nano- or microfabricated conductive lines form a closed circuit.

In certain embodiments, the invention relates to any one of the aforementioned apparatuses, wherein the nano- or microfabricated conductive lines form a open circuit.

In certain embodiments, the invention relates to any one of the aforementioned apparatuses, wherein the nano- or microfabricated conductive lines comprise gold.

In certain embodiments, the invention relates to any one of the aforementioned apparatuses, wherein the nano- or microfabricated conductive lines are interdigitated.

In certain embodiments, the invention relates to any one of the aforementioned apparatuses, further comprising a micro-battery connected to one of the electrical leads.

In certain embodiments, the invention relates to any one of the aforementioned apparatuses, further comprising reporting circuitry connected to one of the electrical leads.

In certain embodiments, the invention relates to any one of the aforementioned apparatuses, further comprising an RF transmitter connected to one of the electrical leads.

In certain embodiments, the invention relates to any one of the aforementioned apparatuses, wherein the polymer is a polymer or co-polymer comprising one or more of the monomers selected from the group consisting of $H_2C=C(R)X$, $H_2C=C(R)C(=O)X$, $H_2C=C(R)C(=O)OX$, $H_2C=C(R)C(=O)N(R^1)X$, $H_2C=C(R)C(=O)SX$, $H_2C=C(R)OC(=O)X$, $H_2C=C(R)N(R^1)C(=O)X$, $H_2C=C(R)SC(=O)X$, $H_2C=C(R)OX$, $H_2C=C(R)N(R^1)X$, $H_2C=C(R)SX$, $H_2C=C(R)S(=O)X$, and $H_2C=C(R)S(=O)_2X$;

wherein, independently for each occurrence:

X is selected from the group consisting of hydrogen, alkyl, cycloalkyl, heteocycloalkyl, aryl, heteroaryl, aralkyl, heteoaralkyl, and $-(CH_2)_nY$;

R is selected from the group consisting of hydrogen and alkyl;

$R^1$ is selected from the group consisting of hydrogen, alkyl, aralkyl, heteroaralkyl, and carboxyl; or $R^1$ taken together with X and the nitrogen to which they are bound, are $-CH_2CH_2CH_2-$ or $-CH_2CH_2CH_2CH_2-$;

Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido;

and n is 1-10 inclusive.

In certain embodiments, the invention relates to any one of the aforementioned apparatuses, wherein the polymer is a polymer or co-polymer comprising one or more of the monomers selected from the group consisting of maleic anhydride, N-vinyl-2-pyrrolidone, p-bromophenyl methacrylate, pentabromophenyl methacrylate, N-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorostyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, benzyl acrylate, 2-hydroxyethyl acrylate, dimethylaminoethyl acrylate, Et₃DMAA (N,N-dimethylacetoacetamide), sec-butyl acrylate, tert-butyl acrylate, isobornyl acrylate, ethylene glycol diacrylate, methyl methacrylate, ethyl methacrylate, n-propyl methacrylate, n-butyl methacrylate, isobutyl methacrylate, n-pentyl methacrylate, n-hexyl methacrylate, n-heptyl methacrylate, sec-butyl methacrylate, tert-amyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, ortho-methyl styrene, meta-methyl styrene, para-methyl styrene, para-ethyl styrene, 2,4-dimethyl styrene, 2,5-dimethyl styrene, m-divinylbenzene, p-divinylbenzene, vinylimidazole, 1,4-divinyloxybutane, diethylene glygol divinyl ether, 1,5-hexadiene-3,4-diol, methyl trans-cinnamate, N-morpholinoethyl acrylate, 2-morpholinoethyl methacrylate, 2-isocyanatoethyl methacrylate, 2-sulfoethyl methacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino) ethyl methacrylate, 2-bromoethyl methacrylate, 2-phenylethyl methacrylate and 4-vinylpyridine.

In certain embodiments, the invention relates to any one of the aforementioned apparatuses, wherein the polymer is a polymer or co-polymer of one or more of the monomers selected from the group consisting of maleic anhydride, N-vinyl-2-pyrrolidone and 4-vinylpyridine.

In certain embodiments, the invention relates to any one of the aforementioned apparatuses, wherein the polymer is a polymer or co-polymer comprising the monomer 4-vinylpyridine.

In certain embodiments, the invention relates to any one of the aforementioned apparatuses, wherein the polymer comprises pendant tryptophan, histidine, β-cyclodextrins, hexafluoropropan-2-ol, or imidazole functional groups.

In certain embodiments, the invention relates to any one of the aforementioned apparatuses, wherein the polymer comprises a crosslinker.

In certain embodiments, the invention relates to any one of the aforementioned apparatuses, wherein the polymer comprises a crosslinker selected from the group consisting of di(ethylene glycol) di(vinyl ether), ethyleneglycol diacrylate or dimethacrylate, di-, tri- or tetraethylen-glycol diacrylate or dimethacrylate, allyl acrylate or methacrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol diacrylate or dimethacrylate, methylene bisacrylamide or methylene bismethacrylamide, ethylene bisacrylamide or ethylene bismethacrylamide, and triallyl phthalate or diallyl phthalate.

In certain embodiments, the invention relates to any one of the aforementioned apparatuses, wherein the polymer comprises a crosslinker; and the crosslinker is di(ethylene glycol) di(vinyl ether).

In certain embodiments, the invention relates to any one of the aforementioned apparatuses, wherein the microcantilever element comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

In certain embodiments, the invention relates to any one of the aforementioned apparatuses, wherein the substrate element comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

In certain embodiments, the invention relates to any one of the aforementioned apparatuses, wherein the bottom surface is coated with a conductive metal.

In certain embodiments, the invention relates to any one of the aforementioned apparatuses, wherein the bottom surface is coated with gold.

In certain embodiments, the invention relates to any one of the aforementioned apparatuses, wherein the thickness of the polymer is between about 50 nm and 250 nm.

In certain embodiments, the invention relates to any one of the aforementioned apparatuses, wherein the thickness of the polymer is between about 100 nm and about 200 nm.

In certain embodiments, the invention relates to any one of the aforementioned apparatuses, wherein the top surface is coated with a compound to aid in the binding of polymer to the top surface.

In certain embodiments, the invention relates to any one of the aforementioned apparatuses, wherein the compound is an aminoalkyl silane.

In certain embodiments, the invention relates to any one of the aforementioned apparatuses, wherein the compound is 3-aminopropyldimethylethoxysilane.

In certain embodiments, the invention relates to any one of the aforementioned apparatuses, wherein the apparatus comprises a plurality of microcantilevers.

In certain embodiments, the invention relates to any one of the aforementioned apparatuses, wherein the plurality of microcantilevers are of differing lengths.

In certain embodiments, the invention relates to any one of the aforementioned apparatuses, wherein the top surfaces of the plurality of microcantilevers are coated with different polymers.

Another aspect of the invention relates to a method for assaying at least one analyte in a sample or an environment comprising the steps of: exposing an apparatus to the sample or environment; and detecting or measuring a change in the resistance of the apparatus; wherein the apparatus comprises a microcantilever element having a top surface and a bottom surface and a substrate positioned under the microcantilever element with a gap therebetween; the substrate comprises nano- or microfabricated conductive lines having at least two electrical leads; the top surface of the microcantilever element is coated with a polymer having a thickness of between about 0.1 nm and about 300 nm; and the bottom surface of the microcantilever element is electrically conductive, or coated with an electrically conductive material.

In certain embodiments, the invention relates to any one of the aforementioned methods, wherein in the detecting or measuring is done remotely.

In certain embodiments, the invention relates to any one of the aforementioned methods, wherein the analyte is a chemical agent or a biological agent.

In certain embodiments, the invention relates to any one of the aforementioned methods, wherein the chemical agent is an insecticide, a pesticide, a herbicide, tabun, sarin, soman, methylphosphonothioic acid, sulphur mustard, nitrogen mustard, lewisite, phosgene oximine, phosgene, diphosgene, chloropicrin, an organophosphate compound, an amine, an alcohol, TNT, PA, tetryl, RDX, PETN, or nitroglycerine.

In certain embodiments, the invention relates to any one of the aforementioned methods, wherein the apparatus further comprises a spacer between the microcantilever element and the substrate; wherein the spacer maintains the gap between the microcantilever element and the substrate.

In certain embodiments, the invention relates to any one of the aforementioned methods, wherein the nano- or microfabricated conductive lines comprise a conductive material selected from the group consisting of silver, copper, gold, aluminum, iron, steel, brass, bronze, rhodium, iridium, platinum, titanium, mercury, graphite, or alloys thereof.

In certain embodiments, the invention relates to any one of the aforementioned methods, wherein the nano- or microfabricated conductive lines form a closed circuit.

In certain embodiments, the invention relates to any one of the aforementioned methods, wherein the nano- or microfabricated conductive lines form a open circuit.

In certain embodiments, the invention relates to any one of the aforementioned methods, wherein the nano- or microfabricated conductive lines comprise gold.

In certain embodiments, the invention relates to any one of the aforementioned methods, wherein the nano- or microfabricated conductive lines are interdigitated.

In certain embodiments, the invention relates to any one of the aforementioned methods, wherein the apparatus further comprising a micro-battery connected to one of the electrical leads.

In certain embodiments, the invention relates to any one of the aforementioned methods, wherein the apparatus further comprising reporting circuitry connected to one of the electrical leads.

In certain embodiments, the invention relates to any one of the aforementioned methods, wherein the apparatus further comprising an RF transmitter connected to one of the electrical leads.

In certain embodiments, the invention relates to any one of the aforementioned methods, wherein the polymer is a polymer or co-polymer comprising one or more of the monomers selected from the group consisting of $H_2C=C(R)X$, $H_2C=C(R)C(=O)X$, $H_2C=C(R)C(=O)OX$, $H_2C=C(R)C(=O)N(R^1)X$, $H_2C=C(R)C(=O)SX$, $H_2C=C(R)OC(=O)X$, $H_2C=C(R)N(R^1)C(=O)X$, $H_2C=C(R)SC(=O)X$, $H_2C=C(R)OX$, $H_2C=C(R)N(R^1)X$, $H_2C=C(R)SX$, $H_2C=C(R)S(=O)X$, and $H_2C=C(R)S(=O)_2X$;

wherein, independently for each occurrence:

X is selected from the group consisting of hydrogen, alkyl, cycloalkyl, heteocycloalkyl, aryl, heteroaryl, aralkyl, heteoaralkyl, and $-(CH_2)_nY$;

R is selected from the group consisting of hydrogen and alkyl;

$R^1$ is selected from the group consisting of hydrogen, alkyl, aralkyl, heteroaralkyl, and carboxyl; or $R^1$ taken together with X and the nitrogen to which they are bound, are $-CH_2CH_2CH_2-$ or $-CH_2CH_2CH_2CH_2-$;

Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido;

and n is 1-10 inclusive.

In certain embodiments, the invention relates to any one of the aforementioned methods, wherein the polymer is a polymer or co-polymer comprising one or more of the monomers selected from the group consisting of maleic anhydride, N-vinyl-2-pyrrolidone, p-bromophenyl methacrylate, pentabromophenyl methacrylate, N-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorostyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, benzyl acrylate, 2-hydroxyethyl acrylate, dimethylaminoethyl acrylate, $Et_3DMAA$ (N,N-dimethylacetoacetamide), sec-butyl acrylate, tert-butyl acrylate, isobornyl acrylate, ethylene glycol diacrylate, methyl methacrylate, ethyl methacrylate, n-propyl methacrylate, n-butyl methacrylate, isobutyl methacrylate, n-pentyl methacrylate, n-hexyl methacrylate, n-heptyl methacrylate, sec-butyl methacrylate, tert-amyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, ortho-methyl styrene, meta-methyl styrene, para-methyl styrene, para-ethyl styrene, 2,4-dimethyl styrene, 2,5-dimethyl styrene, m-divinylbenzene, p-divinylbenzene, vinylimidazole, 1,4-divinyloxybutane, diethylene glygol divinyl ether, 1,5-hexadiene-3,4-diol, methyl trans-cinnamate, N-morpholinoethyl acrylate, 2-morpholinoethyl methacrylate, 2-isocyanatoethyl methacrylate, 2-sulfoethyl methacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino)ethyl methacrylate, 2-bromoethyl methacrylate, 2-phenylethyl methacrylate and 4-vinylpyridine.

In certain embodiments, the invention relates to any one of the aforementioned methods, wherein the polymer is a polymer or co-polymer of one or more of the monomers selected from the group consisting of maleic anhydride, N-vinyl-2-pyrrolidone, and 4-vinylpyridine.

In certain embodiments, the invention relates to any one of the aforementioned methods, wherein the polymer is a polymer or co-polymer comprising the monomer 4-vinylpyridine.

In certain embodiments, the invention relates to any one of the aforementioned methods, wherein the polymer comprises pendant tryptophan, histidine, β-cyclodextrins, hexafluoropropan-2-ol, or imidazole functional groups.

In certain embodiments, the invention relates to any one of the aforementioned methods, wherein the polymer comprises a crosslinker.

In certain embodiments, the invention relates to any one of the aforementioned methods, wherein the polymer comprises a crosslinker selected from the group consisting of di(ethylene glycol) di(vinyl ether), ethyleneglycol diacrylate or dimethacrylate, di-, tri- or tetraethylen-glycol diacrylate or dimethacrylate, allyl acrylate or methacrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol diacrylate or dimethacrylate, methylene bisacrylamide or methylene bismethacrylamide, ethylene bisacrylamide or ethylene bismethacrylamide, and triallyl phthalate or diallyl phthalate.

In certain embodiments, the invention relates to any one of the aforementioned methods, wherein the polymer comprises a crosslinker; and the crosslinker is di(ethylene glycol) di(vinyl ether).

In certain embodiments, the invention relates to any one of the aforementioned methods, wherein the microcantilever element comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

In certain embodiments, the invention relates to any one of the aforementioned methods, wherein the substrate comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

In certain embodiments, the invention relates to any one of the aforementioned methods, wherein the bottom surface is coated with a conductive metal.

In certain embodiments, the invention relates to any one of the aforementioned methods, wherein the bottom surface is coated with gold.

In certain embodiments, the invention relates to any one of the aforementioned methods, wherein the thickness of the polymer is between about 50 nm and 250 nm.

In certain embodiments, the invention relates to any one of the aforementioned methods, wherein the thickness of the polymer is between about 100 nm and about 200 nm.

In certain embodiments, the invention relates to any one of the aforementioned methods, wherein the top surface is coated with a compound to aid in the binding of polymer to the top surface.

In certain embodiments, the invention relates to any one of the aforementioned methods, wherein the compound is an aminoalkyl silane.

In certain embodiments, the invention relates to any one of the aforementioned methods, wherein the compound is 3-aminopropyldimethylethoxysilane.

In certain embodiments, the invention relates to any one of the aforementioned methods, wherein the apparatus comprises a plurality of microcantilevers.

In certain embodiments, the invention relates to any one of the aforementioned methods, wherein the plurality of microcantilevers are of differing lengths.

In certain embodiments, the invention relates to any one of the aforementioned methods, wherein the top surfaces of the plurality of microcantilevers are coated with different polymers.

Another aspect of the invention relates to an apparatus comprising an element whose surface is divided by a trench into a first section and a second section; wherein the trench has a first wall, a second wall and a width therebetween; the first section is coated with a first polymer having a thickness of between about 0.1 nm and about 500 nm; the second section is coated with a second polymer having a thickness of between about 0.1 nm and about 500 nm; the first wall is coated with a third polymer having a thickness of between about 0.1 nm and about 500 nm; the second wall is coated with a fourth polymer having a thickness of between about 0.1 nm and about 500 nm; and at least the first section and the second section, or at least the first wall and the second wall, further comprise a conductive material connected to at least two electrical leads.

In certain embodiments, the invention relates to any one of the aforementioned apparatuses, wherein the width of the trench is about 500 nm.

In certain embodiments, the invention relates to any one of the aforementioned apparatuses, wherein only the first section and the second section comprise a conductive material.

In certain embodiments, the invention relates to any one of the aforementioned apparatuses, wherein only the first wall and the second wall comprise a conductive material.

In certain embodiments, the invention relates to any one of the aforementioned apparatuses, wherein the conductive material comprises one or more nano- or microfabricated conductive lines.

In certain embodiments, the invention relates to any one of the aforementioned apparatuses, wherein the nano- or microfabricated conductive lines comprise a conductive material selected from a group consisting of silver, copper, gold, aluminum, iron, steel, brass, bronze, rhodium, iridium, platinum, titanium, mercury, graphite, or alloys thereof.

In certain embodiments, the invention relates to any one of the aforementioned apparatuses, wherein the nano- or microfabricated conductive lines form a closed circuit.

In certain embodiments, the invention relates to any one of the aforementioned apparatuses, wherein the nano- or microfabricated conductive lines form a open circuit.

In certain embodiments, the invention relates to any one of the aforementioned apparatuses, wherein the nano- or microfabricated conductive lines comprise gold.

In certain embodiments, the invention relates to any one of the aforementioned apparatuses, wherein the nano- or microfabricated conductive lines are interdigitated.

In certain embodiments, the invention relates to any one of the aforementioned apparatuses, further comprising a micro-battery connected to one of the electrical leads.

In certain embodiments, the invention relates to any one of the aforementioned apparatuses, further comprising reporting circuitry connected to one of the electrical leads.

In certain embodiments, the invention relates to any one of the aforementioned apparatuses, further comprising an RF transmitter connected to one of the electrical leads.

In certain embodiments, the invention relates to any one of the aforementioned apparatuses, wherein the first, second, third and fourth polymers are independently selected from polymers and co-polymers comprising one or more of the monomers selected from the group consisting of $H_2C=C(R)X$, $H_2C=C(R)C(=O)X$, $H_2C=C(R)C(=O)OX$, $H_2C=C(R)C(=O)N(R^1)X$, $H_2C=C(R)C(=O)SX$, $H_2C=C(R)OC(=O)X$, $H_2C=C(R)N(R^1)C(=O)X$, $H_2C=C(R)SC(=O)X$, $H_2C=C(R)OX$, $H_2C=C(R)N(R^1)X$, $H_2C=C(R)SX$, $H_2C=C(R)S(=O)X$, and $H_2C=C(R)S(=O)_2X$;

wherein, independently for each occurrence:

X is selected from the group consisting of hydrogen, alkyl, cycloalkyl, heteocycloalkyl, aryl, heteroaryl, aralkyl, heteoaralkyl, and $-(CH_2)_nY$;

R is selected from the group consisting of hydrogen and alkyl;

$R^1$ is selected from the group consisting of hydrogen, alkyl, aralkyl, heteroaralkyl, and carboxyl; or $R^1$ taken together with X and the nitrogen to which they are bound, are $-CH_2CH_2CH_2-$ or $-CH_2CH_2CH_2CH_2-$;

Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido;

and n is 1-10 inclusive.

In certain embodiments, the invention relates to any one of the aforementioned apparatuses, wherein the first, second, third and fourth polymers are independently selected from polymer and co-polymers comprising one or more of the monomers selected from the group consisting of maleic anhydride, N-vinyl-2-pyrrolidone, p-bromophenyl methacrylate, pentabromophenyl methacrylate, N-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorostyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, benzyl acrylate, 2-hydroxyethyl acrylate, dimethylaminoethyl acrylate, Et₃DMAA (N,N-dimethylacetoacetamide), sec-butyl acrylate, tert-butyl acrylate, isobornyl acrylate, ethylene glycol diacrylate, methyl methacrylate, ethyl methacrylate, n-propyl methacrylate, n-butyl methacrylate, isobutyl methacrylate, n-pentyl methacrylate, n-hexyl methacrylate, n-heptyl methacrylate, sec-butyl methacrylate, tert-amyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, ortho-methyl styrene, meta-methyl styrene, para-methyl styrene, para-ethyl styrene, 2,4-dimethyl styrene, 2,5-dimethyl styrene, m-divinylbenzene, p-divinylbenzene, vinylimidazole, 1,4-divinyloxybutane, diethylene glygol divinyl ether, 1,5-hexadiene-3,4-diol, methyl trans-cinnamate, N-morpholinoethyl acrylate, 2-morpholinoethyl methacrylate, 2-isocyanatoethyl methacrylate, 2-sulfoethyl methacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino) ethyl methacrylate, 2-bromoethyl methacrylate, 2-phenylethyl methacrylate and 4-vinylpyridine In certain embodiments, the invention relates to any one of the aforementioned apparatuses, wherein the first, second, third and fourth polymers are independently selected from polymers and co-polymer comprising one or more of the monomers selected from the group consisting of maleic anhydride, N-vinyl-2-pyrrolidone, and 4-vinylpyridine.

In certain embodiments, the invention relates to any one of the aforementioned apparatuses, wherein the first, second, third and fourth polymers are polymers or co-polymers comprising 4-vinylpyridine.

In certain embodiments, the invention relates to any one of the aforementioned apparatuses, wherein the first polymer, second polymer, third polymer and/or fourth polymer comprise pendant tryptophan, histidine, β-cyclodextrins, hexafluorppropan-2-ol, or imidazole functional groups.

In certain embodiments, the invention relates to any one of the aforementioned apparatuses, wherein the first polymer, second polymer, third polymer and/or fourth polymer comprises a crosslinker.

In certain embodiments, the invention relates to any one of the aforementioned apparatuses, wherein the crosslinker is selected from the group consisting of di(ethylene glycol) di(vinyl ether), ethyleneglycol diacrylate or dimethacrylate, di-, tri- or tetraethylen-glycol diacrylate or dimethacrylate, allyl acrylate or methacrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol diacrylate or dimethacrylate, methylene bisacrylamide or methylene bismethacrylamide, ethylene bisacrylamide or ethylene bismethacrylamide, and triallyl phthalate or diallyl phthalate.

In certain embodiments, the invention relates to any one of the aforementioned apparatuses, wherein the crosslinker is di(ethylene glycol) di(vinyl ether).

In certain embodiments, the invention relates to any one of the aforementioned apparatuses, wherein the element comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

In certain embodiments, the invention relates to any one of the aforementioned apparatuses, wherein the thickness of the first, second, third and/or fourth polymer is between about 50 nm and 250 nm.

In certain embodiments, the invention relates to any one of the aforementioned apparatuses, wherein the thickness of the first, second, third and/or fourth polymer is between about 100 nm and about 200 nm.

In certain embodiments, the invention relates to any one of the aforementioned apparatuses, wherein the element is coated with a compound to aid in the binding of first polymer, second polymer, third polymer and/or fourth polymer to the first section, second section, first wall and/or second wall.

In certain embodiments, the invention relates to any one of the aforementioned apparatuses, wherein the compound is an aminoalkyl silane.

In certain embodiments, the invention relates to any one of the aforementioned apparatuses, wherein the compound is 3-aminopropyldimethylethoxysilane.

Another aspect of the invention relates to a method for assaying at least one analyte in a sample or an environment comprising the steps of: exposing an apparatus to the sample or environment; and detecting or measuring a change in the resistance of the apparatus; wherein the apparatus comprises an element whose surface is divided by a trench into a first section and a second section; the trench has a first wall, a second wall and a width therebetween; the first section is coated with a first polymer having a thickness of between about 0.1 nm and about 500 nm; the second section is coated with a second polymer having a thickness of between about 0.1 nm and about 500 nm; the first wall is coated with a third polymer having a thickness of between about 0.1 nm and about 500 nm; the second wall is coated with a fourth polymer having a thickness of between about 0.1 nm and about 500 nm; and at least the first section and the second section, or at least the first wall and the second wall, further comprise a conductive material connected to at least two electrical leads.

In certain embodiments, the invention relates to any one of the aforementioned methods, wherein in the detecting or measuring is done remotely.

In certain embodiments, the invention relates to any one of the aforementioned methods, wherein the analyte is a chemical agent or a biological agent.

In certain embodiments, the invention relates to any one of the aforementioned methods, wherein the chemical agent is an insecticide, a pesticide, a herbicide, tabun, sarin, soman, methylphosphonothioic acid, sulphur mustard, nitrogen mustard, lewisite, phosgene oximine, phosgene, diphosgene, chloropicrin, an organophosphate compound, an amine, an alcohol, TNT, PA, tetryl, RDX, PETN, or nitroglycerine.

In certain embodiments, the invention relates to any one of the aforementioned methods, wherein the width of the trench is about 500 nm.

In certain embodiments, the invention relates to any one of the aforementioned methods, wherein only the first section and the second section comprise a conductive material.

In certain embodiments, the invention relates to any one of the aforementioned methods, wherein only the first wall and the second wall comprise a conductive material.

In certain embodiments, the invention relates to any one of the aforementioned methods, wherein the conductive material comprises one or more nano- or microfabricated conductive lines.

In certain embodiments, the invention relates to any one of the aforementioned methods, wherein the nano- or microfabricated conductive lines comprise a conductive material selected from a group consisting of silver, copper, gold, aluminum, iron, steel, brass, bronze, rhodium, iridium, platinum, titanium, mercury, graphite, or alloys thereof.

In certain embodiments, the invention relates to any one of the aforementioned methods, wherein the nano- or microfabricated conductive lines form a closed circuit.

In certain embodiments, the invention relates to any one of the aforementioned methods, wherein the nano- or microfabricated conductive lines form a open circuit.

In certain embodiments, the invention relates to any one of the aforementioned methods, wherein the nano- or micro-fabricated conductive lines comprise gold.

In certain embodiments, the invention relates to any one of the aforementioned methods, wherein the nano- or micro-fabricated conductive lines are interdigitated.

In certain embodiments, the invention relates to any one of the aforementioned methods, further comprising a microbattery connected to one of the electrical leads.

In certain embodiments, the invention relates to any one of the aforementioned methods, further comprising reporting circuitry connected to one of the electrical leads.

In certain embodiments, the invention relates to any one of the aforementioned methods, further comprising an RF transmitter connected to one of the electrical leads.

In certain embodiments, the invention relates to any one of the aforementioned methods, wherein the first, second, third and fourth polymers are independently selected from polymers and co-polymers comprising one or more of the monomers selected from the group consisting of $H_2C=C(R)X$, $H_2C=C(R)C(=O)X$, $H_2C=C(R)C(=O)OX$, $H_2C=C(R)C(=O)N(R^1)X$, $H_2C=C(R)C(=O)SX$, $H_2C=C(R)OC(=O)X$, $H_2C=C(R)N(R^1)C(=O)X$, $H_2C=C(R)SC(=O)X$, $H_2C=C(R)OX$, $H_2C=C(R)N(R^1)X$, $H_2C=C(R)SX$, $H_2C=C(R)S(=O)X$, and $H_2C=C(R)S(=O)_2X$;

wherein, independently for each occurrence:

X is selected from the group consisting of hydrogen, alkyl, cycloalkyl, heteocycloalkyl, aryl, heteroaryl, aralkyl, heteoaralkyl, and $—(CH_2)_nY$;

R is selected from the group consisting of hydrogen and alkyl;

$R^1$ is selected from the group consisting of hydrogen, alkyl, aralkyl, heteroaralkyl, and carboxyl; or $R^1$ taken together with X and the nitrogen to which they are bound, are $—CH_2CH_2CH_2—$ or $—CH_2CH_2CH_2CH_2—$;

Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido;

and n is 1-10 inclusive.

In certain embodiments, the invention relates to any one of the aforementioned methods, wherein the first, second, third and fourth polymers are independently selected from micropolymer and co-polymers comprising one or more of the monomers selected from the group consisting of maleic anhydride, N-vinyl-2-pyrrolidone, p-bromophenyl methacrylate, pentabromophenyl methacrylate, N-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorostyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, benzyl acrylate, 2-hydroxyethyl acrylate, dimethylaminoethyl acrylate, $Et_3DMAA$ (N,N-dimethylacetoacetamide), sec-butyl acrylate, tert-butyl acrylate, isobornyl acrylate, ethylene glycol diacrylate, methyl methacrylate, ethyl methacrylate, n-propyl methacrylate, n-butyl methacrylate, isobutyl methacrylate, n-pentyl methacrylate, n-hexyl methacrylate, n-heptyl methacrylate, sec-butyl methacrylate, tert-amyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, ortho-methyl styrene, meta-methyl styrene, para-methyl styrene, para-ethyl styrene, 2,4-dimethyl styrene, 2,5-dimethyl styrene, m-divinylbenzene, p-divinylbenzene, vinylimidazole, 1,4-divinyloxybutane, diethylene glygol divinyl ether, 1,5-hexadiene-3,4-diol, methyl trans-cinnamate, N-morpholinoethyl acrylate, 2-morpholinoethyl methacrylate, 2-isocyanatoethyl methacrylate, 2-sulfoethyl methacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino)ethyl methacrylate, 2-bromoethyl methacrylate, 2-phenylethyl methacrylate and 4-vinylpyridine.

In certain embodiments, the invention relates to any one of the aforementioned methods, wherein the first, second, third and fourth polymers are independently selected from polymers and co-polymer comprising one or more of the monomers selected from the group consisting of maleic anhydride, N-vinyl-2-pyrrolidone, and 4-vinylpyridine.

In certain embodiments, the invention relates to any one of the aforementioned methods, wherein the first, second, third and fourth polymers are polymers or co-polymers comprising the monomer 4-vinylpyridine.

In certain embodiments, the invention relates to any one of the aforementioned methods, wherein the first polymer, second polymer, third polymer and/or fourth polymer comprise pendant tryptophan, histidine, β-cyclodextrins, hexafluoropropan-2-ol, or imidazole functional groups.

In certain embodiments, the invention relates to any one of the aforementioned methods, wherein the first polymer, second polymer, third polymer and/or fourth polymer comprises a crosslinker.

In certain embodiments, the invention relates to any one of the aforementioned methods, wherein the crosslinker is selected from the group consisting of di(ethylene glycol) di(vinyl ether), ethyleneglycol diacrylate or dimethacrylate, di-, tri- or tetraethylen-glycol diacrylate or dimethacrylate, allyl acrylate or methacrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol diacrylate or dimethacrylate, methylene bisacrylamide or methylene bismethacrylamide, ethylene bisacrylamide or ethylene bismethacrylamide, and triallyl phthalate or diallyl phthalate.

In certain embodiments, the invention relates to any one of the aforementioned methods, wherein the crosslinker is di(ethylene glycol) di(vinyl ether).

In certain embodiments, the invention relates to any one of the aforementioned methods, wherein the element comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

In certain embodiments, the invention relates to any one of the aforementioned methods, wherein the thickness of the first, second, third and/or fourth polymer is between about 50 nm and 250 nm.

In certain embodiments, the invention relates to any one of the aforementioned methods, wherein the thickness of the first, second, third and/or fourth polymer is between about 100 nm and about 200 nm.

In certain embodiments, the invention relates to any one of the aforementioned methods, wherein the element is coated with a compound to aid in the binding of first polymer, second polymer, third polymer and/or fourth polymer to the first section, second section, first wall and/or second wall.

In certain embodiments, the invention relates to any one of the aforementioned methods, wherein the compound is an aminoalkyl silane.

In certain embodiments, the invention relates to any one of the aforementioned methods, wherein the compound is 3-aminopropyldimethylethoxysilane.

Another aspect of the invention relates to an apparatus comprising: a first element having a top and bottom; and a second element having a top and bottom; wherein the bottom of the first element is positioned facing the top of the second element with a gap therebetween; the bottom of the first element is coated with a polymer having a thickness of between about 0.1 µm and about 500 µm; the polymer is electrically conducting or is coated with an electrically conductive material; and the top of the second element is electrically insulating and comprises on its surface non-contiguous electrically conducting material connected to at least two electrical leads.

In certain embodiments, the invention relates to any one of the aforementioned apparatuses, wherein the width of the gap is between about 0.1 µm and about 10 µm.

In certain embodiments, the invention relates to any one of the aforementioned apparatuses, wherein the non-contiguous electrically conducting material comprises one or more nano- or microfabricated conductive lines.

In certain embodiments, the invention relates to any one of the aforementioned apparatuses, wherein the nano- or microfabricated conductive lines comprise a conductive material selected from a group consisting of silver, copper, gold, aluminum, iron, steel, brass, bronze, rhodium, iridium, platinum, titanium, mercury, graphite, or alloys thereof.

In certain embodiments, the invention relates to any one of the aforementioned apparatuses, wherein the nano- or microfabricated conductive lines form a closed circuit.

In certain embodiments, the invention relates to any one of the aforementioned apparatuses, wherein the nano- or microfabricated conductive lines form a open circuit.

In certain embodiments, the invention relates to any one of the aforementioned apparatuses, wherein the nano- or microfabricated conductive lines comprise gold.

In certain embodiments, the invention relates to any one of the aforementioned apparatuses, wherein the nano- or microfabricated conductive lines are interdigitated.

In certain embodiments, the invention relates to any one of the aforementioned apparatuses, wherein the electrically conductive material is selected from a group consisting of silver, copper, gold, aluminum, iron, steel, brass, bronze, rhodium, iridium, platinum, titanium, mercury, graphite, or alloys thereof.

In certain embodiments, the invention relates to any one of the aforementioned apparatuses, further comprising a micro-battery connected to one of the electrical leads.

In certain embodiments, the invention relates to any one of the aforementioned apparatuses, further comprising reporting circuitry connected to one of the electrical leads.

In certain embodiments, the invention relates to any one of the aforementioned apparatuses, further comprising an RF transmitter connected to one of the electrical leads.

In certain embodiments, the invention relates to any one of the aforementioned apparatuses, wherein the polymer is selected from polymers and co-polymers comprising one or more of the monomers selected from the group consisting of $H_2C=C(R)X$, $H_2C=C(R)C(=O)X$, $H_2C=C(R)C(=O)OX$, $H_2C=C(R)C(=O)N(R^1)X$, $H_2C=C(R)C(=O)SX$, $H_2C=C(R)OC(=O)X$, $H_2C=C(R)N(R^1)C(=O)X$, $H_2C=C(R)SC(=O)X$, $H_2C=C(R)OX$, $H_2C=C(R)N(R^1)X$, $H_2C=C(R)SX$, $H_2C=C(R)S(=O)X$, and $H_2C=C(R)S(=O)_2X$;

wherein, independently for each occurrence:

X is selected from the group consisting of hydrogen, alkyl, cycloalkyl, heteocycloalkyl, aryl, heteroaryl, aralkyl, heteoaralkyl, and $-(CH_2)_nY$;

R is selected from the group consisting of hydrogen and alkyl;

$R^1$ is selected from the group consisting of hydrogen, alkyl, aralkyl, heteroaralkyl, and carboxyl; or $R^1$ taken together with X and the nitrogen to which they are bound, are $-CH_2CH_2CH_2-$ or $-CH_2CH_2CH_2CH_2-$;

Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido;

and n is 1-10 inclusive.

In certain embodiments, the invention relates to any one of the aforementioned apparatuses, wherein the polymer is selected from polymers and co-polymers comprising one or more of the monomers selected from the group consisting of maleic anhydride, N-vinyl-2-pyrrolidone, p-bromophenyl methacrylate, pentabromophenyl methacrylate, N-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorostyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, benzyl acrylate, 2-hydroxyethyl acrylate, dimethylaminoethyl acrylate, Et$_3$DMAA (N,N-dimethylacetoacetamide), sec-butyl acrylate, tert-butyl acrylate, isobornyl acrylate, ethylene glycol diacrylate, methyl methacrylate, ethyl methacrylate, n-propyl methacrylate, n-butyl methacrylate, isobutyl methacrylate, n-pentyl methacrylate, n-hexyl methacrylate, n-heptyl methacrylate, sec-butyl methacrylate, tert-amyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, ortho-methyl styrene, meta-methyl styrene, para-methyl styrene, para-ethyl styrene, 2,4-dimethyl styrene, 2,5-dimethyl styrene, m-divinylbenzene, p-divinylbenzene, vinylimidazole, 1,4-divinyloxybutane, diethylene glygol divinyl ether, 1,5-hexadiene-3,4-diol, methyl trans-cinnamate, N-morpholinoethyl acrylate, 2-morpholinoethyl methacrylate, 2-isocyanatoethyl methacrylate, 2-sulfoethyl methacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino) ethyl methacrylate, 2-bromoethyl methacrylate, 2-phenyl-ethyl methacrylate and 4-vinylpyridine.

In certain embodiments, the invention relates to any one of the aforementioned apparatuses, wherein the polymers are independently selected from polymers and co-polymers comprising one or more of the monomers selected from the group consisting of maleic anhydride, N-vinyl-2-pyrrolidone and 4-vinylpyridine.

In certain embodiments, the invention relates to any one of the aforementioned apparatuses, wherein the polymer is a polymer or co-polymer comprising 4-vinylpyridine.

In certain embodiments, the invention relates to any one of the aforementioned apparatuses, wherein the polymer comprises pendant tryptophan, histidine, β-cyclodextrins, hexafluoropropan-2-ol, or imidazole functional groups.

In certain embodiments, the invention relates to any one of the aforementioned apparatuses, wherein the polymer comprises a crosslinker.

In certain embodiments, the invention relates to any one of the aforementioned apparatuses, wherein the crosslinker is selected from the group consisting of di(ethylene glycol) di(vinyl ether), ethyleneglycol diacrylate or dimethacrylate, di-, tri- or tetraethylen-glycol diacrylate or dimethacrylate, allyl acrylate or methacrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol diacrylate or dimethacrylate, methylene bisacrylamide or methylene bismethacrylamide, ethylene bisacrylamide or ethylene bismethacrylamide, and triallyl phthalate or diallyl phthalate.

In certain embodiments, the invention relates to any one of the aforementioned apparatuses, wherein the crosslinker is di(ethylene glycol) di(vinyl ether).

In certain embodiments, the invention relates to any one of the aforementioned apparatuses, wherein the first element comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

In certain embodiments, the invention relates to any one of the aforementioned apparatuses, wherein the second element comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

In certain embodiments, the invention relates to any one of the aforementioned apparatuses, wherein the first element is mechanically connected to the second element.

In certain embodiments, the invention relates to any one of the aforementioned apparatuses, wherein the thickness of the polymer is between about 0.1 μm and 10 μm.

In certain embodiments, the invention relates to any one of the aforementioned apparatuses, wherein the thickness of the polymer is about 1 μm.

In certain embodiments, the invention relates to any one of the aforementioned apparatuses, wherein the first element and/or the second element is coated with a compound to aid in the binding of polymer to the first element and/or the second element.

In certain embodiments, the invention relates to any one of the aforementioned apparatuses, wherein the compound is an aminoalkyl silane.

In certain embodiments, the invention relates to any one of the aforementioned apparatuses, wherein the compound is 3-aminopropyldimethylethoxysilane.

Another aspect of the invention relates to a method for assaying at least one analyte in a sample or an environment comprising the steps of: exposing an apparatus to the sample or environment; and detecting or measuring a change in the resistance of the apparatus; wherein the apparatus comprises a first element having a top and bottom; and a second element having a top and bottom; the bottom of the first element is positioned facing the top of the second element with a gap therebetween; the bottom of the first element is coated with a polymer having a thickness of between about 0.1 μm and about 500 μm; the polymer is electrically conducting or is coated with an electrically conductive material; and the top of the second element is electrically insulating and comprises on its surface non-contiguous electrically conducting material connected to at least two electrical leads.

In certain embodiments, the invention relates to any one of the aforementioned methods, wherein in the detecting or measuring is done remotely.

In certain embodiments, the invention relates to any one of the aforementioned methods, wherein the analyte is a chemical agent or a biological agent.

In certain embodiments, the invention relates to any one of the aforementioned methods, wherein the chemical agent is an insecticide, a pesticide, a herbicide, tabun, sarin, soman, methylphosphonothioic acid, sulphur mustard, nitrogen mustard, lewisite, phosgene oximine, phosgene, diphosgene, chloropicrin, an organophosphate compound, an amine, an alcohol, TNT, PA, tetryl, RDX, PETN, or nitroglycerine.

In certain embodiments, the invention relates to any one of the aforementioned methods, wherein the width of the gap is between about 0.1 μm and about 10 μm.

In certain embodiments, the invention relates to any one of the aforementioned methods, wherein the non-contiguous electrically conducting material comprises one or more nano- or microfabricated conductive lines.

In certain embodiments, the invention relates to any one of the aforementioned methods, wherein the nano- or microfabricated conductive lines comprise a conductive material selected from a group consisting of silver, copper, gold, aluminum, iron, steel, brass, bronze, rhodium, iridium, platinum, titanium, mercury, graphite, or alloys thereof.

In certain embodiments, the invention relates to any one of the aforementioned methods, wherein the nano- or microfabricated conductive lines form a closed circuit.

In certain embodiments, the invention relates to any one of the aforementioned methods, wherein the nano- or microfabricated conductive lines form a open circuit.

In certain embodiments, the invention relates to any one of the aforementioned methods, wherein the nano- or microfabricated conductive lines comprise gold.

In certain embodiments, the invention relates to any one of the aforementioned methods, wherein the nano- or microfabricated conductive lines are interdigitated.

In certain embodiments, the invention relates to any one of the aforementioned methods, wherein the electrically conductive material is selected from a group consisting of silver, copper, gold, aluminum, iron, steel, brass, bronze, rhodium, iridium, platinum, titanium, mercury, graphite, or alloys thereof.

In certain embodiments, the invention relates to any one of the aforementioned methods, further comprising a microbattery connected to one of the electrical leads.

In certain embodiments, the invention relates to any one of the aforementioned methods, further comprising reporting circuitry connected to one of the electrical leads.

In certain embodiments, the invention relates to any one of the aforementioned methods, further comprising an RF transmitter connected to one of the electrical leads.

In certain embodiments, the invention relates to any one of the aforementioned methods, wherein the polymer is selected from polymers and co-polymers comprising one or more of the monomers selected from the group consisting of $H_2C=C(R)X$, $H_2C=C(R)C(=O)X$, $H_2C=C(R)C(=O)OX$, $H_2C=C(R)C(=O)N(R^1)X$, $H_2C=C(R)C(=O)SX$, $H_2C=C(R)OC(=O)X$, $H_2C=C(R)N(R^1)C(=O)X$, $H_2C=C(R)SC(=O)X$, $H_2C=C(R)OX$, $H_2C=C(R)N(R^1)X$, $H_2C=C(R)SX$, $H_2C=C(R)S(=O)X$, and $H_2C=C(R)S(=O)_2X$;

wherein, independently for each occurrence:

X is selected from the group consisting of hydrogen, alkyl, cycloalkyl, heteocycloalkyl, aryl, heteroaryl, aralkyl, heteoaralkyl, and —$(CH_2)_nY$;

R is selected from the group consisting of hydrogen and alkyl;

$R^1$ is selected from the group consisting of hydrogen, alkyl, aralkyl, heteroaralkyl, and carboxyl; or $R^1$ taken together with X and the nitrogen to which they are bound, are —$CH_2CH_2CH_2$— or —$CH_2CH_2CH_2CH_2$—;

Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido;

and n is 1-10 inclusive.

In certain embodiments, the invention relates to any one of the aforementioned methods, wherein the polymer is selected from polymer and co-polymers comprising one or more of the monomers selected from the group consisting of maleic anhydride, N-vinyl-2-pyrrolidone, p-bromophenyl methacrylate, pentabromophenyl methacrylate, N-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorostyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, benzyl acrylate, 2-hydroxyethyl acrylate, dimethylaminoethyl acrylate, $Et_3DMAA$ (N,N-dimethylacetoacetamide), sec-butyl acrylate, tert-butyl acrylate, isobornyl acrylate, ethylene glycol diacrylate, methyl methacrylate, ethyl methacrylate, n-propyl methacrylate, n-butyl methacrylate, isobutyl methacrylate, n-pentyl methacrylate, n-hexyl methacrylate, n-heptyl methacrylate, sec-butyl methacrylate, tert-amyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, ortho-methyl styrene, meta-methyl styrene, para-methyl styrene, para-ethyl styrene, 2,4-dimethyl styrene, 2,5-dimethyl styrene, m-divinylbenzene, p-divinylbenzene, vinylimidazole, 1,4-divinyloxybutane, diethylene glygol divinyl ether, 1,5-hexadiene-3,4-diol, methyl trans-cinnamate, N-morpholinoethyl acrylate, 2-morpholinoethyl methacrylate, 2-isocyanatoethyl methacrylate, 2-sulfoethyl methacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino) ethyl methacrylate, 2-bromoethyl methacrylate, 2-phenylethyl methacrylate and 4-vinylpyridine.

In certain embodiments, the invention relates to any one of the aforementioned methods, wherein the polymer is independently selected from polymer or co-polymer comprising one or more of the monomers selected from the group consisting of maleic anhydride and N-vinyl-2-pyrrolidone, and 4-vinylpyridine.

In certain embodiments, the invention relates to any one of the aforementioned methods, wherein the polymer is independently selected from polymer or co-polymer comprising 4-vinylpyridine.

In certain embodiments, the invention relates to any one of the aforementioned methods, wherein the polymer comprises pendant tryptophan, histidine, β-cyclodextrins, hexafluoropropan-2-ol, or imidazole functional groups.

In certain embodiments, the invention relates to any one of the aforementioned methods, wherein the polymer comprises a crosslinker.

In certain embodiments, the invention relates to any one of the aforementioned methods, wherein the crosslinker is selected from the group consisting of di(ethylene glycol) di(vinyl ether), ethyleneglycol diacrylate or dimethacrylate, di-, tri- or tetraethylen-glycol diacrylate or dimethacrylate, allyl acrylate or methacrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol diacrylate or dimethacrylate, methylene bisacrylamide or methylene bismethacrylamide, ethylene bisacrylamide or ethylene bismethacrylamide, and triallyl phthalate or diallyl phthalate.

In certain embodiments, the invention relates to any one of the aforementioned methods, wherein the crosslinker is di(ethylene glycol) di(vinyl ether).

In certain embodiments, the invention relates to any one of the aforementioned methods, wherein the first element comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

In certain embodiments, the invention relates to any one of the aforementioned methods, wherein the second element comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

In certain embodiments, the invention relates to any one of the aforementioned methods, wherein the first element is mechanically connected to the second element.

In certain embodiments, the invention relates to any one of the aforementioned methods, wherein the thickness of the polymer is between about 0.1 μm and 10 μm.

In certain embodiments, the invention relates to any one of the aforementioned methods, wherein the thickness of the polymer is about 1 μm.

In certain embodiments, the invention relates to any one of the aforementioned methods, wherein the first element and/or the second element is coated with a compound to aid in the binding of polymer to the first element and/or the second element.

In certain embodiments, the invention relates to any one of the aforementioned methods, wherein the compound is an aminoalkyl silane.

In certain embodiments, the invention relates to any one of the aforementioned methods, wherein the compound is 3-aminopropyldimethylethoxysilane.

Definitions

For convenience, definitions of certain terms employed in the specification, examples, and appended claims are collected here.

As used herein, the term "polymer" means a molecule, formed by the chemical union of two or more oligomer units. The oligomer units are normally linked together by covalent linkages. The two or more combining units in a polymer can be all the same, in which case the polymer is referred to as a homopolymer. They can be also be different and, thus, the polymer will be a combination of the different units. These polymers are referred to as copolymers. In certain embodiments, the polymer coating is a block copolymer, random copolymer, graft polymer, or branched copolymer.

The phrase "weight average molecular weight" refers to a particular measure of the molecular weight of a polymer. The weight average molecular weight is calculated as follows: determine the molecular weight of a number of polymer molecules; add the squares of these weights; and then divide by the total weight of the molecules.

The phrase "number average molecular weight" refers to a particular measure of the molecular weight of a polymer. The number average molecular weight is the common average of the molecular weights of the individual polymer molecules. It is determined by measuring the molecular weight of n polymer molecules, summing the weights, and dividing by n.

The phrase "polydispersity index" refers to the ratio of the "weight average molecular weight" to the "number average molecular weight" for a particular polymer; it reflects the distribution of individual molecular weights in a polymer sample.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho (o-), meta (m-) and para (p-) are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF₃, —CN, or the like.

The term "carbocycle" is art-recognized and refers to an aromatic or non-aromatic ring in which each atom of the ring is carbon.

The term "nitro" is art-recognized and refers to —NO₂; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO₂⁻. "Halide" designates the corresponding anion of the halogens, and "pseudohalide" has the definition set forth on page 560 of "Advanced Inorganic Chemistry" by Cotton and Wilkinson.

The terms "amine" and "amino" are art-recognized and refer to both unsubstituted and substituted amines, e.g., a moiety that may be represented by the general formulas:

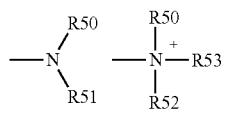

wherein R50, R51, R52 and R53 each independently represent a hydrogen, an alkyl, an alkenyl, —(CH₂)ₘ—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH₂)ₘ—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

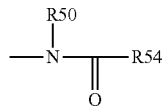

wherein R50 is as defined above, and R54 represents a hydrogen, an alkyl, an alkenyl or —(CH₂)ₘ—R61, where m and R61 are as defined above.

The term "amido" is art recognized as an amino-substituted carbonyl and includes a moiety that may be represented by the general formula:

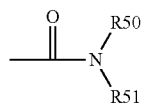

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH₂)ₘ—R61, wherein m and R61 are defined above. Representative alkylthio groups include methylthio, ethyl thio, and the like.

The term "carboxyl" is art recognized and includes such moieties as may be represented by the general formulas:

wherein X50 is a bond or represents an oxygen or a sulfur, and R55 and R56 represents a hydrogen, an alkyl, an alkenyl, —(CH₂)ₘ—R61 or a pharmaceutically acceptable salt, R56 represents a hydrogen, an alkyl, an alkenyl or —(CH₂)ₘ—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

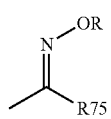

wherein R75 is hydrogen, alkyl, cycloalkyl, alkenyl, alkynyl, aryl, aralkyl, or —(CH₂)ₘ—R61. The moiety is an "oxime" when R is H; and it is an "oxime ether" when R is alkyl, cycloalkyl, alkenyl, alkynyl, aryl, aralkyl, or —(CH₂)ₘ—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH₂)ₘ—R61, where m and R61 are described above.

The term "sulfonate" is art recognized and refers to a moiety that may be represented by the general formula:

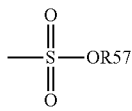

in which R57 is an electron pair, hydrogen, alkyl, cycloalkyl, or aryl.

The term "sulfate" is art recognized and includes a moiety that may be represented by the general formula:

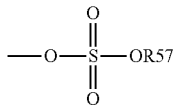

in which R57 is as defined above.

The term "sulfonamido" is art recognized and includes a moiety that may be represented by the general formula:

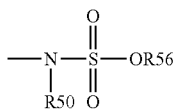

in which R50 and R56 are as defined above.

The term "sulfamoyl" is art-recognized and refers to a moiety that may be represented by the general formula:

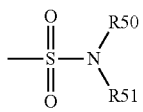

in which R50 and R51 are as defined above.

The term "sulfonyl" is art-recognized and refers to a moiety that may be represented by the general formula:

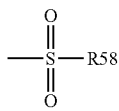

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

EXEMPLIFICATION

The invention now being generally described, it will be more readily understood by reference to the following examples, which are included merely for purposes of illustration of certain aspects and embodiments of the present invention, and are not intended to limit the invention.

Example 1

Device Fabrication

Silicon nitride membranes windows (1 mm×1 mm, 100 nm thick) are formed by backside TMAH etching of silicon. Photoresist is spun directly onto the membrane, exposed with cantilever shapes using a contact mask and developed. The membrane is etched with a $CF_4$ reactive ion etch (100 V, 200 W, 10 mTorr) until the cantilever border is completely etched. The sample is cleaned in an oxygen plasma (200 W, 400 mTorr) which removes the photoresist. The front side is coated with electron-beam evaporated titanium (3 nm, for adhesion) and gold (5 nm). To ensure good adhesion between the subsequent polymer deposition and the silicon nitride, the cantilevers are primed with a monolayer of 3-aminopropyldimethylethoxysilane in a vapor chamber at 60° C. The sample is placed gold-side down into a reaction chamber for iCVD polymer deposition, so that the underside (non-gold side) of the cantilever is coated with polymer. Even though the membrane and free-standing cantilevers are placed directly onto the aluminum chamber stage, they do not break.

As discussed above, one of the advantages of iCVD over traditional CVD is that the conformality of the polymer coverage can be adjusted by controlling the surface concentrations of the monomers and initiator. In this case a low initiator flow rate is used and high monomer surface concentrations to make the coverage non-conformal and avoid coating the gold side. Furthermore, it has been found that this principle permits one to lithographically pattern the deposited polymer using shadow-masking or lift-off both done directly on a free-standing cantilever. These negative tone patterning processes allow adjacent cantilevers on the same chip to be coated with different polymers, for multiplexed sensing.

On a separate substrate, a set of interdigitated gold wires is patterned to form an open circuit (as depicted in FIG. 1). The space around the wires is covered with a 3 µm thick polymer that is patterned by photolithography. Finally the device is assembled by placing the cantilever gold-side-down above the wires so that an about 3 µm gap is maintained by the spacer polymer.

Example 2

Polymer Film Synthesis

Poly[maleic anhydride-co-vinyl pyrrolidone-co-di(ethylene glycol) di(vinyl ether)] (poly(Ma-V-D)) is synthesized by flowing maleic anhydride, vinyl pyrrolidone, and di(ethylene glycol) di(vinyl ether) (Dedve) monomers into a previously described iCVD chamber [W. E. Tenhaeff and K. K. Gleason, "Initiated chemical vapor deposition of alternating copolymers of styrene and maleic anhydride," *Langmuir*, vol. 23, pp. 6624-6630, June 2007] at rates of 3.6, 1.3, 0.5 sccm, respectively. Poly[maleic anhydride-alt-di(ethylene glycol) di(vinyl ether)] (poly(Ma-D)) is synthesized by feeding maleic anhydride and Dedve at 3.6 and 1.2 sccm, respectively; an alternating copolymer is formed because neither monomer will undergo free radical homopolymerization to a significant extent [W. E. Tenhaeff and K. K. Gleason, "Initiated chemical vapor deposition of alternating copolymers of styrene and maleic anhydride," *Langmuir*, vol. 23, pp. 6624-6630, June 2007; and G. Odian, *Principles of Polymerization*, 4 ed. Hoboken: John Wiley & Sons, 2004]. In both polymer depositions, 0.4 sccm of tert-butyl peroxide initiator and 4 sccm of Ar diluent flow are introduced. The filament temperature is 235° C., substrate temperature is 25° C., and the chamber pressure is 250 mTorr. X-ray photoelectron spectroscopy using a monochromatized Al Kα source (Kratos Axis Ultra) revealed that poly(Ma-V-D) is 53.4% maleic anhydride, 35.7% vinyl pyrrolidone, and 10.9% Dedve, while poly(Ma-D) is 60.5% maleic anhydride and 39.5% Dedve During the deposition, film thickness is controlled and measured by in situ laser interferometry on polished silicon wafer monitors.

Example 3

Device Testing

The sensors were tested in a vapor chamber constructed from an aluminum block with a cavity for vapor introduction; the block was bolted to a temperature controlled stage on which the device was placed. The stage was maintained at 40° C. Nitrogen flow rates into the chamber were controlled with mass flow controllers (MKS Instruments, Model 1479). One nitrogen line (ultra-high purity, Airgas) was bubbled through the liquid analyte, where it became saturated with the analyte vapor. The second line of nitrogen was mixed with the saturated analyte stream prior to entering the chamber to control analyte concentrations. Electrical resistances were logged with a multimeter (Agilent, U1252A) attached to the sensors' electrical leads.

Before and after the reaction with hexylamine, FTIR spectra of blanket polymer films on Si were collected (Nicolet, Nexus 870). Sixty-four scans from 500 to 4000 $cm^{-1}$ with 4 $cm^{-1}$ resolution were collected and integrated using a DTGS KBr detector. The bare Si wafers served as backgrounds. Thicknesses were determined using spectroscopic ellipsometry, with an incident angle of 70° and 190 wavelengths between 315 and 718 nm (J. A. Woollam, M-2000).

Example 4

Comparison of Sensors Coated with Poly(Ma-V-D) and Poly(Ma-D)

Figure 2:
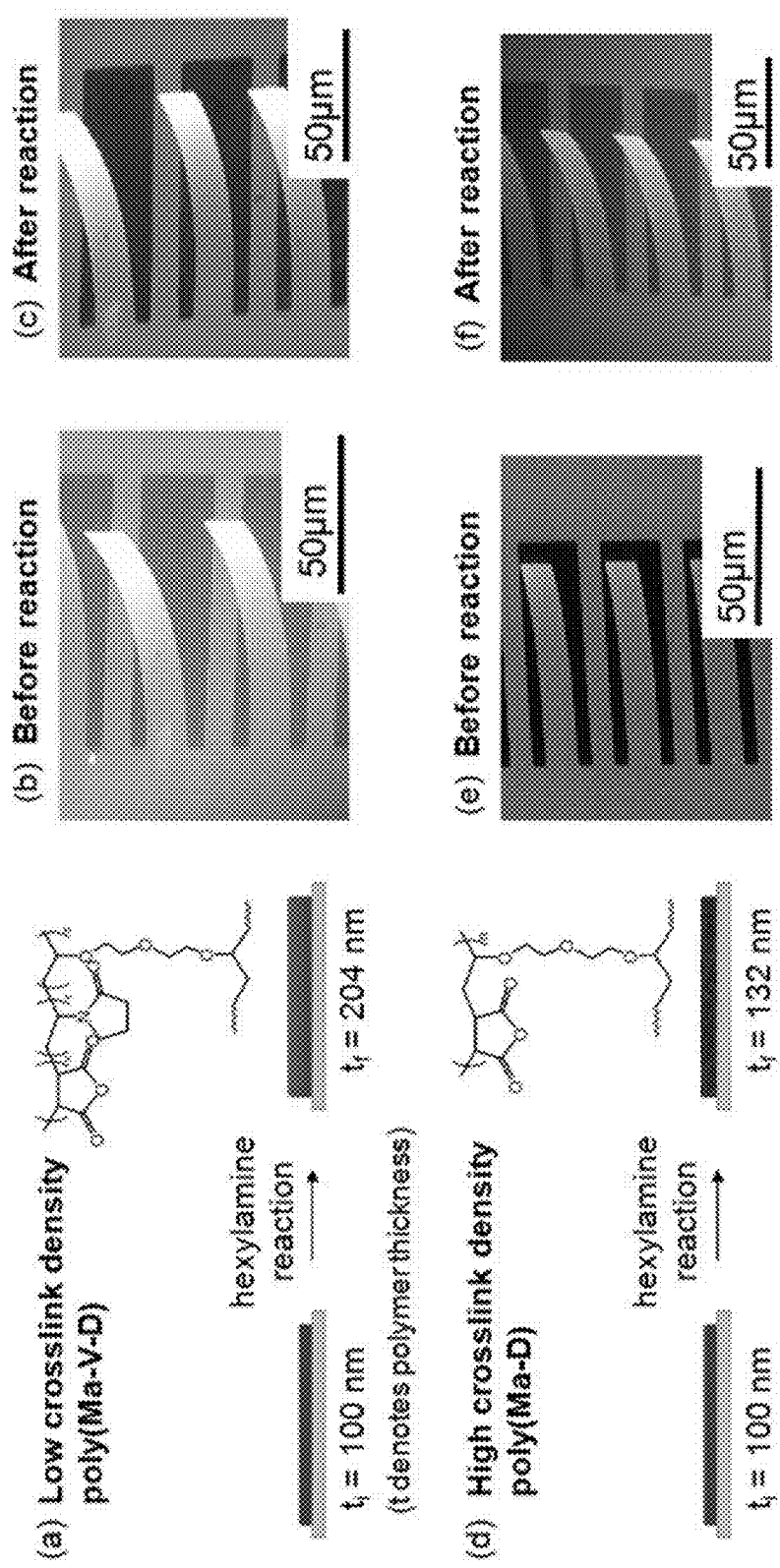
FIG. 2 depicts the comparison of stress formation in lightly and highly crosslinked maleic anhydride polymer after reacting with hexylamine. 100 nm thick silicon nitride cantilevers are coated with iCVD polymer on their undersides. Compressive stress within the polymer causes the cantilevers to bend upwards; the amount of stress determines the curvature. In (b) the cantilevers are initially bent due to intrinsic stress within the polymer from deposition, whereas in (e) there is very little initial stress in the polymer (desired). In both cases, the hexylamine reaction lasted for 60 min, at a concentration of 0.87% in atmosphere, at 40° C. The poly[maleic anhydride-co-vinyl pyrrolidone-co-di(ethylene glycol) di(vinyl ether)] (poly(Ma-V-D)) expanded by 102% and stressed minimally while the poly[maleic anhydride-alt-di(ethylene glycol) di(vinyl ether)] (poly(Ma-D)) expanded by 32% and stressed significantly as evidenced by the increased curvature. In addition, FTIR measurements revealed that 95% of the maleic anhydride had reacted in the poly(Ma-V-D) sample vs. only 49% in the poly(Ma-D) sample, indicating how severely increased crosslinking lowers the diffusion rate.

FIG. 2 shows images of cantilevers coated with poly(Ma-V-D) and poly(Ma-D) before and after the reaction with hexylamine. There is little observable deflection of the cantilevers coated with poly(Ma-V-D), since most of the stress from the added mass of hexylamine is relieved through expansion. This degree of expansion is much more limited in the more cross-linked poly(Ma-D) film resulting in the accumulation of stress desired for deflecting the cantilever. However, the crosslinking in p(Ma-D) also reduces the diffusion of the analyte, creating a tradeoff between stress accumulation and extent of reaction as the degree of crosslinking varies. In making the prototype device, the degree of crosslinking was not optimized and the poly(Ma-D) polymer used comprised of 39.5% cross-linker as shown in FIG. 2d-f.

Assuming that the reaction goes to completion and the polymer layer is uniformly elastically stressed, the cantilever curvature k can be calculated analytically [W. J. Arora, A. J. Nichol, H. I. Smith, and G. Barbastathis, "Membrane folding to achieve three-dimensional nanostructures: Nanopatterned silicon nitride folded with stressed chromium hinges," *Applied Physics Letters*, vol. 88, p. 053108, January 2006] by use of Equation (2):

$$k = \frac{6E_1E_2t_1t_2(t_1+t_2)\cdot(\sigma/E_2)}{E_1^2t_1^4 + E_2^2t_2^4 + 2E_1E_2t_1t_2\cdot(2t_1^2 + 2t_2^2 + 3t_1t_2)} \quad (2)$$

Material parameters for this experiment are: plate modulus $E_1$ is 300 GPa for silicon nitride, $E_2$ is 5 GPa (estimated) for the polymer, and silicon nitride thickness $t_1$ is 100 nm. Given a fixed amount of stress σ from the reaction, the cantilever curvature (and hence deflection) is maximized by choosing the optimal polymer layer thickness, $t_2$. For these parameters, a polymer thickness between about 200 nm to about 300 nm produces a near-maximized curvature. In the experiment described herein, a 75 nm thick polymer layer was used. Based on results shown in FIG. 2, it was deduced that the reaction was diffusion limited and that only the top region of the nanocoating reacted with the analyte in the devices.

Example 5

Measuring Device Performance

Figure 3:
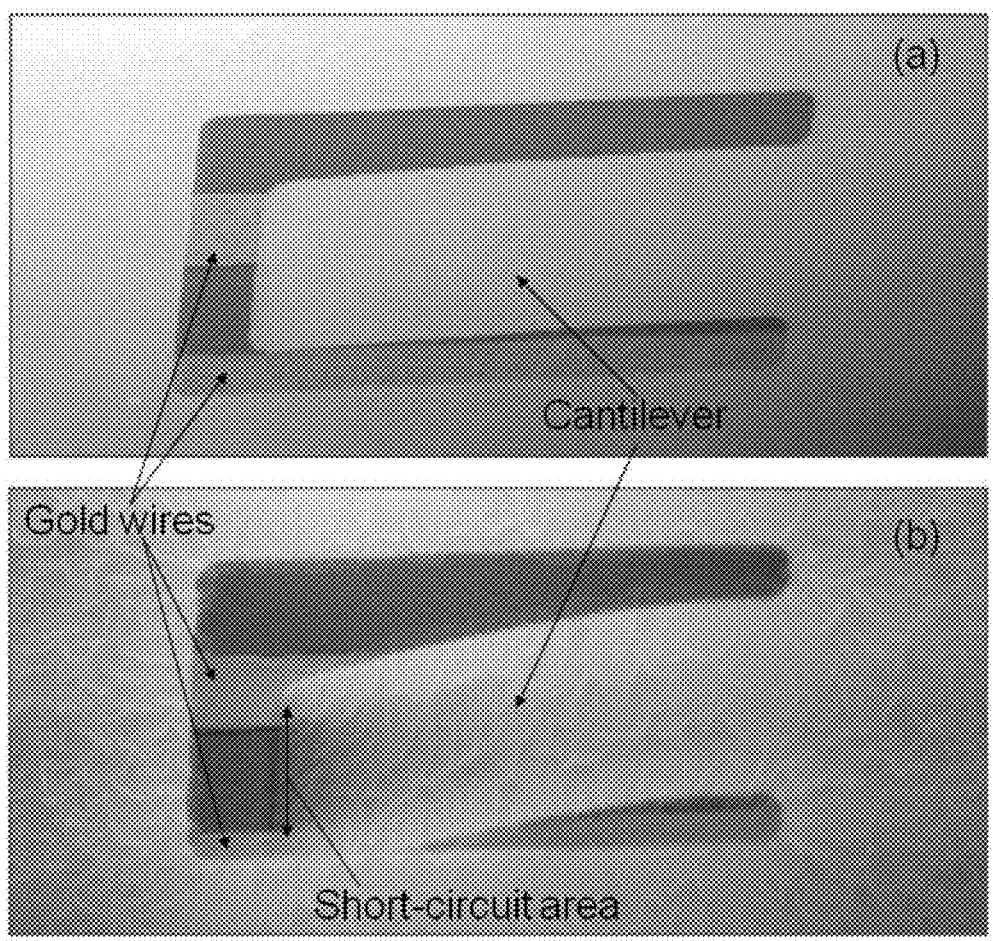
FIG. 3 depicts two environmental-SEM images of an assembled device. Images were taken (a) before reaction and (b) after reaction. Cantilever dimensions are 50×20×0.1 μm; the results in FIG. 4 are reported for 100×20×0.1 μm cantilevers. The cantilever is made free-standing by etching the C-shape out of the silicon nitride membrane. Through this etched portion, the interdigitated gold wires on the substrate below are visible. In both (a) and (b) the visible side of the cantilever is coated with iCVD polymer, and the other side with gold. In (b), the polymer is wrinkled due to the large stress from the reaction.
Figure 4:
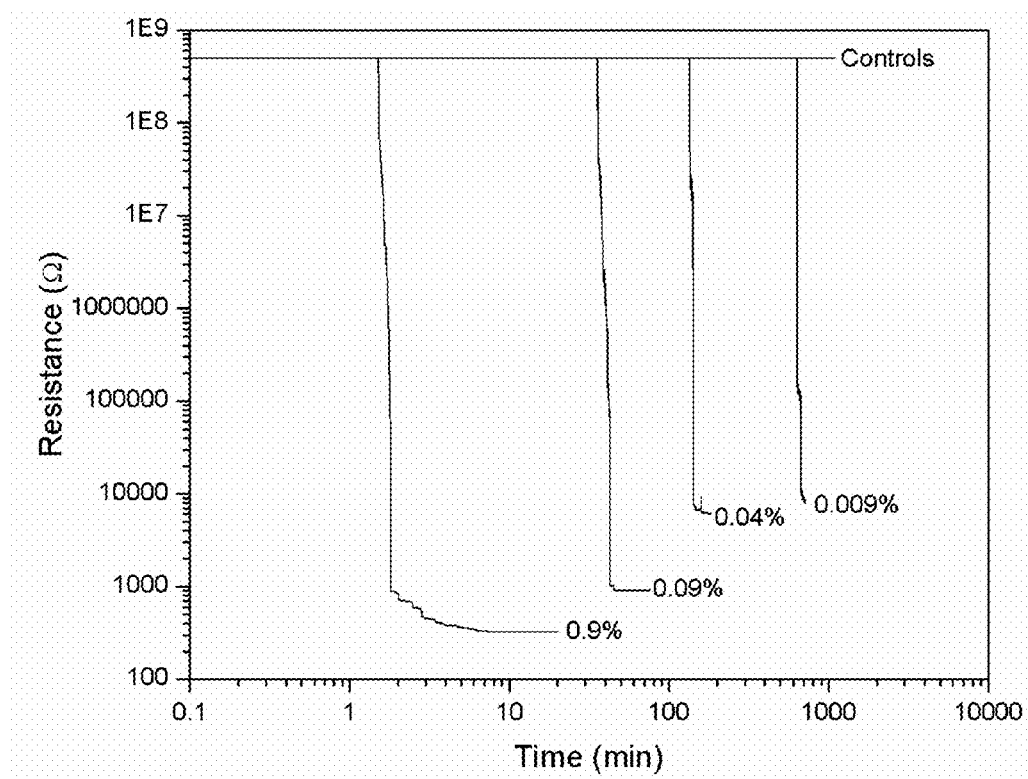
FIG. 4 depicts a graph showing resistance-response data of 100 μm long devices to different concentrations (mol %) of hexylamine gas. Each trace is for a separate device (because the reaction is irreversible). The initial resistance actually exceeds the shown value of 500 MΩ which is the maximum resistance the ohmmeter used could measure. The tests take place in a nitrogen gas chamber, and hexylamine gas is flowed in at time at 0 at the indicated concentrations. The cantilevers start bending downwards immediately as the hexylamine is introduced, but the resistance drop does not occur until the cantilever actually touches the wire pad below. At this point the resistance drops sharply and continues to fall slightly as the reaction proceeds, creating more forceful contact. Three devices were tested for selectivity by exposure to heptane, 2-propanol, and water vapor for 700 minutes. These traces all follow the indicated horizontal line at 500 MΩ because none of them reacted sufficiently to short the circuit.

Images of an assembled switch, both before and after reacting with hexylamine, are shown in FIG. 3. Device performance was assessed by measuring the electrical resistance of the wire leads as hexylamine was introduced to a gas chamber. Resistance vs. time plots are shown in FIG. 4 for four different hexylamine concentrations. In all cases, the electrical response exhibits a drop of several orders of magnitude as one would expect from a contact switch. The response time τ of the sensor is inversely proportional to the gas concentration and given the data in FIG. 4 fits to a power law of $\tau=0.004(X)^{-1.3}$ where X is hexylamine concentration. At 9 parts per thousand of hexylamine in nitrogen, the response time is under two minutes and increases to about 700 minutes for a concentration of 90 parts per million.

Devices were also tested for selectivity to hexylamine by exposure to nitrogen streams saturated with heptane, 2-propanol, and water. The resistance did not drop over each 12 hour test. Because chemical reactions are responsible for creating stress, the device is insensitive to chemicals that do not react with maleic anhydride. However, the device should be sensitive to other amines, alcohols and nucleophiles that will react with maleic anhydride. Although an alcohol, 2-propanol, which was used as a control, does not react with maleic anhydride [B. C. Trivedi and B. M. Culbertson, *Maleic Anhydride*. New York: Plenum Press, 1982].

Therefore, to discriminate between analytes in a given class of chemical compounds, an array of cantilevers with varying aspect ratios could be coated. Analytes with large volumes will create enough stress to deflect all of the cantilevers, while the small analytes would create only enough stress to deflect the longest cantilevers. In addition, to discriminate between classes of chemicals, multiple polymers with differing functionalities could be deposited.

After reacting the devices with hexylamine, they were exposed to 100% nitrogen for 24 hours and observed that the resistance remained constant, indicating that the cantilevers remained stressed and bent. It appears that for these sensors, the tradeoff of attaining high selectivity by chemical binding is that the switch can only be used once and must be replaced afterwards. However, in return one derives great benefit from the low manufacturing cost of each switch.

Example 6

Possible Modifications to Increase Response Time

The response times for the devices discussed above are slow for most applications, but can be improved by optimizing the cantilever geometry to make it more compliant. Given a cantilever of length l, held a fixed distance h above the electrode wires, it is required to bend with curvature k, where $k=h/l^2$, in order to short circuit the electrode wires. (To arrive at this expression, one assumes that $\cos(lk) \approx 1 - (lk)^2$ because the curvature is small when h is much smaller than l). Therefore, increasing the length of the cantilever reduces the required curvature by a square law. According to Equation (2), the curvature is also proportional to the stress in the film, which in turn is proportional the fraction of reacted polymer. Since less polymer mass is required to react, the response time decreases as well. A simple improvement to the current device is to elongate the cantilever by a factor of 10, which should improve the response time by about a factor of 100. In addition, Equation (2) shows that the stress required to achieve a given curvature scales linearly as cantilever and polymer thicknesses are scaled linearly. Using 50 nm thick (instead of 100 nm thick) cantilevers would reduce the response time by another factor of 2. With these two improvements, the response time at 90 ppm of hexylamine should drop from 700 minutes to about 3.5 minutes.

The fundamental sensitivity limitation of this method stems from the requirement that a certain volume of polymer must react to produce enough stress to sufficiently deflect the cantilever. In the experiments described herein, the sensitivity is diffusion limited because the polymer is 75 nm thick. The optimal device would fully actuate upon reaction of just one monolayer of polymer on the cantilever so that it is not diffusion limited but mass transfer limited. The flux of gas molecules F (molecules/area/sec) to a surface is represented by Equation (3):

$$F = \frac{P}{\sqrt{2\pi m k_B T}} \qquad (3)$$

where P is the partial pressure, m is the mass of the molecule, kB is Boltzmann's constant, and T is temperature. At hexylamine concentrations of 1 ppb, the flux is approximately 1 $nm^{-2}$ $s^{-1}$. The surface density of the maleic anhydride functional group has been estimated to be 1 $nm^{-2}$. Assuming all of the hexylamine molecules striking the surface stick and diffuse quickly to a maleic anhydride group, one hexylamine molecule encounters an anhydride group every second and the response time should be on the order of seconds.

Example 7

Other Embodiments of Sensors

The lightly crosslinked pMaVD, which expands by over 100% upon reacting, could also be used as a switch-type, "short-circuiting" sensor. One potential design is shown in FIG. 5, in which the polymer expansion forces a metal contact to short circuit a wire pad.

Because the pMaVD is compatible only with solvent processing, one of the few photoresist that can be processed on top of it is polymethylmethacrylate (PMMA) because it is developed in solvents. PMMA is compatible with scanning electron beam lithography (SEBL), making it easy to test this concept experimentally.

Fabrication details are as follows: Deposit 800 nm pMaVD by initiated chemical vapor deposition. Spin 300 nm PMMA on top of polymer. Hotplate bake 180° C. for 120 sec. Spin 60 nm Aquasave (conductive polymer) on top, hotplate bake 90° C. for 60 sec. SEBL (at 10 keV) of single-pixel lines to define pattern using a dose of 150 pC/cm. (The Aquasave did not work to prevent charging. Despite this, the write worked fine. As an alternative, 5 nm Al layer could be used.) Rinse in water to remove Aquasave, develop in 2:1 IPA:MIBK for 60-120 sec. Rinse in IPA for 15 sec, blow dry with nitrogen. Evaporate 40 nm nickel, and liftoff in NMP (65° C., 30 min). Etch polymer with nickel mask in O2 plasma RIE (pressure 6 mTorr, 150 W power, 200 V bias, 8 min to etch the 1 μm polymer) to form high aspect-ratio lines with a metal top. The fabricated samples were tested by reaction with hexylamine, and the results are shown in FIG. 6. Instead of expanding vertically, the polymer mostly expands laterally.

Anisotropic vertical expansion occurs for thin films bonded to large flat substrates when the length and width of the bonded area is much greater than the film thickness; significant expansion simply cannot occur laterally because of the substrate attachment. However, here the polymer is only attached to the substrate by a 90 nm wide area and is 800 nm tall. Therefore it is reasonable for the polymer to expand mostly laterally instead of vertically. One possible method of forcing anisotropic expansion is to deposit the pMaVD in an alternating stack with another glassy polymer (about 80 nm pMaVD, 10 nm glassy polymer per repeat unit). The glassy polymer will not deform, thus each 80 nm block of pMaVD can effectively be thought of as a thin film attached to a flat substrate and should only expand vertically.

Additional diagrams illustrating how a lightly or non-crosslinked polymer that undergoes a large volume expansion upon reacting (rather than becoming highly stressed) can be used in a contact-switch type of configuration are show in FIGS. 9 and 10. One advantage to such contact-switch type configurations is that since the polymer is less dense, the analyte can diffuse through it more quickly and the polymer-analyte reaction will go faster leading a decreased (improved) response time. In addition, in certain embodiments it is easier to control the gap between electrodes with the polymer deposited over/around a pre-etched trench in the substrate as opposed to using a spacer between a micro-cantilever and the substrate.

Example 8

Approaches to Amplification

It may be possible to modify the polymer coatings discussed above such that their stress response is chemically amplified in a manner analogous to chemically-amplified photoresists. The principle of a chemically amplified photoresist is as follows. The photoresist film is composed of a polymer that bears acid-sensitive groups pendant to the polymer chain. Dissolved in the solid polymer film is a small quantity of a compound that produces an acidic product when it absorbs light. A latent image of acid product is formed in the film when exposed to a pattern of light. In a subsequent heating step, this acid catalyzes the fragmentation of the groups pendant to the polymer chain (termed deprotection). The acid is not consumed in the deprotection reaction and can therefore catalyze the reaction repeatedly. Experimental measurements show that one hundred to on thousand deprotection reactions occur for every acid formed; this is the origin of "chemical amplification". In other words, such an approach would be analogous to chemically-amplified photoresists, except that the triggered chemical reaction produces more stress within the polymer. If the polymer chemistry can be engineered to produce this stress amplification, the sensitivity of these sensors could drop to the parts per trillion range.

It is appreciated that in certain embodiments this technique might in fact relieve stress instead of produce it. For example, as pendant groups are cleaved from the polymers, crosslinks might disappear or small molecules could evaporate from the layer. However, devices may be fabricated to work by relieving stress (e.g. the device could be triggered in a similar manner to the acid-catalyzed depolymerization of polyphthalaldehyde, in which an entire polymer backbone "unzips" and evaporates). In such embodiments, one implementation is to have a cantilever bent upwards by the polymer stress initially, and as the polymer is removed the stress disappears and the cantilever un-bends to make a contact short-circuit.

Example 9

Possible Commercial Uses: Remote Sensing

There are many situations wherein sensors of the invention might be commercially useful, from industrial monitoring to individual protection to remote sensing. Remote sensing is possible because the sensors are low-cost enough to be disposable. In this scenario, one launches a sensor towards a suspected chemical threat (e.g., a bomb) so that it sticks onto it or lands near it. If the target is "hot," the sensor replies with a wireless signal.

For example, in the presence of a specific chemical (e.g., TNT or one of the other chemicals shown below) the crosslinked polymer selectively would react with the chemical resulting in the "volume-confined stress buildup," as discussed above, that causes the cantilever to bend. After deformation, the cantilever would short an electrical circuit, resulting in an alert. Wireless (RF) transmission circuitry could be used as a means for reporting the results of detection to a remote user. An alternative approach would be to spray sensors around suspicious sites, and later come back and probe them wirelessly to see if they have reacted.

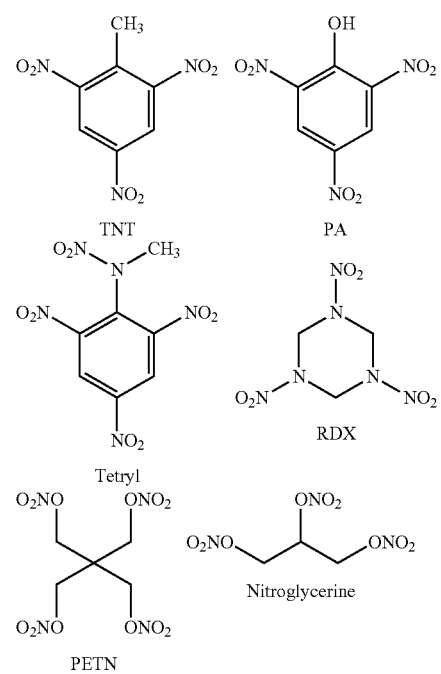

A variety of polymers exhibit specific reactivity with respect to nitroaromatic explosives are known; see review by S. J. Toal and W. C. Trogler, *J. Mater. Chem.*, 16, 2871, 2006. Organic components expected to enable selectivity include a combination of tryptophan and histidine [Jaworski, J. W. et al. *Langmuir* 2008, 24, 4938]; β-cyclodextrin [Yang, X. et al. *Langmuir* 1998, 31, 1505]; 2-amino-hexafluoro-2-propanol [Houser, E. J. et al. *Talanta* 2001, 54, 469], and imidazole functional groups [Jaworski, J. W. et al. *Langmuir* 2008, 24, 4938]. Ellipsometric and spectroscopic measurements on blanket films of these materials could be used to determine the degree to which stress is introduced by binding of TNT, RDX, or other chemical entity.

Example 10

Synthesis and Characterization of Poly(4-Vinylpyridine) as Nitroaromatic-Selective Layers for Microfabricated Sensor Applications Poly(4-vinylpyridine) (P4VP) thin films were synthesized by initiated chemical vapor deposition (iCVD) and evaluated as a nitroaromatic-selective coating for microfabricated sensor applications. Conventional nitroaromatic-selective coatings interact with hydrogen bond basic nitroaromatic compounds through hydrogen bonding. In contrast, P4VP has zero hydrogen bond acidity. Thus, P4VP is a promising material for integration into chemical sensor arrays as the chemical basis for its interaction with nitroaromatics is orthogonal to those in hydrogen bond acidic polymers. Upon exposure to explosive stimulants nitrobenzene and nitrotoluene, the iCVD P4VP layers swelled by over 30%. Additionally, limited swelling was observed with potential interferents: water, ethanol, and toluene. The Flory-Huggins model was also applied to the analysis of the swelling results, which revealed the importance of the interaction parameter, x, in controlling sensors' limits of detection.

Experimental

Polymer Synthesis. Polymer film synthesis was performed in a previously described iCVD reactor system [W. E. Tenhaeff, K. K. Gleason, *Langmuir* 2007, 23, 6624]. 4-vinylpyridine (95%) and tert-butyl peroxide (97%) were purchased from Sigma-Aldrich and used as received. 4-vinylpyridine was heated to 50° C. to create sufficient vapor pressure to enable a flow of 8 sccm into the reactor, controlled using a heated mass flow controller (MKS Instruments, 1152C). The flow rate of tert-butyl peroxide initiator was set at 4 sccm with a mass flow controller (MKS Instruments, 1479). An operating pressure of 800 mTorr was maintained, and the filament temperature was set to 285° C. by passing 1.15 amps through a Chromaloy O (Goodfellow) filament array suspended 1.5 cm above the substrate. The stage temperature was 20° C. to promote adsorption of monomers. In situ interferometry with a 633-nm HeNe laser (JDS Uniphase) was used to monitor and control polymer film thicknesses.

Polymer and Device Characterization. Transmission Fourier transform infrared spectroscopy (FTIR) measurements (Nicolet, Nexus 870 ESP) were collected from 650 to 4000 cm$^{-1}$ with a resolution of 4 cm$^{-1}$ using a MCT detector. 64 scans were integrated to improve the signal-to-noise ratio. FTIR was also collected for as-received, commercial, conventionally synthesized P4VP with a weight-average molecular weight of 60,000 g/mol (Sigma-Aldrich). It was spun coat onto Si wafers from a 4% (w/v) solution in N,N-dimethylformamide (Sigma-Aldrich, 99.9%). FTIR spectra of silicon wafers substrates served as backgrounds, and the spectra were baseline corrected and normalized for comparison purposes.

Molecular weights of iCVD P4VP was determined using a Waters gel permeation chromatography (GPC) system equipped with an isocratic HPLC pump (Model 1515), autosampler (Model 717plus), three styragel columns (HR1, HR3, and HR4), and a refractive index detector (Model 2414). P4VP films were dissolved off the silicon wafers in THF and filtered through a 0.45 µm membrane. 150 µL of the solution was injected into the column; the mobile phase was THF flowing at 1 mL/min. The refractive index detector, operating at a wavelength of 880 nm, was maintained at 35° C. Integrated areas of the peaks were compared to narrow polystyrene standards to characterize the molecular weight distribution.

To test the swelling response of P4VP to nitroaromatics, the films were exposed to nitrogen streams with known concentrations of nitrobenzene (NB) and 4-nitrotoluene (4-NT).

The films were tested in a previously described gas flow cell [W. J. Arora, W. E. Tenhaeff, K. K. Gleason, G. Barbastathis, *J. Microelectromech. Syst.* 2009, 18, 97]. A metered flow rate of nitrogen (Airgas, ultra-high purity) was sparged through the liquid analyte, and the analyte's saturation vapor pressure defined its concentration in $N_2$. A second line of pure nitrogen was mixed with the saturated analyte prior to entering the chamber to control analyte concentrations. In a typical experiment, the first step was to set up steady-state flow of a given nitroaromatic concentration. For the first five minutes, pure $N_2$ was introduced into the sensor chamber. After five minutes, the nitroaromatic stream was fed into the chamber for 20 minutes. The nitroaromatic flow was then turned off, and the chamber was purged with clean $N_2$ for 5 minutes. The films' thickness changes due to swelling was monitored via single wavelength interferometry [N. Vourdas, G. Karadimos, D. Goustouridis, E. Gogolides, A. G. Boudouvis, J. H. Tortai, K. Beltsios, I. Raptis, *Journal of Applied Polymer Science* 2006, 102, 4764] using a 633 nm HeNe laser (JDS Uniphase).

Results and Discussion

Figure 11:
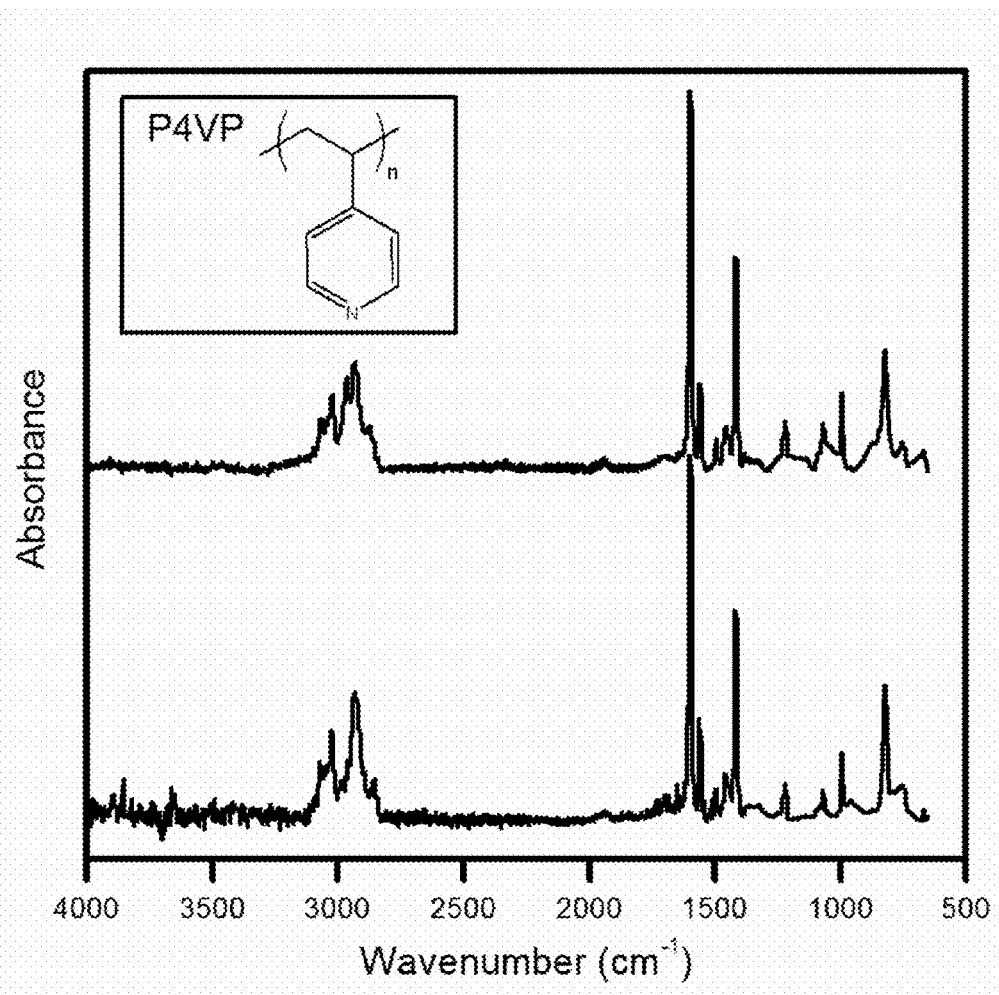
FIG. 11 depicts the comparison of FTIR spectra of iCVD-deposited (top) and standard solution-polymerized (bottom) P4VP. The chemical structure of P4VP is also depicted (inset).

Polymer Synthesis and Characterization. The thickness of poly(4-vinylpyridine) (P4VP) thin films was readily controlled to 125 nm using iCVD. The Fourier transform infrared spectroscopy (FTIR) spectrum of the as-deposited film is provided in FIG. 11, along with the spectrum of a commercial standard. The spectra match qualitatively, suggesting that the compositions of the iCVD and standard polymers are equivalent.

The molecular weight of the iCVD P4VP was determined using gel permeation chromatography. The weight average molecular weight ($M_w$) was 1405 g/mol relative to polystyrene standards, with a polydispersity index of 1.2. The molecular weight of 4-vinylpyridine is 105 g/mol. Therefore, the kinetic chain length was approximately 13.4, and the material can legitimately be considered an oligomer. While it is possible to increase the molecular weight using iCVD [K. Chan, K. K. Gleason, *Macromolecules* 2006, 39, 3890; K. K. S. Lau, K. K. Gleason, *Macromolecules* 2006, 39, 3688; and K. K. S. Lau, K. K. Gleason, *Macromolecules* 2006, 39, 3695], the lower molecular weights obtained here are desirable since they result in lower Tg's [R. J. Andrews, E. A. Grulke, "Glass Transition Temperatures of Polymers", in *Polymer Handbook*, 4 edition, J. Brandrup, E. H. Immergut, and E. A. Grulke, Eds., John Wiley & Sons, New York, 2005, p. 197] and, therefore, higher diffusion constants, P4VP with a $M_w$ of 1405 g/mol was used for all subsequent characterization. Higher diffusion coefficients are desirable since diffusion rates control the sensors' response times.

Swelling Properties of P4VP. The objective in designing chemical sensors is detecting the smallest concentration possible (low limit of detection (LOD)), yet also be selective towards the analyte of interest in order to minimize false positives. Previous studies of nitroaromatic sensing using surface acoustic wave (SAW) devices [E. J. Houser, T. E. Mlsna, V. K. Nguyen, R. Chung, R. L. Mowery, R. A. McGill, *Talanta* 2001, 54, 469] and microcantilevers [L. A. Pinnaduwage, V. Boiadjiev, J. E. Hawk, T. Thundat, *Appl.*

Phys. Lett. 2003, 83, 1471] have reported the importance of hydrogen bonding interactions between hydrogen bond acidic moieties in their polymeric coating and the highly electronegative (hydrogen bond basic) nitro moieties of nitroaromatic compounds. These interactions lead to higher gas-polymer partition coefficients, resulting in lower detection limits.

In common implementations, microcantilever-based sensor systems measure cantilever deflection as its polymer coating absorbs analytes. As a first approximation, the translation of swelling to an observable cantilever deflection can be modeled using Stoney's equation [N. V. Lavrik, M. J. Sepaniak, P. G. Datskos, *Rev. Sci. Instrum.* 2004, 75, 2229] presented in Equation (4):

$$\Delta z = \frac{3l^2(1-v)}{Et^2}\Delta\sigma \qquad (4)$$

In Equation (4), $\Delta z$ is the deflection at the cantilever end, l is the length of the cantilever, v is Poisson's ratio, E is the elastic modulus of the cantilever material, and t is the thickness of the cantilever. $\Delta\sigma$ is the swelling-induced stress. Assuming that the polymer coating is elastic, the stress defined by $\Delta\sigma=-E_p\epsilon$, where $E_p$ is the elastic modulus of the polymer [M. J. Wenzel, F. Josse, S. M. Heinrich, E. Yaz, P. G. Datskos, *Journal of Applied Physics* 2008, 103, 064913]. Strain, $\epsilon$, develops as the polymer swells because the polymer is constrained at the cantilever-substrate interface. Assuming that swelling occurs isotropically when the polymer is not constrained by the substrate, the strain is determined using the formula Equation (5) represented below [M. J. Wenzel, F. Josse, S. M. Heinrich, E. Yaz, P. G. Datskos, *Journal of Applied Physics* 2008, 103, 064913]:

$$\epsilon = \sqrt[3]{Q}-1 \qquad (5)$$

Q is the swelling ratio, the volume of the polymer film in the swollen state over its volume in the dry state. The expressions for stress and strain assume elastic behavior. In reality, though, the behavior of the coating is viscoelastic, and macromolecular rearrangements occur to relieve stress [M. J. Wenzel, F. Josse, S. M. Heinrich, E. Yaz, P. G. Datskos, *Journal of Applied Physics* 2008, 103, 064913]. Plasticization effects also occur. However, these expressions are a first order description of the importance of the polymer swelling process in sensing designs.

Figure 12:
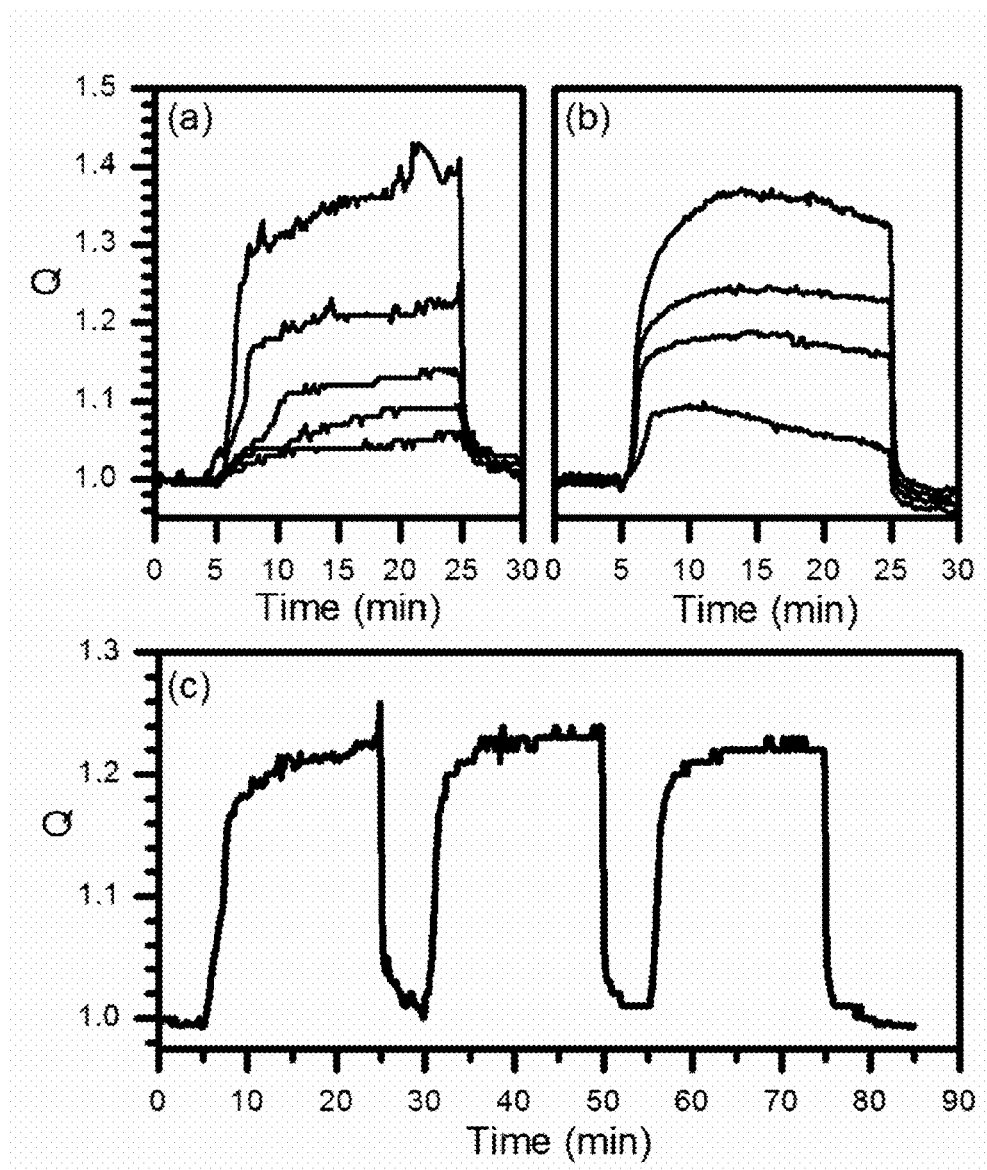
FIG. 12 depicts (a) Swelling of P4VP by NB at 40° C. for $P/P_{sat}$ values of 0.25, 0.4, 0.5, 0.65, 0.85. (Larger $P/P_{sat}$ values result in larger swelling ratios.) (b) Swelling of P4VP by 4NT at 60° C. for $P/P_{sat}$ values of 0.25, 0.4, 0.5, 0.75. The vertical scales in (a) and (b) are equal. (c) Reversibility of P4VP swelling upon repeated exposures to NB (P/Psat=0.65, 40° C.).

To evaluate iCVD-deposited P4VP as a nitroaromatic-selective layer, its interactions with stimulants of nitroaromatic explosives, nitrobenzene (NB) and 4-nitrotoluene (4NT), were examined. These stimulants, rather than TNT or 2,4-dinitrotoluene, were investigated due to safety concerns. The linear swelling ratio ($\alpha$) of P4VP films, which is the ratio of the film thickness in the swollen state to its initial thickness ($t_s/t_i$), was measured as a function of reduced partial pressures ($P/P_{sat}$). Due to constraints imposed by the substrate, there is negligible swelling in the plane of the substrate, and the linear swelling ratio ($\alpha$) is equal to Q. $P/P_{sat}$ is the ratio of an analyte's vapor pressure to its saturation pressure at the system temperature, and it is directly proportional to the concentration of the analyte in the vapor head space. Linear swelling was measured at 40° C. for NB and 60° C. for 4NT. Swelling by 4NT was measured at a higher temperature due to the lack of reliable vapor pressure data below its melting point of 51° C. The results are shown in FIG. 12.

In order to generate the desired reduced partial pressures, the carrier $N_2$ stream saturated with analyte was fixed at a constant flow rate and mixed with an appropriate patch flow. Mass transfer calculations and experiments were performed to show that the swelling process was diffusion limited. Since the process is diffusion limited, the effect of varying $N_2$ flow rates on residence time did not influence the swelling kinetics or equilibrium. For the first five minutes, there was no flow into the sensor chamber in order to collect a baseline. After five minutes, the valve was opened to introduce the nitroaromatic stream, resulting in swelling of the P4VP films. Fickian kinetics do not apply since swelling naturally modifies the physical properties of the polymer, resulting in a concentration-dependent diffusion constant. Investigation of the NB swelling kinetics reveals at least two distinct stages of diffusion. There is an initial increase in film thickness due to NB sorption, followed by a second sharp increase, after which the swelling equilibrium is reached. This behavior is characteristic of Super Case II diffusion [A. Sfirakis, C. A. Rogers, *Polymer Engineering and Science* 1981, 21, 542; and A. H. Windle, "Case II Sorption", in *Polymer Permeability*, J. Comyn, Ed., Elsevier Applied Science Publishers, New York, 1985]. After 20 minutes of nitroaromatic introduction, the sensor chamber was purged with pure nitrogen.

FIG. 12(c) shows that the swelling is reversible. The nitroaromatic source was turned off after 20 minutes, and pure $N_2$ was introduced into the chamber. The film thickness shrank to its original thickness within five minutes. The maximum swelling ratios of the second and third cycles were qualitatively the same as the first cycle. However, the second and third cycles reached 95% of their equilibrium value within 90 seconds, as opposed to the first cycle which didn't fully reach equilibrium. By looking closely at the swelling profiles, one can also see that the second and third cycles do not display the two-stage process as in the first. Presumably, the polymer film has undergone relaxation from the first nitroaromatic absorption cycle. In the subsequent cycles, the diffusion coefficients start at higher values since the polymer is already relaxed.

In addition to measuring the linear expansion of these films, a method was developed to generalize the results for comparison to other polymer-analyte systems. The Flory-Huggins model describes the thermodynamics of mixing of polymers in small molecules (solvent) [P. J. Flory, "*Principles of Polymer Chemistry*", Cornell University Press, Ithaca, 1953]. The model can be extended to polymer-vapor systems by relating the chemical potential term in the traditional formulation to the reduced partial pressure of vapor molecules [H. Elbs, G. Krausch, *Polymer* 2004, 45, 7935]:

$$P/P_{sat}=(1-\phi_p)\exp[(1-1/N)\phi_p+\chi\phi_p^2] \qquad (6)$$

Here $\phi_p$ is the volume fraction of polymer at equilibrium (swollen state), $\chi$ is the Flory-Huggins interaction parameter for the analyte-polymer pair, and N is the degree of polymerization. Because the polymer volume fraction of the film is initially unity, the film's equilibrium swelling ratio (Q) is related to the volume fraction of polymer by $Q=1/\phi_p$, and Equation (6) becomes $$\frac{P}{P_{sat}} = \left(1-\frac{1}{Q}\right)\exp\left[(1-1/N)\left(\frac{1}{Q}\right)+\chi\left(\frac{1}{Q}\right)^2\right] \qquad (7)$$

Unfortunately, Equation (7) cannot be solved explicitly for Q. By analyzing Equations 4, 5, and 7 together, though, it is clear that the LOD of the sensing device is lowered by reducing the required $P/P_{sat}$ for a given Q. Therefore, Equation (7) indicates that the best sensitivities are achieved by synthesizing polymers with small or negative $\chi$ values for nitroaromatics.

Figure 13:
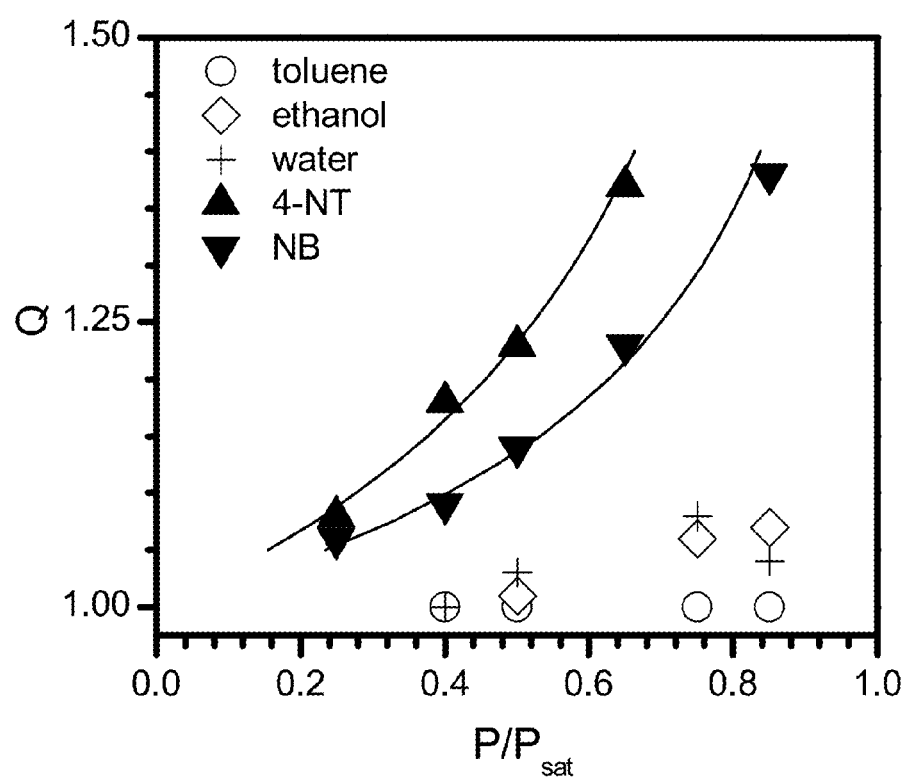
FIG. 13 depicts equilibrium volumetric swelling ratios of P4VP with nitroaromatics and potential interferents. The lines describe the Flory-Huggins model (Equation (7)) fitted to the swelling data using a non-linear least square minimization algorithm.

The equilibrium swelling ratios are plotted as function of $P/P_{sat}$ in FIG. 13. Equation (7) was fitted to the data in FIG. 13 to obtain x values of 0.71 for NB at 40° C. and 0.25 for 4NT at 60° C. A $\chi$ value of 0.5 is indicative of an ideal solution, where the heat of mixing is zero [I. W. Hamley, "Introduction to Soft Matter", John Wiley & Sons, New York, 2000]. $\chi$ is less than 0.5 for both 4NT, indicating that favorable intermolecular forces develop between it and P4VP. Further studies to understand the difference in $\chi$ values for 4NT and NB and investigate the interaction of heavier nitroaromatics with P4VP are warranted. The Flory-Huggins equation is a convenient analyze selectivity and sensitivity and predicted results between systems as x parameters are tabulated for many solvent-polymer pairs [N. Schuld, B. A. Wolf, "Polymer-solvent interaction parameters", in Polymer Handbook, 4th edition, J. Brandrup, E. H. Immergut, and E. A. Grulke, Eds., John Wiley & Sons, New York, 2003, p. 247].

The selectivity of P4VP for nitroaromatics is also important. When deployed in the field, a sensor will be exposed to a complex vapor composition that will vary with time and environmental conditions. For field success and operator confidence, the sensor must be selective towards nitroaromatics and not respond to other environmental interferents. The swelling responses of P4VP to water, which is omnipresent as humidity, ethanol, which is a product of biological processes, and toluene, which mimics hydrocarbon fuel, were tested at 60° C. The results are provided in FIG. 13 with a comparison to the swelling by nitroaromatics. A $\chi$ value of 1.9 was calculated for the P4VP-water and P4VP-ethanol systems at 60° C. This quantitatively shows that these interactions are weaker than the P4VP-nitroaromatic interactions. Unfortunately, $\chi$ could not be determined for the P4VP-toluene system since the experimental technique did not have the precision to measure the swelling ratio, which was not significantly greater than one. Equation (7) breaks down when Q=1 for $P/P_{sat}$>0.

FIG. 13 clearly demonstrates that the swelling ratio at a given reduced partial pressure is greatest for the nitroaromatics. Relatively little swelling is observed for the interferents tested. It is possible other interferents exist that will significantly swell P4VP. The importance of this particular polymer composition becomes apparent by comparing it to sorbent polymers currently employed in nitroaromatic sensors. Previous studies, particularly those concerning surface acoustic wave sensors, use partition coefficients, rather than $\chi$, to analyze the suitability of polymers for different analytes [E. J. Houser, T. E. Mlsna, V. K. Nguyen, R. Chung, R. L. Mowery, R. A. McGill, Talanta 2001, 54, 469; and R. A. McGill, M. H. Abraham, J. W. Grate, Chemtech 1994, 24, 27]. The partition coefficient is calculated by dividing the equilibrium concentration of analyte absorbed in the polymer by the concentration of analyte in the vapor phase. An important metric for comparing polymers for sensor applications is the selectivity (S), which is the ratio of sorbed analyte to the ratio of sorbed interferent:

$$S = \frac{K_{Pa}c_a}{K_{Pi}c_i} \quad (8)$$

Here, $K_{Pa}$ is partition coefficient for the analyte of interest, $c_a$ is the concentration of the analyte vapor, $K_{Pi}$ is the partition coefficient of potential interferents, and $c_i$ is the concentration of interferent vapor. Partition coefficients can be determined experimentally or estimated using the linear solvation energy relationship (LSER) [R. A. McGill, M. H. Abraham, J. W. Grate, Chemtech 1994, 24, 27]. The LSER framework allows one to determine the relative importance of various types of intermolecular forces in the solvation process.

Nitroaromatic compounds are hydrogen bond basic and do not contain any hydrogen bond acidity [R. A. McGill, T. E. Mlsna, R. Chung, V. K. Nguyen, J. Stepnowski, Sensors and Actuators B: Chemical 2000, 65, 5]. A common strategy in designing nitroaromatic-selective polymers is to synthesize polymers with high hydrogen bond acidity [J. W. Grate, Chem. Rev. 2008, 108, 726]. Poly(4-(hexafluoroisopropanol)-styrene) (P4V) and poly(methyl(3,5-bis(hexafluoroisopropanol)phenyl)siloxane) (SXPHFA) are some of the best performing polymers, but the hydrogen bond acidity of carbowax polymers [G. K. Kannan, J. C. Kappor, Sens. Actuator B-Chem. 2005, 110, 312; and G. K. Kannan, A. T. Nimal, U. Mittal, R. D. S. Yadava, J. C. Kapoor, Sens. Actuator B-Chem. 2004, 101, 328] and self-assembled monolayers of 4-mercaptobenzoic acid [L. A. Pinnaduwage, V. Boiadjiev, J. E. Hawk, T. Thundat, Appl. Phys. Lett. 2003, 83, 1471] have also been used successfully. It is important to consider the selectivity of these polymers for nitroaromatics relative to water. Water contains both hydrogen bond acidity and basicity, so hydrogen bond interactions can form between water and hydrogen bond acidic polymers. Using previously reported data from McGill et al. [R. A. McGill, T. E. Mlsna, R. Chung, V. K. Nguyen, J. Stepnowski, Sensors and Actuators B: Chemical 2000, 65, 5] in the LSER equation, the selectivity of P4V for nitrobenzene relative to water at 25° C. was calculated to be 332($c_a/c_i$).

P4VP and nitroaromatics, on the other hand, interact though pi-pi stacking and charge transfer complexes in solution. Based on the LSER parameters for pyridine, P4VP does not contain hydrogen bond acidity. It does contain hydrogen bond basic groups and can interact through hydrogen bonds with water, which likely contributed to the swelling reported in FIG. 13. LSER parameters of P4VP were not determined using chromatographic techniques. Instead, the partition coefficients of P4VP for nitrobenzene and water were determined experimentally by estimating the analyte concentrations from the swelling data. Vapor concentrations were calculated using the $P/P_{sat}$ values. The experimentally determined selectivity of P4VP was 58($c_a/c_i$).

The selectivity of P4V for NB is 5.7 times greater than P4VP's selectivity. However, P4V's selectivity is 100 times greater than other hydrogen bonding polymers [E. J. Houser, T. E. Mlsna, V. K. Nguyen, R. Chung, R. L. Mowery, R. A. McGill, Talanta 2001, 54, 469]. The selectivity of SXPHFA is not reported, but is likely on the same order of magnitude as P4V's. While highly selective, P4V is semi-crystalline, which is not ideal for gas diffusion purposes. Regardless of its performance relative to hydrogen bonding polymers, P4VP will be useful in sensor arrays since its interaction with nitroaromatics is orthogonal to hydrogen bonding interactions.

Conclusion

Thin films of P4VP have been synthesized by iCVD and shown to swell upon exposure to nitroaromatics. The use of iCVD is important as it provides many advantages over other coating processes [W. E. Tenhaeff, K. K. Gleason, Adv.

Funct. Mater. 2008, 18, 979], some of which have been demonstrated in other sensor studies [W. J. Arora, W. E. Tenhaeff, K. K. Gleason, G. Barbastathis, *J. Microelectromech. Syst.* 2009, 18, 97]. While the interaction of amine bases with TNT have been studied in solution, the implementation of P4VP for sensor applications has not been exploited. The Flory-Huggins theory has been applied to the analysis of the swelling results, and the importance of x in determining sensitivities for microcantilever-based systems has been demonstrated. The use of the Flory-Huggins equation should be extended to further analysis of sensor designs since x values have been tabulated for many polymer-solvent pairs [N. Schuld, B. A. Wolf, "Polymer-solvent interaction parameters", in *Polymer Handbook,* 4th edition, J. Brandrup, E. H. Immergut, and E. A. Grulke, Eds., John Wiley & Sons, New York, 2003, p. 247]. While the selectivity of P4VP for nitrobenzene over water is 5.7 times lower than P4V's selectivity, the swelling of P4VP with nitroaromatics is nonetheless an important result as it provides a complimentary interaction for multicomponent sensors.

Example 11

Analysis and Demonstration of Microfabricated Trench-Based Sensors

Utilization of the swelling response of poly(4-vinylpyridine) (P4VP) thin films to nitroaromatic vapors for microfabricated sensing designs was detailed in Example 10. Transduction of the polymer's response to mechanical deflection of microcantilevers was analyzed. These microcantilevers have typical dimensions of hundreds of micrometers (length) by tens of micrometers (width) by one micrometer (thickness) [N. V. Lavrik, M. J. Sepaniak, P. G. Datskos, *Rev. Sci. Instrum.* 2004, 75, 2229]. The influence of these dimensions on a sensor's performance, the length and thickness in particular, is apparent from Equation (4). The requirements for micrometer-scale dimensions limit further miniaturization of the sensing component. Miniaturization is an important objective in order to fabricate inconspicuous devices indiscernible to the naked eye.

Moreover, it was shown that crosslinking is required to create permanent deflections of the cantilever end on the order of a few micrometers [W. J. Arora, W. E. Tenhaeff, K. K. Gleason, G. Barbastathis, *J. Microelectromech. Syst.* 2009, 18, 97]. It is believed that the response time of the sensors is controlled by diffusion of the analyte into the polymer layer. Crosslinking creates glassy polymers, and the resulting diffusion coefficient is orders of magnitude lower than uncrosslinked or rubbery polymers [W. J. Koros, W. C. Madden, "Transport Properties", in *Encyclopedia of Polymer Science and Technology,* 3rd edition, J. Korschwitz and H. F. Mark, Eds., Wiley-Interscience, Hoboken, 2002]. Theory describes the influence of crosslinking on the glass transition temperature of a polymer, which defines the temperature at which the transition from a rubbery to glassy state occurs [J. Bicerano, "Glass Transition", in *Encyclopedia of Polymer Science and Technology,* 3rd edition, J. Korschwitz and H. F. Mark, Eds., Wiley-Interscience, Hoboken, 2002]. To maximize the diffusion coefficient, the operating temperature of the sensor should be as high as possible above the glass transition temperature.

Figure 14:
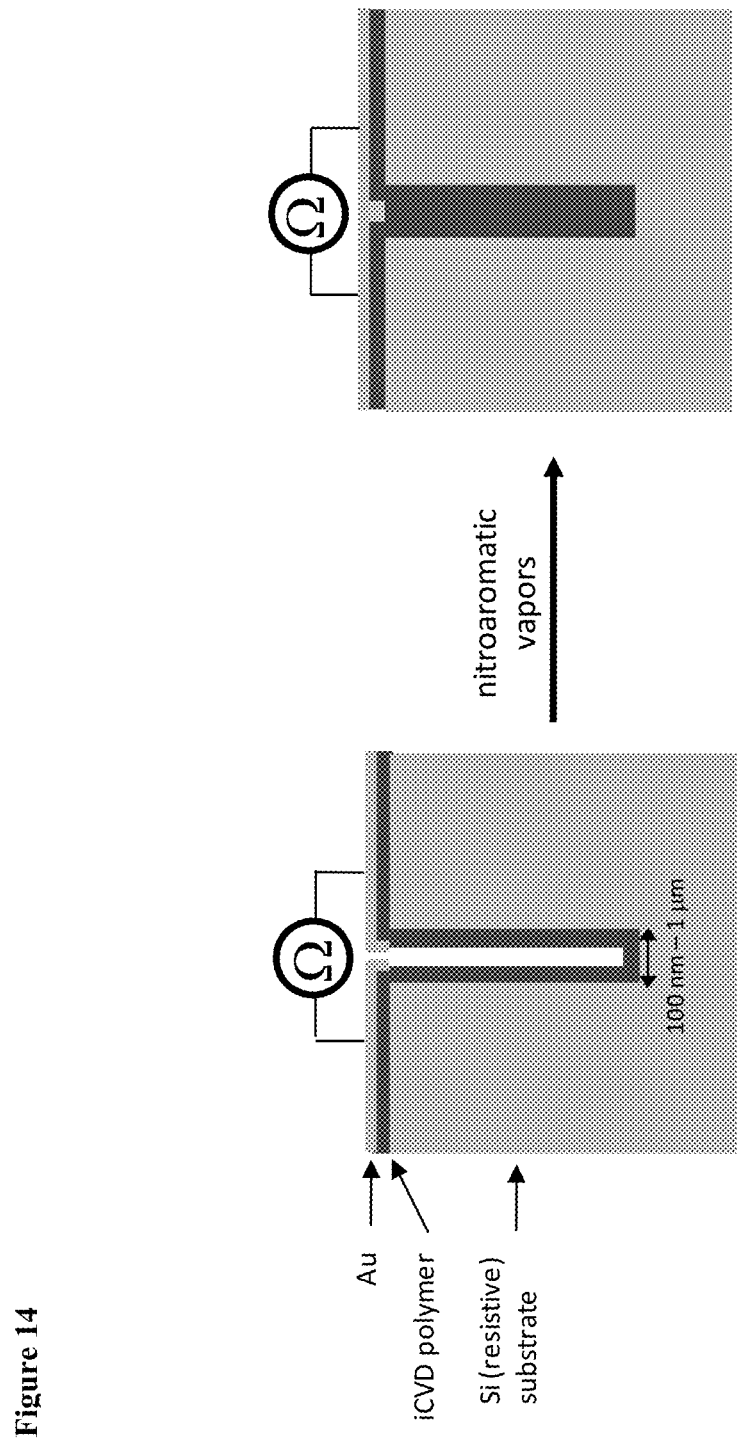
FIG. 14 depicts the conceptual design of the trench sensors, showing the utilization polymer swelling to transduce a chemical interaction into an electrical measurement. The polymer swelling results in contact being made between Au layers that are initially separated.

A sensing architecture has been designed to overcome these limitations. The sensing concept is shown in FIG. 14. Here, polymer does not need to create stress in the substrate for signal transduction. Rather, physical contact between two swelling polymer layers is used to bring together two electrically conductive layers. To maximize the extent of polymer swelling and minimize response time, crosslinking can be eliminated. Moreover, the critical length scale of this design (the trench width) is over at least two orders of magnitude smaller than conventional micro cantilever lengths (>100 μm).

Herein, this design is quantitatively analyzed for the detection of nitroaromatics using the P4VP properties determined in Example 10; fabrication and testing of the device for nitroaromatic sensing has not been performed. However, this design has been tested for detection of hexylamine, as described below.

Design

Figure 15:
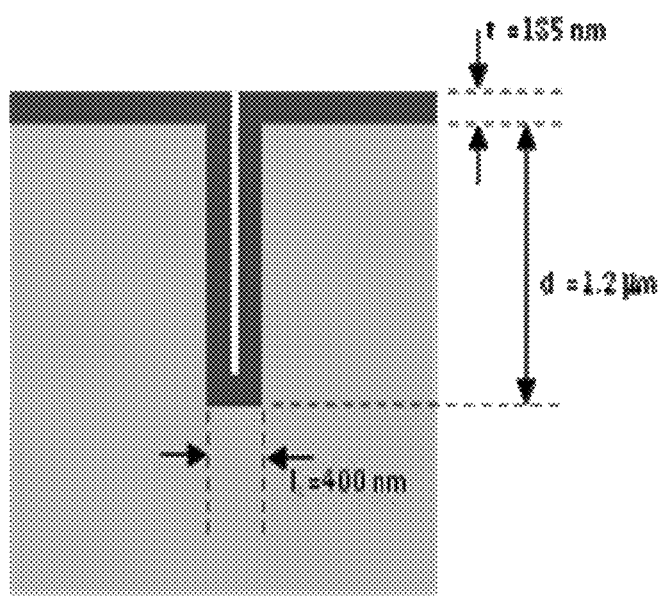
FIG. 15 depicts key measurements for analyzing the sensitivities of trench sensors.

A 400 nm-wide trench that is 1.2 μm deep has been analyzed as an instructive example, using parameters of P4VP determined as noted above. By depositing a 185 nm-thick P4VP film in the interior of the trench as shown in FIG. 15, the P4VP layers must swell by 8.1% upon exposure to nitroaromatics to create contact between the gold surfaces and decrease the electrical resistance measured across the trench. Because swelling occurs normal to the surface only, Q=1.081. The $\chi$ values of 2,4-dinitrotoluene (DNT) and (TNT) with P4VP are unknown, but they are roughly estimated to be equal to $\chi$ for the 4NT-P4VP system at 60° C., which was measured in Example 10 ($\chi$=0.25). Using these Q and x values, $P/P_{sat}$ must be equal to 0.23 for trench closure (calculated using Equation 7). The saturated partial pressures of DNT and TNT are 204 and 8.6 μTorr, respectively. Therefore, this design can achieve sensing LODs of 62.2 and 2.64 ppb for DNT and TNT, respectively.

In addition to the concentration LOD, the LOD on a mass basis is important. The concentration LOD describes the lowest concentration that can be detected, but it does not determine the kinetics or the required sampling volume to create a response. The required sampling volume is important because it determines response times. For example, it is possible that a sensor design can detect extremely small concentrations, but if the surface area of the active layer is high, the sensor may fail to create a response due to the limited amount of analyte molecules in the vapor sample. Therefore, the mass LOD is an important metric. A lower mass LOD translates to better kinetics and smaller sampling volumes. To reduce the mass LOD using the trench concept, the volume of the polymer coating should be minimized. A top down image of a patterned sensor is given in FIG. 17; it does not show larger conductive pads, which are required to make electrical measurements but do not affect the mass LOD. The pattern dimensions were chosen somewhat arbitrarily. However, based on experience, they can be readily fabricated with conventional microfabrication techniques. The linewidth of the pattern is critical as the top Au layer is impermeable, requiring analytes to diffuse into the underlying P4VP from the side.

Figure 16:
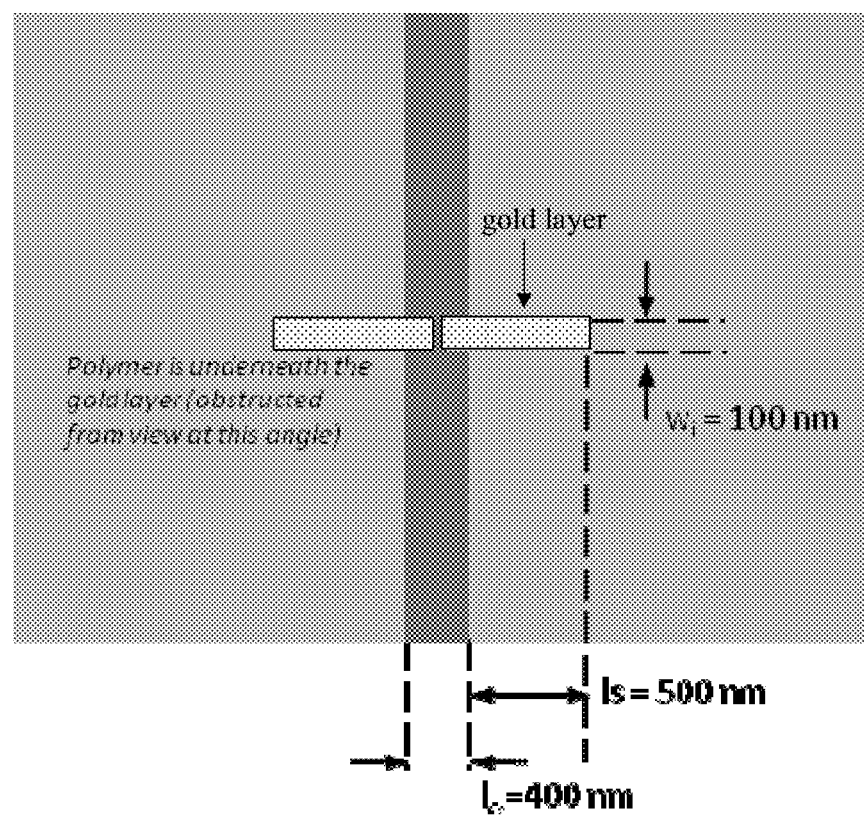
FIG. 16 depicts an illustration of patterning the responsive and conductive layers to minimize the mass limit of detection of swelling-based trench sensors.

A first approximation of the required mass is calculated from the following equation, which assumes volume additivity:

$$m_{LOD}=\rho V_i(Q-1) \quad (9)$$

wherein $m_{LOD}$ is the mass limit of detection, p is the density of the absorbed analyte, $V_i$ is the initial volume of the polymer, and Q is the swelling ratio. The initial volume is calculated by $V_i=t_iw_i\,(2l_s+2d_t+l_t)$; the variables are defined in the figures above. Using the dimensions shown in FIGS. 15 and 16, along with an assumed density of 1.6 g/cm³ for absorbed nitroaromatic, the mass LOD is 9.1 fg.

Figure 17:
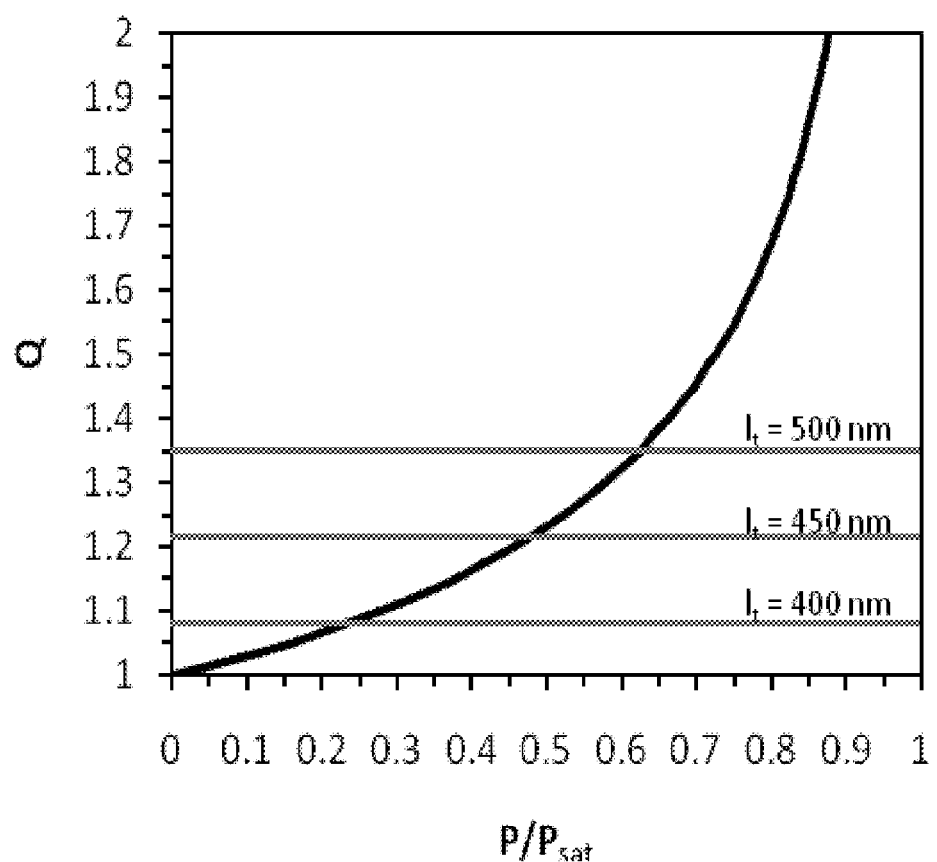
FIG. 17 depicts the use of multiple trench widths to quantify analyte concentration levels. $P/P_{sat}$ is directly proportional to the vapor concentration.

Currently, this design is a "yes-no" switch; it only activates once the vapor concentration of analyte exceeds the concentration LOD. It does not discern concentration levels. For practical application in explosives sensors, this is sufficient. The operator only needs to know whether or not explosives are present. In other applications, discriminating between concentration levels is desired. This sensing design can be modified by creating multiple trenches of varying widths, and simultaneously monitoring resistance across all of them. An array of three trenches with widths of 400, 450, and 500 nm, coated with 185 nm of P4VP has been analyzed. FIG. 17 presents a plot of the Flory-Huggins equation for $\chi=0.25$ along with the horizontal lines representing the required swelling ratios to create contact between the three trenches. The intersections of the horizontal lines with the Flory-Huggins model show how the required $P/P_{sat}$ (or equivalently vapor phase concentration) is affected. For further complexity, multiple polymers with varying $\chi$ values can be deposited to create multicomponent responses for analyte identification.

Experimental

Polymer Deposition and Device Fabrication. Silicon wafers substrates with pre-patterned trenches (nominally 750 nm wide at the top of the trench by 6 μm deep) were generously supplied by Ed Gleason of Analog Devices. Approximately 400 nm of a silicon oxide hard mask remained on top of the wafer, resulting in an electrical resistance greater than 500 MΩ measured across the trench. Poly(maleic anhydride) (pMA) was deposited on these substrates in a previously described iCVD reactor configuration [W. E. Tenhaeff, K. K. Gleason, *Langmuir* 2007, 23, 6624]. Maleic anhydride (MA) was heated to 90° C. to generate sufficient vapor pressure such that 10 sccm of MA vapor could be regulated through a heated mass flow controller (MKS Instruments, 1152C). The flow rate of tert-butyl peroxide initiator was set at 4 sccm with a mass flow controller (MKS Instruments, 1479). An operating pressure of 200 mTorr was maintained, and the filament temperature was set to 285° C. by passing 1.15 amps through a Chromaloy O (Goodfellow) filament array suspended 1.5 cm above the substrate. The stage temperature was 25° C. to promote adsorption of monomers. In situ interferometry with a 633-nm HeNe laser (JDS Uniphase) was used to monitor and control polymer film thicknesses.

Approximately 5 nm of an Au/Pd was deposited on top of the pMA film using a sputter coater (Quorom Technologies, SC7640). The leads of electrical wires were bonded to both sides of the trench using conductive silver epoxy.

Device Characterization. The response of the device to hexylamine was measured using a previously described vapor flow cell [W. J. Arora, W. E. Tenhaeff, K. K. Gleason, G. Barbastathis, *J. Microelectromech. Syst.* 2009, 18, 97]. A metered flow rate of nitrogen (Airgas, ultra-high purity) was sparged through liquid hexylamine, and the saturation vapor pressure of hexylamine defined its concentration in $N_2$. A second line of pure nitrogen was mixed with the saturated analyte prior to entering the chamber to control analyte concentrations. In a typical experiment, the first step was to set up steady-state flow of a given hexylamine concentration. For the first five minutes, pure $N_2$ was introduced into the sensor chamber. After five minutes, the hexylamine stream was fed into the chamber until the electrical resistance of the device stabilized. The hexylamine flow was then turned off, and the chamber was purged with clean $N_2$ for five minutes. Pure nitrogen flowed during the last five minutes of all resistance logging experiments. The wire leads were fed through the chamber's seals in order to log electrical resistance as a function of time with a standard multimeter (Agilent, U1252A). Images of the trench cross-sections were collected before and after hexylamine exposure with a scanning electron microscope (FEI, XL30).

Results and Discussion

Design. The two primary findings from analyzing the trench sensor design are the mass and concentration LODs using P4VP to detect nitroaromatics. They are estimated to be 9.1 fg and 2.6 ppb, respectively, for TNT. Amplifying fluorescent polymers that are utilized in the iCX Fido® system are generally considered to be the most promising commercialized technology [V. L. Pamula, "Detection of Explosives", in *Handbook of Machine Olfaction, Electronic Nose Technology*, T. C. Pearce, S. S. Schiffman, H. T. Nagle, and J. W. Gardner, Eds., Wiley-VCH, Weinheim, 2003, p. 547]. The Fido® design has mass and concentration LODs on the order of femtograms and parts per quadrillion, respectively [R. L. Woodfin, "*Trace Chemical Sensing of Explosives*", John Wiley & Sons, Hoboken, 2007]. Clearly, the Fido® system outperforms this design in terms of the concentration LOD (6 orders of magnitude better). In terms of mass, the performances are about the same. However, trench sensors have the advantage in terms of size and power requirements. In the Fido® design, the fluorescence of the amplifying fluorescent polymer is continuously monitored as it is exposed to collimated UV laser light [V. L. Pamula, "Detection of Explosives", in *Handbook of Machine Olfaction, Electronic Nose Technology*, T. C. Pearce, S. S. Schiffman, H. T. Nagle, and J. W. Gardner, Eds., Wiley-VCH, Weinheim, 2003, p. 547]. This requires constant power. Because low power requirements are required in many sensing concepts, trench sensors are promising for these designs. Moreover, a pre-concentrator, which is a common component of practical implementations of sensors [R. L. Woodfin, "*Trace Chemical Sensing of Explosives*", John Wiley & Sons, Hoboken, 2007], can be used to increase the concentration of nitroaromatics that is exposed to the trench sensors in order to address their poor concentration LOD.

Figure 18:
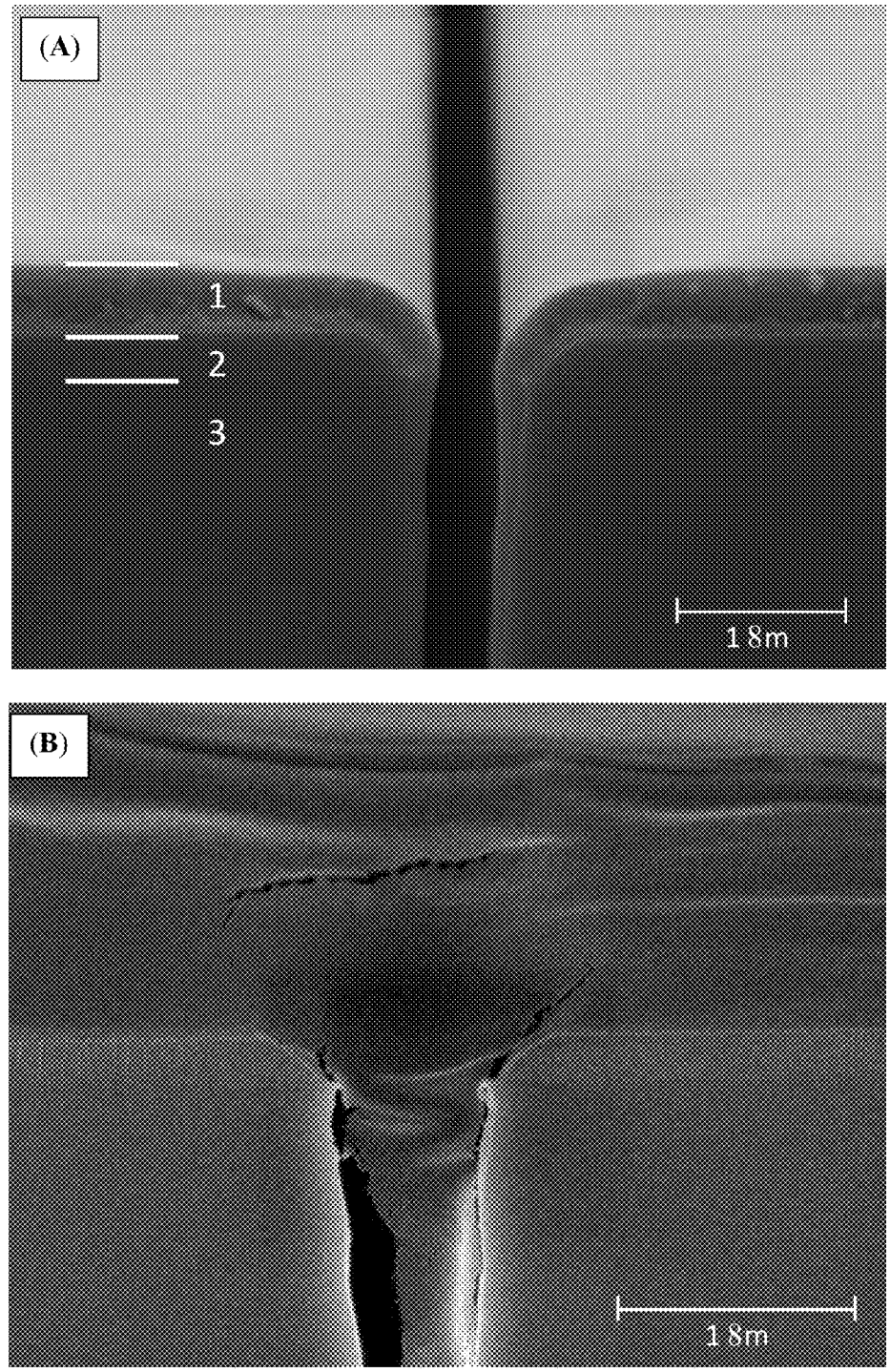
FIG. 18 depicts SEM images of the pMA-coated trenches (a) before and (b) after reaction with hexylamine. In (a), the (1) P4VP coating, (2) silicon oxide resistive layer, and (3) silicon substrate are identified. In (b) the polymer layers contact each other after the reaction with hexylamine.

Performance of the pMA and Hexylamine System. SEM images of the pMA films in the trenches are provided in FIG. 18. Prior to the reaction of pMA with hexylamine, the pMA film thickness was approximately 400 nm on the substrate surface and 185 nm in the trench interior, measured normal to the trench lip (the slight protrusion near the top). The surfaces of the polymer films were separated by 340 nm. FIG. 18(*a*) shows that the thickness of the coating decreases down the depth of the trench, and the polymer coatings at the bottom of the trench will not contact after expansion from the hexylamine reaction. However, only the polymer films at the top of the trench need to be brought together to change the resistance. After exposure to hexylamine, the volume expansion clearly resulted in contact between the two sides, as seen in FIG. 18(*b*). The film on the substrate surface was measured to be 1.2 μm thick, which was determined in other images (not readily apparent in FIG. 18(*b*)). During fabrication, a blanket layer of Au/Pd was deposited to reduce the complexity of the process. Stresses of the volume expansion of pMA led to cracking and wrinkling of the Au/Pd.

The electrical resistance measurements of the sensors' responses to hexylamine vapors at a system temperature of 40° C. are provided in FIG. 19 and compared to the results obtained using poly(Ma-D) coatings on microcantilevers. These sensors clearly behaved as switches, showing drops in resistance of four orders of magnitude. The initial resistance of the sensor used for the 400 ppm hexylamine test did not start at 500 MΩ, which suggests that some of the Au/Pd coating sputter coating was able to bridge the trenches. Effort was not taken to determine whether a continuous Au/Pd coating was present at the bottom of the trench. It is possible that particulate contamination became lodged at the top of the trench, which allowed Au/Pd to bridge there. In either case, efforts can be taken to eliminate these problems if they reoccur.

It is important to note the differences between the testing procedures used to generate the plots in FIG. 19. In FIG. 19(a), a baseline prior to hexylamine introduction was not recorded, while in FIG. 19(b), there was no hexylamine flow into the chamber while the resistance was measured for the first five minutes. To the response time of the trench sensors to the microcantilever sensors, five minutes must be subtracted from the response time of the trench sensors. At hexylamine concentrations of 8700 ppm, the response time of the microcantilever switch was 90 seconds, while the response time for the trench switch was five minutes. At 870 ppm, the response times were 35.8 min and 38 min for the microcantilever and trench sensors, respectively. The trench sensors are not providing expected improvements in response times likely due to the blanket layer of Au/Pd that was sputtered on top of the P4VP during sensor fabrication. Significant improvements in the response time of the trench sensors should be possible by patterning the sputter-deposited Au/Pd. Au/Pd is relatively impermeable to Au/Pd, which limits the mass transfer of hexylamine into the pMA layer. Quantitative results are not reported, but preliminary diffusion experiments showed a blanket layer of Au/Pd prevents diffusion of hexylamine into underlying pMA. Therefore, in these sensors, hexylamine is diffusing through defects in the Au/Pd coating on the surface or entering the pMA through uncoated regions in the trench. For all future experiments with lower vapor pressure nitroaromatics, the Au/Pd will need to be patterned.

Another difference between the microcantilever and trench-based sensors is the final resistance of the closed circuit. The resistances of closed circuit in the microcantilever sensors ranged from 100-1000Ω. The trench sensors, on the other hand, had resistances above 10,000Ω on average. The reason for this is apparent in FIG. 18. The reaction of the hexylamine with pMA led to significant volume expansion, the stress of which exceeded the tensile strength of the Au/Pd layer, resulting in cracking. The cracking or wrinkling leads to a noncontinuous film, and the electrical conductivity of the layer is reduced. This problem cannot be avoided for the hexylamine-pMA system, as pMA will continue to absorb hexylamine molecules until the layer has completely reacted and expanded to its equilibrium size. This effect may not be an issue with the P4VP-nitroaromatic system, as swelling is more limited, and the system can be designed so that the swelling required to close the switch generates a stress in the Au/Pd coating that is less than its tensile strength. It is unclear why the resistance increased slightly when the system is purged with clean $N_2$ at the end of the test.

Conclusion

The design of a resistance-based microscale chemical sensing concept has been described. The performance of P4VP for the detection of nitroaromatics using this design was analyzed. Analysis showed that the sensitivity in terms of the mass limit of detection should be comparable to sensors using amplifying fluorescent polymers. However, the system should offer many other advantages, such as the reduction of size and power requirements. A quantitative comparison of the power requirements was not made, but the chemical switch design offers obvious advantages in terms of power. Moreover, a prototype device was fabricated as a proof of principle. Due to limitations in fabrication capabilities, optimal performance of these devices was not reported. Fabrication techniques to improve key performance metrics were identified. Utilizing these techniques will be crucial when the trench sensors are fabricated for nitroaromatic vapors, which have lower vapor phase concentrations than hexylamine and reduced thermodynamic driving forces for sorption.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An apparatus comprising: a first element having a top and bottom; and a second element having a top and bottom; wherein the bottom of the first element is positioned facing the top of the second element with a gap therebetween; the bottom of the first element is coated with a polymer having a thickness of between about 0.1 µm and about 500 µm the polymer is electrically conducting or is coated with an electrically conductive material; the top of the second element is electrically insulating and comprises on its surface non-contiguous electrically conducting material connected to at least two electrical leads; and upon contact with an analyte the polymer closes the gap as a result of swelling or stressing of the polymer, thereby electrically connecting the non-contiguous electrically conducting material.

2. The apparatus of claim 1, wherein the width of the gap is between about 0.1 µm and about 10 µm.

3. The apparatus of claim 1, wherein the non-contiguous electrically conducting material comprises one or more nano- or microfabricated conductive lines.

4. The apparatus of claim 3, wherein the nano- or microfabricated conductive lines comprise a conductive material selected from the group consisting of silver, copper, gold, aluminum, iron, steel, brass, bronze, rhodium, iridium, platinum, titanium, mercury, graphite, and alloys thereof.

5. The apparatus of claim 3, wherein the nano- or microfabricated conductive lines form a closed circuit.

6. The apparatus of claim 3, wherein the nano- or microfabricated conductive lines form an open circuit.

7. The apparatus of claim 3, wherein the nano- or microfabricated conductive lines comprise gold.

8. The apparatus of claim 3, wherein the nano- or microfabricated conductive lines are interdigitated.

9. The apparatus of claim 1, wherein the electrically conductive material is selected from the group consisting of silver, copper, gold, aluminum, iron, steel, brass, bronze, rhodium, iridium, platinum, titanium, mercury, graphite, and alloys thereof.

10. The apparatus of claim 1, further comprising a microbattery connected to one of the electrical leads.

11. The apparatus of claim 1, further comprising reporting circuitry connected to one of the electrical leads.

12. The apparatus of claim 1, further comprising an RF transmitter connected to one of the electrical leads.

13. The apparatus of claim 1, wherein the polymer is selected from polymers and co-polymers comprising one or more of the monomers selected from the group consisting of H$_2$C=C(R)X, H$_2$C=C(R)C(=O)X, H$_2$C=C(R)C(=O)OX, H$_2$C=C(R)C(=O)N(R$^1$)X, H$_2$C=C(R)C(=O)SX, H$_2$C=C(R)OC(=O)X, H$_2$C=C(R)N(R$^1$)C(=O)X, H$_2$C=C(R)SC(=O)X, H$_2$C=C(R)OX, H$_2$C=C(R)N(R$^1$)X, H$_2$C=C(R)SX, H$_2$C=C(R)S(=O)X, and H$_2$C=C(R)S(=O)$_2$X;

wherein, independently for each occurrence:

X is selected from the group consisting of hydrogen, alkyl, cycloalkyl, heterocycloalkyl, aryl, heteroaryl, aralkyl, heteroaralkyl, and —(CH$_2$)$_n$Y;

R is selected from the group consisting of hydrogen and alkyl;

R$^1$ is selected from the group consisting of hydrogen, alkyl, aralkyl, heteroaralkyl, and carboxyl; or R$^1$ taken together with X and the nitrogen to which they are bound, are —CH$_2$CH$_2$CH$_2$— or —CH$_2$CH$_2$CH$_2$CH$_2$—;

Y is selected from the group consisting of hydrogen, alkyl, cycloalkyl, heterocycloalkyl, aryl, heteroaryl, aralkyl, heteroaralkyl, nitro, halo, hydroxyl, alkyoxy, aryloxy, carboxyl, heteroaryloxy, amino, acylamino, amido, carbamoyl, sulfhydryl, sulfonate, and sulfoxido; and n is 1-10 inclusive.

14. The apparatus of claim 1, wherein the polymer is selected from polymers and co-polymers comprising one or more of the monomers selected from the group consisting of maleic anhydride, N-vinyl-2-pyrrolidone, p-bromophenyl methacrylate, pentabromophenyl methacrylate, N-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorostyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, benzyl acrylate, 2-hydroxyethyl acrylate, dimethylaminoethyl acrylate, Et$_3$DMAA (N,N-dimethylacetoacetamide), sec-butyl acrylate, tert-butyl acrylate, isobornyl acrylate, ethylene glycol diacrylate, methyl methacrylate, ethyl methacrylate, n-propyl methacrylate, n-butyl methacrylate, isobutyl methacrylate, n-pentyl methacrylate, n-hexyl methacrylate, n-heptyl methacrylate, sec-butyl methacrylate, tert-amyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, ortho-methyl styrene, meta-methyl styrene, para-methyl styrene, para-ethyl styrene, 2,4-dimethyl styrene, 2,5-dimethyl styrene, m-divinylbenzene, p-divinylbenzene, vinylimidazole, 1,4-divinyloxybutane, diethylene glycol divinyl ether, 1,5-hexadiene-3,4-diol, methyl trans-cinnamate, N-morpholinoethyl acrylate, 2-morpholinoethyl methacrylate, 2-isocyanatoethyl methacrylate, 2-sulfoethyl methacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino) ethyl methacrylate, 2-bromoethyl methacrylate, 2-phenylethyl methacrylate, and 4-vinylpyridine.

15. The apparatus of claim 1, wherein the polymer is selected from polymers and co-polymers comprising one or more of the monomers selected from the group consisting of maleic anhydride, N-vinyl-2-pyrrolidone, and 4-vinylpyridine.

16. The apparatus of claim 1, wherein the polymer is a polymer or co-polymer comprising 4-vinylpyridine.

17. The apparatus of claim 1, wherein the polymer comprises pendant tryptophan, histidine, β-cyclodextrins, hexafluoropropan-2-ol, or imidazole functional groups.

18. The apparatus of claim 1, wherein the polymer comprises a crosslinker.

19. The apparatus of claim 18, wherein the crosslinker is selected from the group consisting of di(ethylene glycol) di(vinyl ether), ethyleneglycol diacrylate or dimethacrylate, di-, tri- or tetraethylen-glycol diacrylate or dimethacrylate, allyl acrylate or methacrylate, a C$_2$-C$_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol diacrylate or dimethacrylate, methylene bisacrylamide or methylene bismethacrylamide, ethylene bisacrylamide or ethylene bismethacrylamide, and triallyl phthalate or diallyl phthalate.

20. The apparatus of claim 18, wherein the crosslinker is di(ethylene glycol) di(vinyl ether).

21. The apparatus of claim 1, wherein the first element comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

22. The apparatus of claim 1, wherein the second element comprises silicon, silicon nitride, silicon oxide, polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, or polythiophene.

23. The apparatus of claim 1, wherein the first element is mechanically connected to the second element.

24. The apparatus of claim 1, wherein the thickness of the polymer is between about 0.1 μm and 10 μm.

25. The apparatus of claim 1, wherein the thickness of the polymer is about 1 μm.

26. The apparatus of claim 1, wherein the first element and/or the second element is coated with a compound to aid in the binding of polymer to the first element and/or the second element.

27. The apparatus of claim 26, wherein the compound is an aminoalkyl silane.

28. The apparatus of claim 26, wherein the compound is 3-aminopropyldimethylethoxy-silane.

29. A method for assaying at least one analyte in a sample or an environment comprising the steps of:

exposing an apparatus to the sample or environment; and detecting or measuring a change in the resistance of the apparatus;

wherein the apparatus comprises a first element having a top and bottom; and a second element having a top and bottom;

wherein the bottom of the first element is positioned facing the top of the second element with a gap therebetween; the bottom of the first element is coated with a polymer having a thickness of between about 0.1 μm and about 500 μm; the polymer is electrically conducting or is coated with an electrically conductive material; the top of the second element is electrically insulating and comprises on its surface non-contiguous electrically conducting material connected to at least two electrical leads; and upon contact with an analyte the polymer closes the gap as a result of swelling or stressing of the polymer, thereby electrically connecting the non-contiguous electrically conducting material.

* * * * *